US012649742B2

(12) United States Patent
Parent et al.

(10) Patent No.: US 12,649,742 B2
(45) Date of Patent: Jun. 9, 2026

(54) CRYSTALLINE FORMS OF A PYRROLOPYRIDINE-ANILINE COMPOUND

(71) Applicant: NFLECTION THERAPEUTICS, INC., Boston, MA (US)

(72) Inventors: Stephan D. Parent, West Lafayette, IN (US); Courtney S. Johnson, West Lafayette, IN (US); John Kincaid, Boston, MA (US)

(73) Assignee: NFLECTION THERAPEUTICS, INC., Boston, MA (US)

( * ) Notice: Subject to any disclaimer, the term of this patent is extended or adjusted under 35 U.S.C. 154(b) by 394 days.

(21) Appl. No.: 18/273,315

(22) PCT Filed: Jan. 20, 2022

(86) PCT No.: PCT/US2022/013146

§ 371 (c)(1),
(2) Date: Jul. 20, 2023

(87) PCT Pub. No.: WO2022/159594

PCT Pub. Date: Jul. 28, 2022

(65) Prior Publication Data

US 2025/0179062 A1 Jun. 5, 2025

Related U.S. Application Data

(60) Provisional application No. 63/139,975, filed on Jan. 21, 2021.

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
USPC .......................................................... 514/300
See application file for complete search history.

(56) References Cited

U.S. PATENT DOCUMENTS

| | | | |
|---|---|---|---|
| 8,252,838 | B2 | 8/2012 | Kisak et al. |
| 8,283,359 | B2 | 10/2012 | Hutchings et al. |
| 11,161,845 | B2 | 11/2021 | Kincaid et al. |
| 12,065,439 | B2 | 8/2024 | Kincaid et al. |
| 12,310,950 | B2 | 5/2025 | Powala et al. |
| 2005/0202001 | A1 | 9/2005 | Koo et al. |
| 2009/0030058 | A1 | 1/2009 | Pervez et al. |
| 2009/0082328 | A1 | 3/2009 | Li et al. |
| 2009/0246198 | A1 | 10/2009 | Dong et al. |
| 2010/0179124 | A1 | 7/2010 | Johnson et al. |
| 2010/0215579 | A1 | 8/2010 | Kung et al. |
| 2010/0256149 | A1 | 10/2010 | Goutopoulos et al. |
| 2012/0082702 | A1 | 4/2012 | Delucca et al. |
| 2013/0345181 | A1 | 12/2013 | Bavetsias et al. |
| 2014/0213598 | A1 | 7/2014 | Liu et al. |
| 2015/0023915 | A1 | 1/2015 | Morrison et al. |
| 2015/0258048 | A1 | 9/2015 | Old |
| 2015/0335644 | A1 | 11/2015 | Seykora |
| 2018/0256570 | A1 | 9/2018 | Peterson et al. |
| 2019/0224210 | A1 | 7/2019 | Barbion et al. |
| 2019/0270734 | A1 | 9/2019 | Gasser et al. |
| 2020/0165243 | A1 | 5/2020 | Kincaid et al. |
| 2021/0275495 | A1 | 9/2021 | Vivier |
| 2022/0033399 | A1 | 2/2022 | Kincaid et al. |
| 2022/0110862 | A1 | 4/2022 | Powala et al. |
| 2023/0255945 | A1 | 8/2023 | Powala et al. |
| 2024/0228480 | A1 | 7/2024 | Houghton et al. |
| 2025/0034137 | A1 | 1/2025 | Kincaid et al. |

FOREIGN PATENT DOCUMENTS

| | | | |
|---|---|---|---|
| CN | 105384754 | A | 3/2016 |
| CN | 105384738 | B | 8/2017 |
| EP | 2549979 | A2 | 1/2013 |
| JP | 2009525317 | A | 7/2009 |
| JP | 2010501584 | A | 1/2010 |
| JP | 2010501585 | A | 1/2010 |
| JP | 2010511626 | A | 4/2010 |
| JP | 2020514156 | A | 5/2020 |
| WO | 9901426 | A1 | 1/1999 |
| WO | 0042029 | A1 | 7/2000 |
| WO | 03077914 | A1 | 9/2003 |
| WO | WO-2006130160 | A2 | 12/2006 |
| WO | WO-2007002433 | A1 | 1/2007 |
| WO | WO-2007088345 | A1 | 8/2007 |
| WO | WO-2008020206 | A2 | 2/2008 |
| WO | WO-2008024724 | A1 | 2/2008 |

(Continued)

OTHER PUBLICATIONS

CAS Registry No. 1887242-63-8, 3-Pyridinecarboxylic acid, 6-cyano-2-[(2-fluoro-4-iodophenyl)amino]-5-methyl-, ethyl ester (ACI), entered Apr. 7, 2016, 2 pages.
International Search Report and Written Opinion for International Application No. PCT/US2022/013153, mailed Jun. 8, 2022, 13 pages.
International Search Report and Written Opinion for International application No. PCT/US2022/050794, mailed Apr. 24, 2023, 14 pages.
KOctober 18, 2023) National Cancer Institute, HPV and Cancer, National Institutes of Health, Retrieved from the internet Jul. 2, 2024, https://www.cancer.gov/about-cancer/causes-prevention/risk/Infectious-agents/hpv-and-cancer#:-:textLong-lasting, 9 pages.
Pubchem SID 230153403—SCHEMBL4202810, Feb. 12, 2015, 8 pages.

(Continued)

*Primary Examiner* — Niloofar Rahmani
(74) *Attorney, Agent, or Firm* — Mintz, Levin, Cohn, Ferris, Glovsky and Popeo, P.C.

(57) ABSTRACT

The present disclosure provides crystalline forms of the compound having formula (I): (I), wherein the crystalline forms are crystalline Forms A, B, C, E, F, and H, each of which is characterized by an X-ray powder diffraction (XRPD) pattern. The present disclosure also provides methods for preparing crystalline forms, in particular Form A. The present disclosure further provides methods of treating various skin disorders using the crystalline forms of the disclosure or a pharmaceutical composition thereof.

20 Claims, 17 Drawing Sheets

(56) References Cited

FOREIGN PATENT DOCUMENTS

| | | | | | |
|---|---|---|---|---|---|
| WO | WO-2008024725 | A1 | | 2/2008 | |
| WO | WO-2008055236 | A2 | | 5/2008 | |
| WO | WO-2008067481 | A1 | | 6/2008 | |
| WO | 2008079814 | A2 | | 7/2008 | |
| WO | WO-2008148034 | A1 | | 12/2008 | |
| WO | WO-2009082687 | A1 | | 7/2009 | |
| WO | WO-2009093008 | A1 | | 7/2009 | |
| WO | WO-2009093009 | A1 | | 7/2009 | |
| WO | WO-2009093013 | A1 | | 7/2009 | |
| WO | WO-2009153554 | A1 | | 12/2009 | |
| WO | 2011117034 | A2 | | 9/2011 | |
| WO | WO-2012040636 | A2 | | 3/2012 | |
| WO | WO-2014179785 | A1 | | 11/2014 | |
| WO | 2014210538 | A1 | | 12/2014 | |
| WO | 2018213807 | A1 | | 11/2018 | |
| WO | WO-2018213810 | A1 | * | 11/2018 | ............. A61P 35/00 |
| WO | 2019139970 | A1 | | 7/2019 | |
| WO | WO-2020106303 | A1 | | 5/2020 | |
| WO | WO-2020106304 | A1 | | 5/2020 | |
| WO | WO-2020106307 | A1 | | 5/2020 | |
| WO | 2022159600 | A1 | | 7/2022 | |
| WO | WO-2022159594 | A1 | | 7/2022 | |
| WO | 2023096935 | A1 | | 6/2023 | |

OTHER PUBLICATIONS

Registry No. 1008526-41-7, entered STN Mar. 18, 2008, 9 pages.
Farschtschi et al. (2015) "Keratinocytic Epidermal Nevus Syndrome with Schwann Cell Proliferation, Lipomatous Tumour and Mosaic KRAS Mutation", BMC Medical Genetics, 16(6):1-7.
Garibyan et al. (Mar. 2013) "Research Techniques Made Simple: Polymerase Chain Reaction (PCR)", Journal of Investigative Dermatology, 133(3):1-8.
Luo et al. (2014) "Epidermal, Sebaceous, and Melanocytic Nevoid Proliferations Are Spectrums of Mosaic RASopathies", Journal of Investigative Dermatology, 134(10):2493-2496.
Price Steve, (2008) "Putative allosteric MEK1 and MEK2 inhibitors", Expert Opinion on Therapeutic Patents, 18(6):603-627.
Sarin et al. (2023) "Development of a MEK Inhibitor, NFX-179, as a Chemoprevention Agent for Squamous Cell Carcinoma", Science translational medicine, 15(717):eade1844 (10 pages).
Zhang et al. (2014) "All-trans Retinoic Acid Induces Cell-cycle Arrest in Human Cutaneous Squamous Carcinoma Cells by Inhibiting the Mitogen-activated Protein Kinase-activated Protein 1 Pathway", Experimental Dermatology, 39(3):354-60.
EP Application No. 22 74 3173 Search Report Apr. 28, 2025.
Caira, Ed-Montchamp Jean-Luc, "Crystalline Polymorphism of Organic Compounds", Topics in Current Chemistry; Springer, Berlin, De, vol. 198, pp. 163-208, 1998.
Takata, "API form screening and selection in drug discovery stage", Pharm Stage, 6(10):20-25, Jan. 15, 2007.
Hirayama, "Handbook for the Preparation of Organic Compound Crystals", Maruzen Publishing Co., Ltd., 2008, pp. 17-23, 37-40, 45-51, and 57-65, 2008.
Serizawa, "Optimization of salt and crystal forms and crystallization techniques", Pharm Tech Japan 18(10):81-96, 2002.
Director, Evaluation and Licensing Division, Pharmaceutical Safety Bureau, Ministry of Health and Welfare, "Refer to the Guideline for Residual Solvents in Pharmaceuticals", Iyakusin, 1998.
Adams et al., Design and Synthesis of Orally Available MEK Inhibitors With Potent in Vivo Antitumor Efficacy, Bioorganic & Medicinal Chemistry Letters, 2012, 22(7), pp. 2411-2414.
Akinleye et al., MEK and the Inhibitors: From Bench to Bedside, Journal of Hematology & Oncology, 2012, 6(27), 11 pages.
Hatzivassiliou et al., Mechanism of MEK inhibition determines efficacy in mutant KRAS-versus BRAF-driven cancers, Nature, 2012, 501(7466), pp. 232-236.
International Search Report and Written Opinion for International PCT Application No. PCT/US2018/033544 mailed Aug. 9, 2018, 11 pages.
International Search Report and Written Opinion for International PCT Application No. PCT/US2018/033547, mailed Aug. 9, 2018,10 pages.
International Search Report and Written Opinion for International PCT Application No. PCT/US2022/013146, mailed Apr. 8, 2022, 7 pages.
Laing et al., Fused Thiophene Derivatives as MEK Inhibitors, Bioorganic & Medicinal Chemistry Letters, 2012, 22(1), pp. 472-475.
Wallace et al., Structure-based Design and Synthesis of Pyrrole Derivatives as MEK Inhibitors, Bioorganic & Medicinal Chemistry Letters, 20120, 20(14), pp. 4156-4158.
RN 1347327-80-3 Registry ED Entered STN: Dec. 2, 2011.
RN 1347341-78-9 Registry ED Entered STN: Dec. 2, 2011.
RN 1347421-15-1 Registry ED Entered STN: Dec. 2, 2011.
RN 1348075-68-2 Registry ED Entered STN: Dec. 4, 2011.
RN 1348201-64-8 Registry ED Entered STN: Dec. 4, 2011.
RN 1348347-40-9 Registry ED Entered STN: Dec. 4, 2011.
RN 1348375-35-8 Registry ED Entered STN: Dec. 4, 2011.
RN 1348394-69-3 Registry ED Entered STN: Dec. 4, 2011.
RN 1348492-53-4 Registry ED Entered STN: Dec. 4, 2011.
RN 1348494-88-1 Registry ED Entered STN: Dec. 4, 2011.
RN 1348595-42-5 Registry ED Entered STN: Dec. 4, 2011.
RN 1348618-58-5 Registry ED Entered STN: Dec. 4, 2011.
RN 1348655-12-8 Registry ED Entered STN: Dec. 4, 2011.
RN 1348673-54-0 Registry ED Entered STN: Dec. 4, 2011.
RN 1349147-82-5 Registry ED Entered STN: Dec. 5, 2011.
RN 1349255-80-6 Registry ED Entered STN: Dec. 5, 2011.
RN 1349369-24-9 Registry ED Entered STN: Dec. 6, 2011.
RN 1349383-92-1 Registry ED Entered STN: Dec. 6, 2011.
RN 1349420-35-4 Registry ED Entered STN: Dec. 6, 2011.
RN 1349476-92-1 Registry ED Entered STN: Dec. 6, 2011.
RN 1349510-77-5 Registry ED Entered STN: Dec. 6, 2011.
RN 1349524-53-3 Registry ED Entered STN: Dec. 6, 2011.
RN 1349623-68-2 Registry ED Entered STN: Dec. 6, 2011.
RN 1349668-73-0 Registry ED Entered STN: Dec. 6, 2011.
RN 1349887-30-4 Registry ED Entered STN: Dec. 6, 2011.
RN 1349985-90-5 Registry ED Entered STN: Dec. 7, 2011.
EP Application No. 22743177.2 Office Action and Search Report dated Sep. 5, 2025.
EP Application No. 22899358.0 Search Report dated Sep. 18, 2026.

* cited by examiner

CRYSTALLINE FORMS OF A PYRROLOPYRIDINE-ANILINE COMPOUND

CROSS-REFERENCES TO RELATED APPLICATIONS

This application claims priority to U.S. Provisional Application No. 63/139,975 filed Jan. 21, 2021, which is incorporated in its entity for all purposes.

BACKGROUND OF THE DISCLOSURE

Neurofibromatosis type 1 (NF1) occurs in approximately 1:3,500 births, and is one of the most common autosomal dominant single-gene disorders affecting neurological function in humans. Clinically, NF1 disease is characterized by the presence of benign peripheral nerve tumors, called neurofibromas, involving Schwann cells with biallelic mutations in the NF1 gene, as well as other tumor and non-tumor manifestations. See Jousma et al. Pediatr. Blood Cancer 62:1709-1716, 2015. NF1 is associated with several dermal disorders, including dermal neurofibromas; plexiform neurofibromas; café au lait spots; and axillary and inguinal freckling. Dermal neurofibromas occur in over 95% of NF1 patients, and can appear anywhere on the body, causing itching, irritation, infection, physical pain, and disfigurement. Moreover, dermal neurofibromas are associated with social isolation and anxiety.

NF1 is caused by one or more germ line mutations in NF1, a gene that inactivates the RAS pathway. Because the NF1 gene encodes a Ras-GAP protein, NF1 loss results in high Ras-GTP. Therefore, NF1 research has focused intensively on testing inhibitors in the Ras signaling pathway, including the Ras-MAPK cascade. See Jousma et al. Pediatr. Blood Cancer 62:1709-1716, 2015. Four distinct MAPK cascades have been identified and named according to their MAPK module. See Akinleye et al. Journal of Hematology & Oncology 6:27, 2013. MEK proteins belong to a family of enzymes that lie upstream to their specific MAPK targets in each of the four MAP kinase signaling pathways. Two of these MEK proteins, MEK1 and MEK2, are closely related and participate in this signaling pathway cascade. Inhibitors of MEK1 and MEK2 have been shown to effectively inhibit MEK signaling downstream of Ras, and thus provide a strong rationale for targeting MEK in the treatment of NF1. See Rice et al. Medicinal Chemistry Letters 3:416-421, 2012.

Currently available MEK inhibitors are designed to have oral bioavailability for systemic delivery, and are associated with significant side effects including decreased left ventricular ejection fraction, elevated creatine phosphokinase, pneumonitis, renal failure, diarrhea, infection, uticaria, and maculo-papular rash, all of which are dose limiting or require permanent discontinuation. Moreover, clinical trials have shown side effects with prolonged high-dose administration of MEK inhibitors. See Huang et al. J. Ocul. Pharmacol. Ther. 25:519-530, 2009. For example, PD0325901, a MEK inhibitor currently in clinical trials, has exhibited neurological side effects associated with ataxia, confusion, and syncope. In addition, a number of other side effects have been observed with systemic exposure to MEK inhibitors including: acneiform rash, CPK elevation, nausea, vomiting, diarrhea, abdominal pain, and fatigue. Thus, there is a need for therapies that inhibit MEK to treat NF1 associated dermal neurofibromas, which limit these serious side effects.

Benign cutaneous tumors of the vascular, keratinocytic, and melanocytic compartments often occur at birth or during childhood. These lesions, referred in this application as "birthmarks", can cause cosmetic distress, disfigurement and social anxiety. In some cases, these lesions can predispose individuals to functional impairment or future malignancies. These birthmarks can be sporadic or arise as part of an underlying neurocutaneous syndrome.

Vascular birthmarks include, for example port wine stain/capillary malformation, angiomas, lobular capillary hemangiomas, arteriovascular malformation, lymphatic malformation, vascular malformation, hemangiomas, and other angioma. Keratinocytic nevi refers to Keratinocytic epidermal nevi and nevi sebacei. Melanocytic nevi (commonly known as moles) include, for example congenital nevi, multiple lentigines (which can occur in syndromes such as LEOPARD), ephiledes (freckles), and nevus spiilus.

Neurocutaneous syndromes, also referred to as birthmarks, such as port-wine stains, are associated with congenital low-flow vascular malformations (capillary malformation) in the skin which, if left untreated, can hypertrophy and develop nodularity (Minkis, K. et al, *Lasers Surg Med.* (2009) 41 (6): pp 423-426). Laser therapy is typically used for treatment of port-wine stains, but often without full resolution. Epidermal nevi are common cutaneous mosaic disorders, subdivided into keratinocytic and organoid nevi. Organoid nevi include nevus sebaceus (NS). Immunolabelling of NS is reportedly associated with increased phosphorylated ERK staining (Aslam, A, et al., *Clinical and Experimental Dermatology* (2014) 39: pp 1-6). Non-organoid keratinocytic epidermal nevus (KEN) is characterized by benign congenital hyperpigmented skin lesions. Epidermal nevi with localized epidermal thickening are present at birth or become visible during childhood. Other cutaneous disorders that also occur in childhood birthmarks include nevus cellular nevus, lobulary capillary hemangioma, congenital nevi, ephiledes (freckles), multiple lentigines (which can occur in multiple syndromes including LEOPARD syndrome), capillary angioma, nevus spilus, arterio-venous malformations, lymphatic malformations, and congenital melanocytic nevus. Lentigines can occur in childhood (in syndromes such as LEOPARD syndrome), which has mutations that activate RAS/MAPK pathway, as well as can be acquired in adults. In some cases birthmarks are not amenable to surgical excision and/or laser treatment. In some cases birthmarks, when untreated, can progress to lesions and/or proliferative skin conditions.

Modulation of ERK/MEK pathways may have a therapeutic effect on birthmarks. RAS mutations have been reported in mosaic RASopathies i.e. non-organoid KEN, and sebaceous nevus (Farschtschi S, et al., *BMC Medical Genetics*. (2015); 16: pp 6; and Sun, B. K. et. Al, Journal of Investigative Dermatology, (2013); 3: pp 824-827). Thus, inhibition of Ras signaling pathway, including the Ras-MAPK cascade, may be useful in treating birthmarks.

Four distinct MAPK cascades have been identified and named according to their MAPK module. See Akinleye et al. *Journal of Hematology & Oncology* 6:27, 2013. MEK proteins belong to a family of enzymes that lie upstream to their specific MAPK targets in each of the four MAP kinase signaling pathways. Two of these MEK proteins, MEK1 and MEK2, are closely related and participate in this signaling pathway cascade. Inhibitors of MEK1 and MEK2 have been shown to effectively inhibit MEK signaling downstream of Ras (Rice et al. *Medicinal Chemistry Letters* 3:416-421, 2012), and thus provide a rationale for targeting MEK in the treatment of birthmarks.

Currently available MEK pathway inhibitors are designed to have oral bioavailability for systemic delivery, but are associated with one or more significant side effects including decreased left ventricular ejection fraction, elevated creatine phosphokinase, pneumonitis, renal failure, diarrhea, infection, uticaria, and maculo-papular rash, all of which are dose limiting or require permanent discontinuation. Moreover, clinical trials have shown one or more side effects with prolonged high-dose administration of MEK inhibitors. (Huang et al. *J. Ocul. Pharmacol. Ther.* 25:519-530, 2009). For example, PD0325901, a clinically-tested MEK inhibitor, has exhibited one or more neurological side effects associated with ataxia, confusion, and syncope. In addition, a number of other side effects have been observed with systemic exposure to MEK inhibitors including: acneiform rash, CPK elevation, nausea, vomiting, diarrhea, abdominal pain, and fatigue. Thus, there is a need for therapies that treat birthmarks and also limit one or more side effects associated with systemic exposure to MEK/ERK pathway inhibitors.

A compound of formula (I) was first disclosed in WO 2018/213810 as a MEK inhibitor for the treatment of dermal diseases or dermal disorders associated therewith. However, a crystalline form of the compound of formula (I) is not known. Therefore, there is a need to development a stable crystalline form of the compound that can be stored as an active pharmaceutical ingredient (API) in the development of a drug product for the treatment of skin disorders such as MEK-inhibitor responsive dermal disorders or MEK-mediated dermal disorders, and birthmarks.

BRIEF SUMMARY OF THE DISCLOSURE

In a first aspect, the present disclosure provides a crystalline form of a compound having formula (I):

(I)

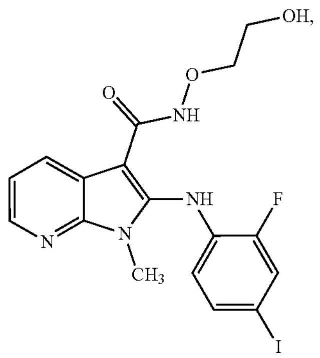

wherein the crystalline form is any one of crystalline Forms A, B, C, E, F, and H, each of which is characterized by an X-ray powder diffraction (XRPD) pattern as described herein.

In some embodiments, the present disclosure provides crystalline Form A of the compound of formula (I), characterized by an X-ray powder diffraction (XRPD) pattern 5 including peaks at 5.3, 8.0, 18.3, 18.5, and 24.3 degrees 2θ (±0.2 degrees 2θ).

In a second aspect, the present disclosure provides a pharmaceutical composition prepared by a method including combining a crystalline form of the compound of formula (I) with one or more pharmaceutically acceptable carriers, wherein the crystalline form is any one of crystalline Forms A, B, C, E, F, and H, each of which is as defined and described herein. In some embodiments, the present disclosure provides a pharmaceutical composition prepared by a method including combining crystalline Form A of the compound of formula (I) with one or more pharmaceutically acceptable excipients, wherein the crystalline Form A is as defined and described herein.

In a third aspect, the present disclosure provides a method of treating a skin disorder. The method includes administering a crystalline form of the compound of formula (I) or a pharmaceutical composition thereof, thereby treating the skin disease, wherein the crystalline form is any one of crystalline Forms A, B, C, E, F, and H, each of which is as defined and described herein; and the pharmaceutical composition is as defined and described herein. In some embodiments, the present disclosure provides a method of treating a skin disorder, including administering crystalline Form A of the compound of formula (I) or a pharmaceutical composition thereof, wherein the crystalline Form A and the pharmaceutical composition are each as defined and described herein.

In a fourth aspect, the present disclosure provides a method for preparing crystalline Form A as described herein, including:

a) forming a first mixture including the compound of formula (I) and tetrahydrofuran (THF) at a first temperature of from about 50° C. to about 65° C.;
b) cooling the first mixture to a second temperature of from about 35° C. to about 45° C.;
c) adding one or more seeds of the crystalline Form A prior to step d) to form a second mixture or during step d);
d) adding methyl-tertiary-butyl ether (MTBE) to form a third mixture;
e) cooling the third mixture to a third temperature of no more than about 25° C. to form a fourth mixture comprising a precipitate; and
f) isolating the precipitate from the fourth mixture to provide the crystalline Form A, wherein steps c) and d) are each maintained at the second temperature.

In a fifth aspect, the present disclosure provides a method for preparing crystalline Form A as described herein, including:

a) forming a third slurry comprising the compound having formula (I), tetrahydrofuran (THF), and methyl-tertiary-butyl ether (MTBE);
b) adding one or more seeds of the crystalline Form A to form a fourth slurry;
c) stirring the fourth slurry to form a fifth slurry; and
d) isolating a precipitate from the fifth slurry to provide the crystalline Form A, wherein the one or more seeds of the crystalline Form A are in an amount of at least about 5% by weight of the compound of formula (I); and steps a) to c) are each maintained at a temperature of from about 40° C. to about 50° C.

BRIEF DESCRIPTION OF THE DRAWINGS

FIG. 15A shows a full spectrum and FIG. 15B shows an expanded aromatic region.

DETAILED DESCRIPTION OF THE DISCLOSURE

I. General

Figure 1:
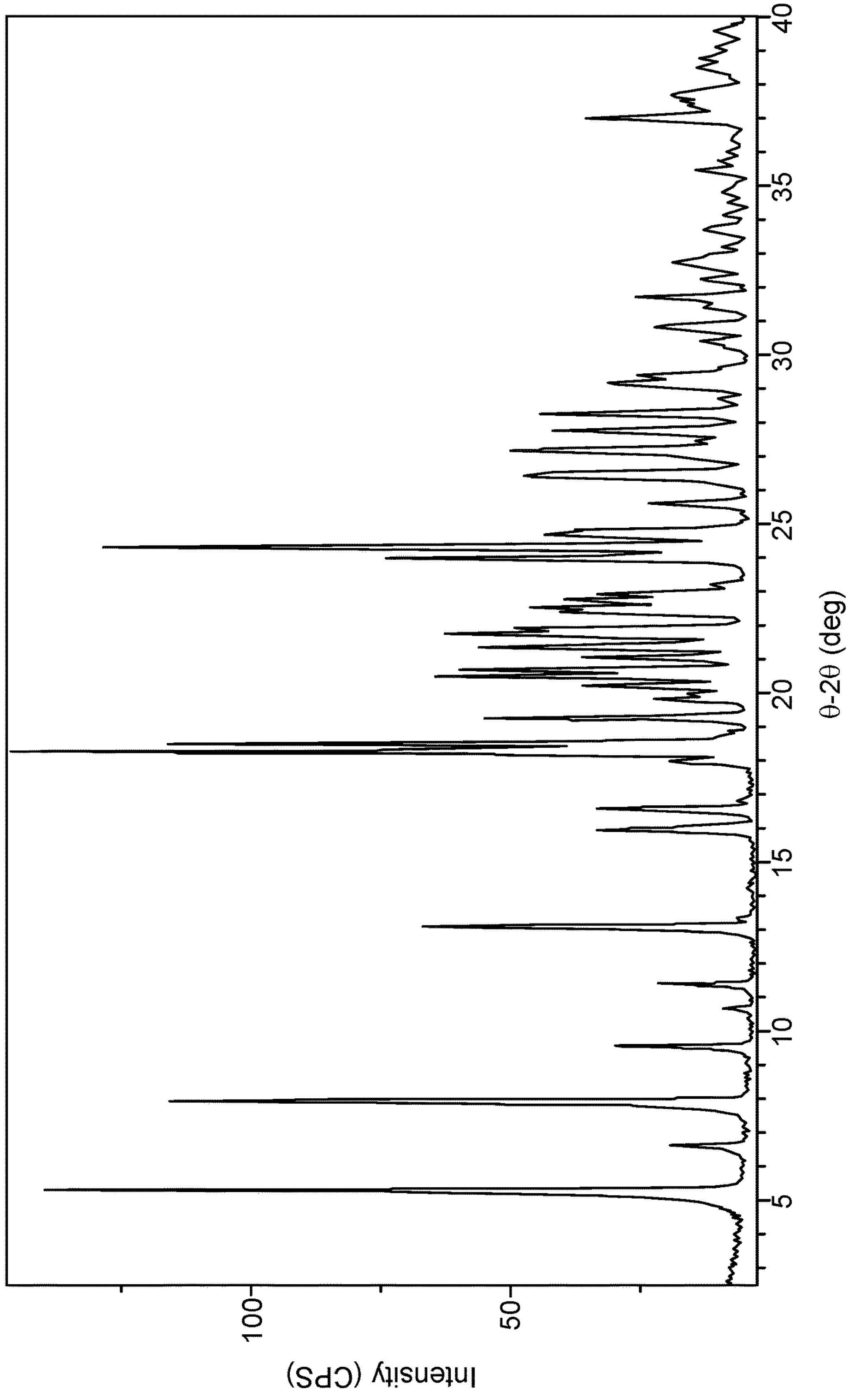
FIG. 1 shows X-ray powder diffraction (XRPD) patterns for crystalline Form A.

The present disclosure provides crystalline forms of the compound having formula (I), wherein the crystalline forms are crystalline Forms A, B, C, E, F, and H. The crystalline Forms A, B, C, E, F, and H are each characterized by an X-ray powder diffraction (XRPD) pattern. Selected crystalline forms are further characterized by a differential scanning calorimetry (DSC), a thermal gravimetric analysis (TGA), a dynamic vapor sorption (DVS) cycle, and/or a water content by a Karl Fischer (KF) method. The present disclosure also provides methods for preparing crystalline forms, in particular Form A. The present disclosure further provides methods of treating various skin disorders using the crystalline forms (e.g., Form A) of the disclosure or a pharmaceutical composition thereof.

II. Definitions

"Substantially free" refers to an amount of 10% or less of another form or impurity, preferably 8%, 5%, 4%, 3%, 2%, 1%, 0.5%, or less of another form or impurity.

"Crystalline form" refers to a solid form of a compound wherein the constituent molecules are packed in a regularly ordered, repeating pattern. A crystalline form can include triclinic, monoclinic, orthorhombic, tetragonal, trigonal, hexagonal, and cubic crystal geometries. A crystalline form can include one or more regions, i.e., grains, with distinct crystal boundaries. A crystalline solid can include two or more crystal geometries.

"Amorphous form" refers to a solid form of a compound having no definite crystal structure, i.e., lacking a regularly ordered, repeating pattern of constituent molecules.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Hydrate" refers to a compound that is complexed with a water molecule. The compounds of the present disclosure can be complexed with ½ water molecule or from 1 to 10 water molecules.

XRPD patterns can be indexed in the absence of suitable single crystals for structure elucidation [McClurg, Richard B.; Smit, Jared P. X-ray Powder Diffraction Pattern Indexing for Pharmaceutical Applications. *Pharm. Tech. Europe*, January 2013; and X'Pert High Score Plus 2.2a (2.2.1)]. Indexing is the process of determining the size and shape of the crystallographic unit cell given the peak positions in a diffraction pattern. The term gets its name from the assignment of Miller index labels to individual peaks. XRPD indexing serves several purposes. If all of the peaks in a pattern are indexed by a single unit cell, this is strong evidence that the sample contains a single crystalline phase. Given the indexing solution, the unit cell volume may be calculated directly. Indexing is also a robust description of a crystalline form and provides a concise summary of all available peak positions for that phase at a particular thermodynamic state point.

"Crude" refers to a mixture including a desired compound (e.g., the compound of formula (I)) and at least one other species (e.g., a solvent, a reagent such as an acid or base, a starting material, or a byproduct of a reaction giving rise to the desired compound).

Unless specifically indicated otherwise, "purity %" or "purity area %" (e.g., 95% or 95 area %) refers to a purity of a compound (e.g., the compound of formula (I)) in the area under curve (AUC) determined by a HPLC or UPLC method (e.g., Chemical Development HPLC Method or UPLC method as described herein).

"First mixture", "second mixture", and so on refer to a mixture as described in embodiments of the present disclosure. The mixture naming conventions are used solely for the purpose of clarity in steps of the process as described herein and they are not required to be in a numerical order. Some mixtures may be absent in selected embodiments of the present disclosure as described herein. One skilled in the art will understand the meaning of these mixture naming conventions (e.g., 'first mixture', 'second mixture') within the context of the term's use in the embodiments and claims herein.

"First slurry", "second slurry", and so on refer to a slurry as described in embodiments of the present disclosure. The slurry naming conventions are used solely for the purpose of clarity in steps of the process as described herein and they are not required to be in a numerical order. Some slurries may be absent in selected embodiments of the present disclosure as described herein. One skilled in the art will understand the meaning of these slurry naming conventions (e.g., 'first slurry', 'second slurry') within the context of the term's use in the embodiments and claims herein.

"First temperature", "second temperature", and so on refer to a temperature as described in embodiments of the present disclosure. The temperature naming conventions are used solely for the purpose of clarity in steps of the process as described herein and they are not required to be in a numerical order. One skilled in the art will understand the meaning of these temperature naming conventions (e.g., 'first temperature', 'second temperature') within the context of the term's use in the embodiments and claims herein.

"Alkyl alcohol" refers to an alkyl group having a hydroxy group attached to a carbon of the chain, wherein the alkyl group is defined as a straight or branched, saturated, aliphatic radical having the number of carbon atoms indicated (i.e., $C_{1-4}$ means one to four carbons). For example, $C_{1-4}$ alkyl alcohol includes methanol, ethanol, n-propanol, isopropanol, n-butanol, sec-butanol, isobutanol, and tert-butanol. Alkyl alcohols useful in the present disclosure are fully saturated. One of skill in the art will appreciate that other alcohols are useful in the present disclosure.

"Precipitating" refers to the process of causing a compound in a solution to coalesce into a solid form of the substance (i.e., a precipitate). The entirety of a compound in a solution, or any fraction thereof, can be caused to precipitate. The solid form of the substance can be amorphous or crystalline.

"Isolating" refers to the process of isolating at least a portion of a first substance (e.g., a precipitate) from a mixture including the substance and at least one additional substance. In some instances, the isolated substance is substantially free at least one of the additional substances present in the original mixture.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

"Pharmaceutically acceptable excipient" refers to a substance that aids the administration of an active agent to and absorption by a subject. Pharmaceutical excipients useful in the present disclosure include, but are not limited to, binders, fillers, disintegrants, lubricants, coatings, sweeteners, flavors and colors. Pharmaceutical excipients useful in the present disclosure for transdermal/topical delivery include, but are not limited to, enhancers, solubilizers, antioxidants, plastisizers, thickeners, polymers, and pressure sensitive adhesives. One of skill in the art will recognize that other pharmaceutical excipients are useful in the present disclosure.

"Inhibition", "inhibits" and "inhibitor" refer to a compound that prohibits or a method of prohibiting, a specific action or function.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, the patient is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"About" means a range of values including the specified value, which a person of ordinary skill in the art would consider reasonably similar to the specified value. In some embodiments, the term "about" means within a standard deviation using measurements generally acceptable in the art. In some embodiments, "about" means a range extending to +/−10% of the specified value. In some embodiments, "about" means the specified value.

III. CRYSTALLINE FORMS

In a first aspect, the present disclosure provides a crystalline form of a compound having formula (I):

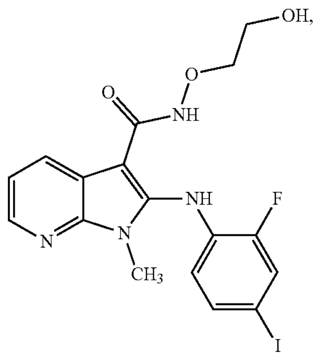

(I)

wherein the crystalline form is any one of crystalline Forms A, B, C, E, F, and H, each of which is characterized by an X-ray powder diffraction (XRPD) pattern as described herein.

Methods for collection of XRPD data are known in the art, and any such methods can be used for characterizing the crystalline forms of the compound of formula (I). For example, the X-ray powder diffraction patterns described herein can be generated using Cu Kα1 radiation.

In some embodiments, the crystalline form described herein is further characterized by a differential scanning calorimetry (DSC) thermogram. In some embodiments, a DSC thermogram is recorded using a sample weight of about 1-2 mg, which is subjected to temperatures ranging from 30° C. to 350° C. using a ramp of 10° C./min.

In some embodiments, the crystalline form described herein is further characterized by a thermal gravimetric analysis (TGA). In some embodiments, a TGA thermogram is recorded using a sample weight of about 2-10 mg, which is subjected to temperatures ranging from 30° C. to 300° C. using a ramp of 10° C./min.

In some embodiments, the crystalline form described herein is further characterized by a water content, as measured by a Karl Fischer (KF) method.

In some embodiments, the crystalline form described herein is further characterized by a Nuclear Magnetic Resonance spectrum, such as a 1H NMR spectrum. In some embodiments, the 1H NMR is recorded on Bruker Avance-AV 400 MHz with a probe of 5 mm PABBO BB-1H/D.

III-1. Crystalline Form A

In one embodiment, the present disclosure provides crystalline Form A of a compound having formula (I), characterized by an X-ray powder diffraction (XRPD) pattern including peaks at 5.3, 8.0, 18.3, 18.5, and 24.3 degrees 2θ (±0.2 degrees 2θ). In some embodiments, the X-ray powder diffraction pattern further comprises peaks at 13.1, 20.5, 20.7, 21.7, and 24.0 degrees 2θ (±0.2 degrees 2θ). In some embodiments, the X-ray powder diffraction pattern further comprises peaks at 9.6, 16.0, 16.6, 19.3, and 21.4 degrees 2θ (±0.2 degrees 2θ). In some embodiments, crystalline Form A is characterized by an X-ray powder diffraction (XRPD) pattern including peaks (i.e., the first 10 peaks ranked according to relative peak intensity %) at 5.3, 8.0, 13.1, 18.3, 18.5, 20.5, 20.7, 21.7, 24.0, and 24.3 degrees 2θ (±0.2 degrees 2θ). In some embodiments, crystalline Form A is characterized by an X-ray powder diffraction (XRPD) pattern including three, four, five or more peaks listed in Table 2A or Table 2B. In some embodiments, crystalline Form A is characterized by an X-ray powder diffraction (XRPD) pattern including at least five peaks listed in Table 2A or Table 2B.

In some embodiments, crystalline Form A of a compound having formula (I), is characterized by an X-ray powder diffraction pattern substantially in accordance with FIG. 1.

In some embodiments, crystalline Form A is substantially free of other crystalline or amorphous forms of the compound having formula (I).

In some embodiments, crystalline Form A is further characterized by a differential scanning calorimetry (DSC) thermogram including an endothermic peak at about 189.9° C. In some embodiments, crystalline Form A is further characterized by a differential scanning calorimetry (DSC) thermogram including an onset temperature of about 187.1° C. and an endothermic peak at about 189.9° C.

Figure 2:
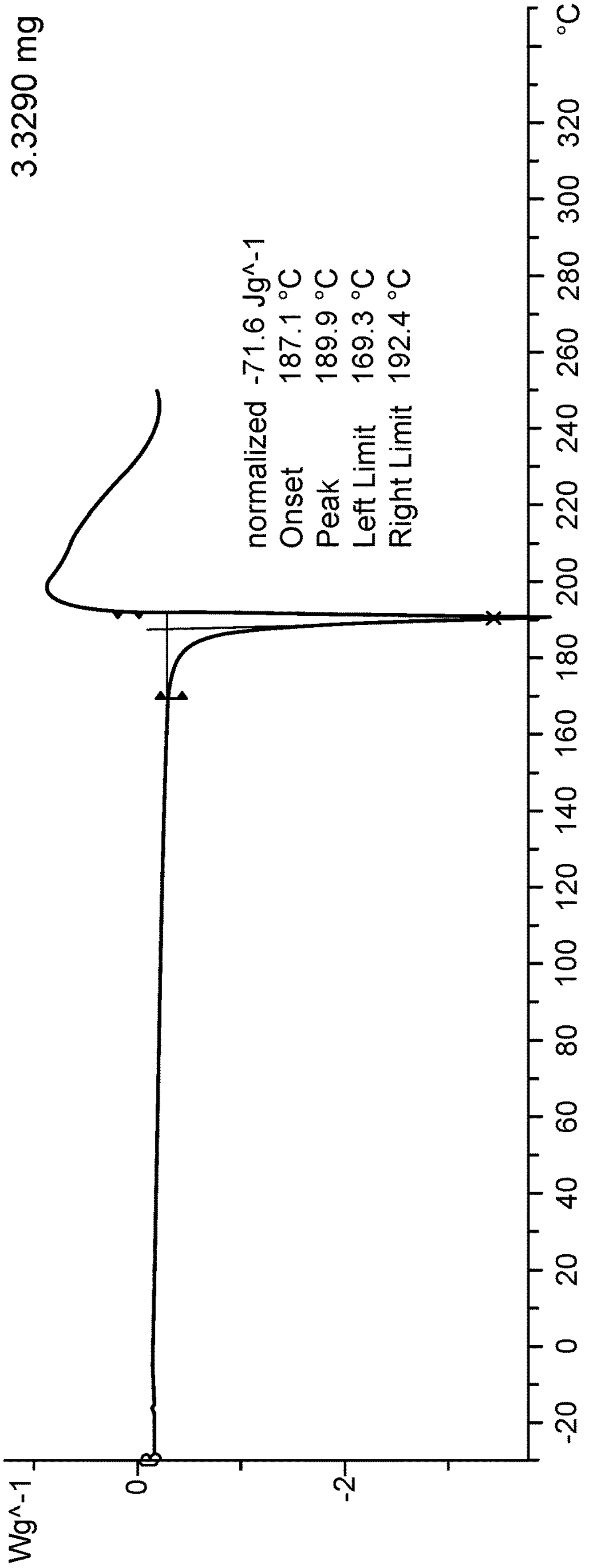
FIG. 2 shows differential scanning calorimetry (DSC) thermograms for crystalline Form A.

In some embodiments, crystalline Form A is further characterized by a differential scanning calorimetry (DSC) thermogram substantially in accordance with FIG. 2.

In some embodiments, crystalline Form A is further characterized by a weight loss of from about 0.1% to about 1% upon heating to about 100° C., as measured by a thermal gravimetric analysis (TGA). In some embodiments, crystalline Form A is further characterized by a weight loss of about 0.3% upon heating from about 50° C. to about 100° C., as measured by a thermal gravimetric analysis (TGA).

Figure 3:
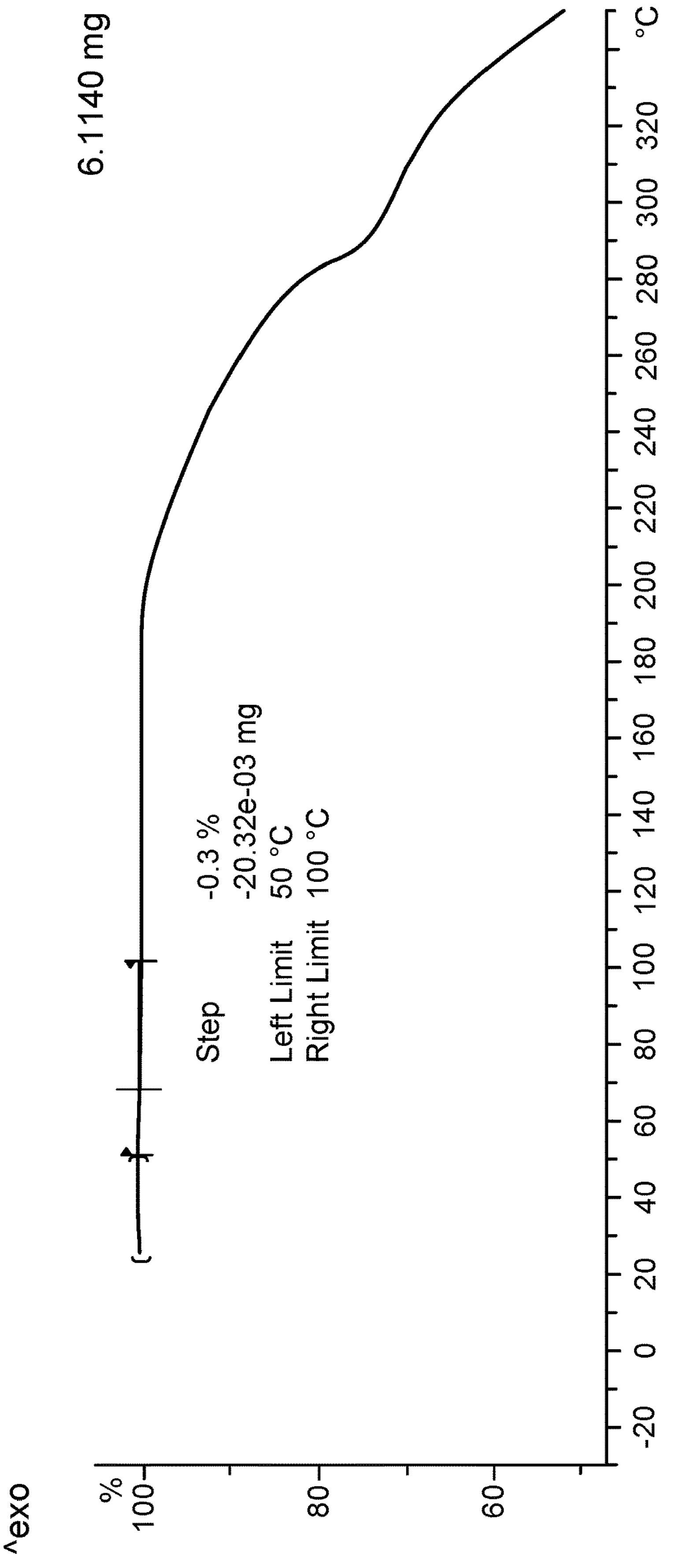
FIG. 3 shows thermal gravimetric analysis (TGA) thermograms for crystalline Form A.

In some embodiments, crystalline Form A is further characterized by a thermal gravimetric analysis (TGA) thermogram substantially in accordance with FIG. 3.

In some embodiments, crystalline Form A is further characterized by a weight gain of about 1.1% after undergoing a dynamic vapor sorption cycle from about 5% relative humidity (RH) to about 95% RH at 25° C. In some embodiments, crystalline Form A is further characterized by a weight loss of about 1.2% after undergoing a dynamic vapor desorption cycle from about 95% relative humidity (RH) to about 5% RH at 25° C. In some embodiments, crystalline Form A is further characterized by a weight gain of about 1.1% after undergoing a dynamic vapor sorption cycle from about 5% relative humidity (RH) to about 95% RH at 25° C.; and further characterized by a weight loss of about 1.2% after undergoing a dynamic vapor desorption cycle from about 95% relative humidity (RH) to about 5% RH at 25° C.

Figure 4:
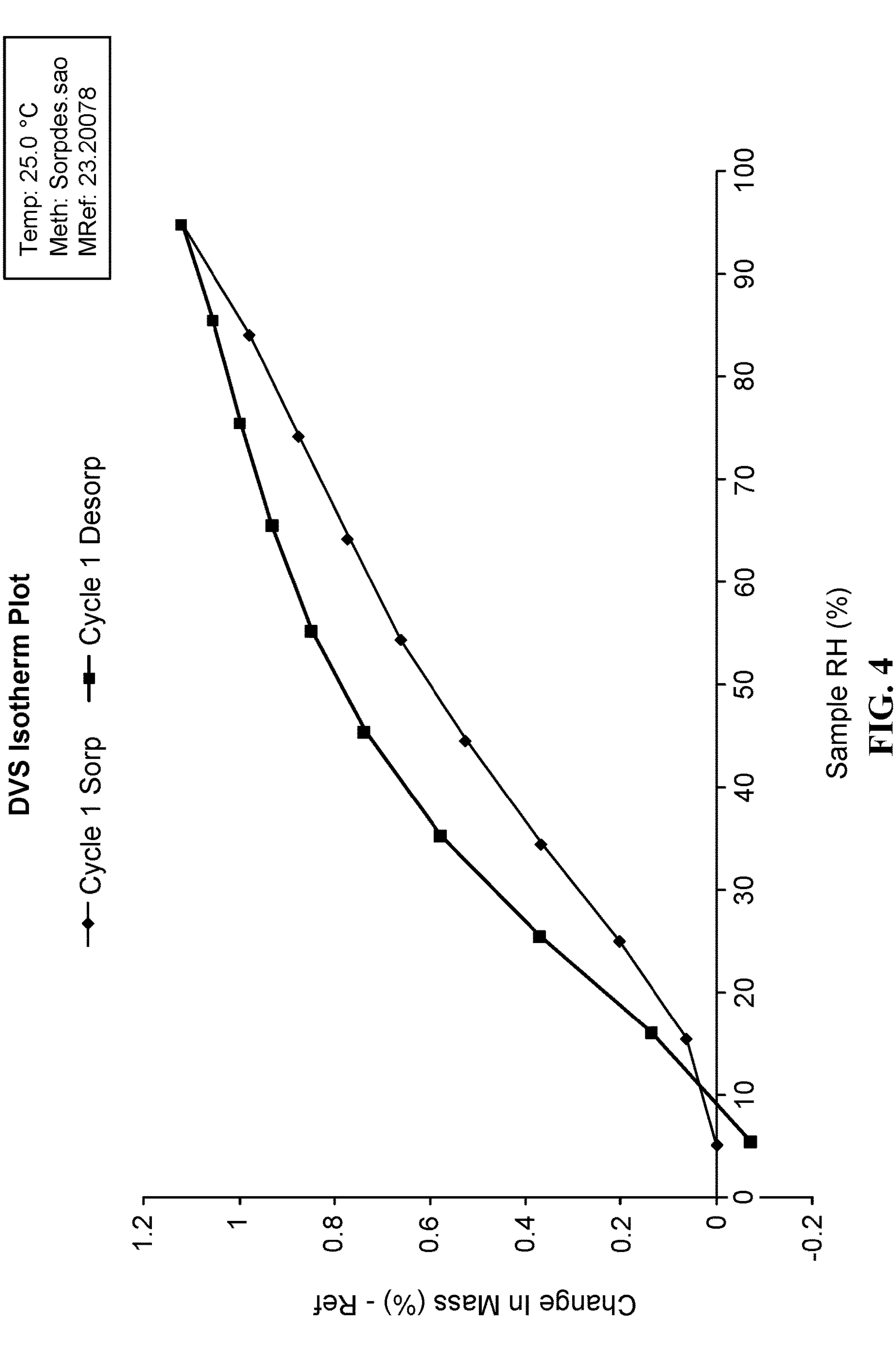
FIG. 4 shows a dynamic vapor sorption (DVS) cycle of crystalline Form A.

In some embodiments, crystalline Form A is further characterized by a dynamic vapor sorption profile substantially in accordance with FIG. 4.

In some embodiments, crystalline Form A is further characterized by a water content of from about 0.1% to about 0.5% by weight, as measured by a Karl Fischer (KF) method. In some embodiments, crystalline Form A is further characterized by a water content of about 0.35% by weight, as measured by a Karl Fischer (KF) method.

In some embodiments, crystalline Form A is in an anhydrous form. In some embodiments, crystalline Form A is in an anhydrous form, wherein a water content is from about 0.1% to about 0.5% by weight, as measured by a Karl Fischer (KF) method. In some embodiments, crystalline Form A is in an anhydrous form, wherein a water content is about 0.35% by weight, as measured by a Karl Fischer (KF) method.

In some embodiments, crystalline Form A is characterized by an X-ray powder diffraction pattern substantially in accordance with FIG. 1; and is further characterized by a differential scanning calorimetry (DSC) thermogram substantially in accordance with FIG. 2. In some embodiments, crystalline Form A is characterized by an X-ray powder diffraction pattern substantially in accordance with FIG. 1; is further characterized by a differential scanning calorimetry (DSC) thermogram substantially in accordance with FIG. 2; and is further characterized by a thermal gravimetric analysis (TGA) thermogram substantially in accordance with FIG. 3. In some embodiments, crystalline Form A is characterized by an X-ray powder diffraction pattern substantially in accordance with FIG. 1; is further characterized by a differential scanning calorimetry (DSC) thermogram substantially in accordance with FIG. 2; is further characterized by a thermal gravimetric analysis (TGA) thermogram substantially in accordance with FIG. 3; and is further characterized by a dynamic vapor sorption profile substantially in accordance with FIG. 4. In some embodiments, crystalline Form A is characterized by an X-ray powder diffraction pattern substantially in accordance with FIG. 1; is further characterized by a differential scanning calorimetry (DSC) thermogram substantially in accordance with FIG. 2; is further characterized by a thermal gravimetric analysis (TGA) thermogram substantially in accordance with FIG. 3; and is further characterized by a water content of from about 0.1% to about 0.5% by weight, as measured by a Karl Fischer (KF) method.

III-2. Crystalline Form E

In one embodiment, the present disclosure provides crystalline Form E of a compound having formula (I), characterized by an X-ray powder diffraction (XRPD) pattern including peaks at 18.0, 18.3, 20.1, 20.4, and 23.5 degrees 2θ (±0.2 degrees 2θ). In some embodiments, the X-ray powder diffraction pattern further comprises peaks at 7.3, 15.1, 21.2, 22.8, and 24.4 degrees 2θ (±0.2 degrees 2θ). In some embodiments, the X-ray powder diffraction pattern further comprises peaks at 18.5, 21.9, 24.6, and 25.8 degrees 2θ (±0.2 degrees 2θ). In some embodiments, crystalline Form E is characterized by an X-ray powder diffraction (XRPD) pattern including peaks (i.e., the first 10 peaks ranked according to relative peak intensity %) at 7.3, 15.1, 18.0, 18.3, 20.1, 20.4, 21.2, 22.8, 23.5, and 24.4 degrees 2θ (±0.2 degrees 2θ). In some embodiments, crystalline Form E is characterized by an X-ray powder diffraction (XRPD) pattern including three, four, five or more peaks listed in Table 4A or Table 4B. In some embodiments, crystalline Form E is characterized by an X-ray powder diffraction (XRPD) pattern including at least five peaks listed in Table 4A or Table 4B.

Figure 5:
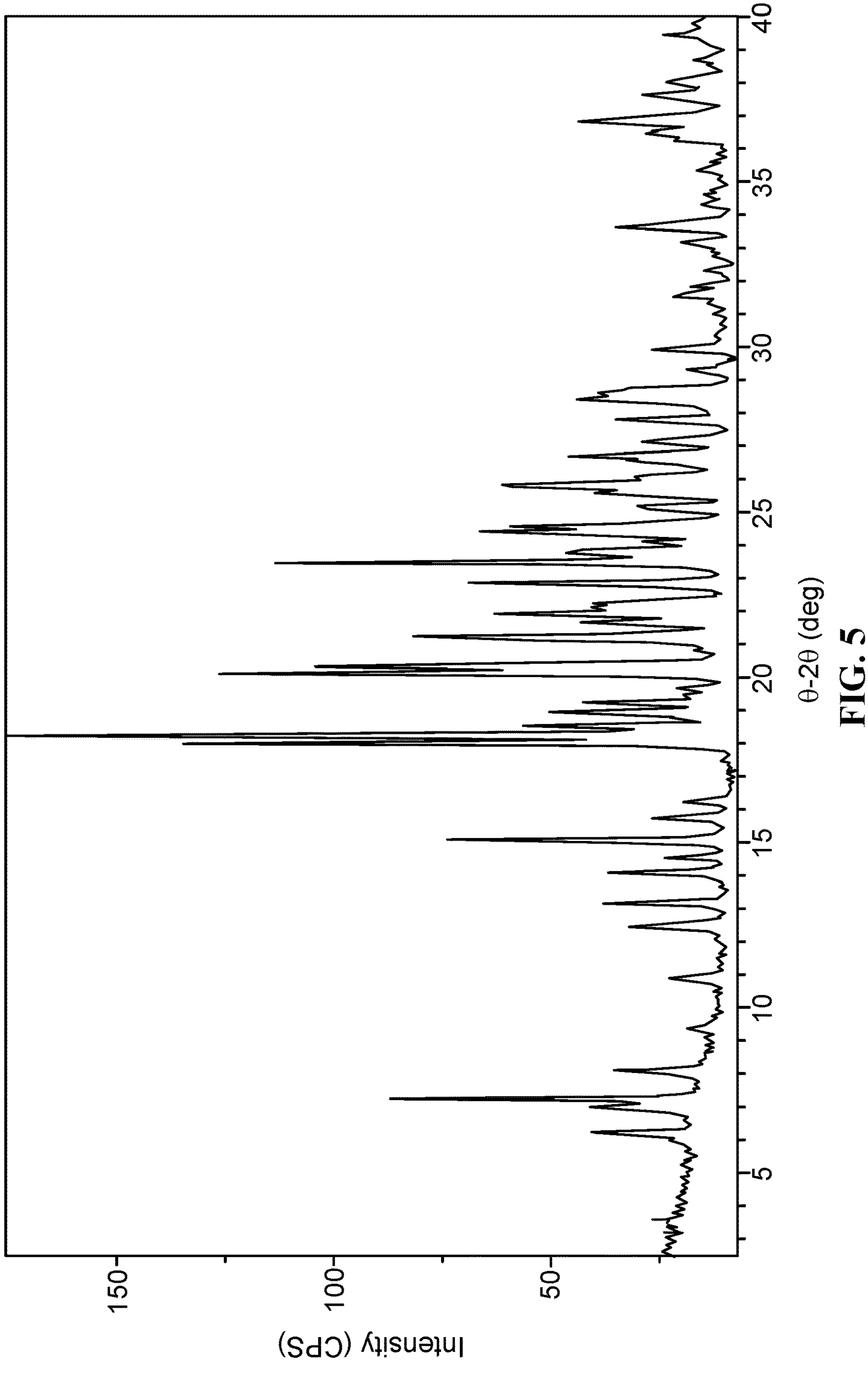
FIG. 5 shows an X-ray powder diffraction (XRPD) pattern of crystalline Form E.

In some embodiments, crystalline Form E of a compound having formula (I), is characterized by an X-ray powder diffraction pattern substantially in accordance with FIG. 5.

In some embodiments, crystalline Form E is substantially free of other crystalline or amorphous forms of the compound having formula (I).

In some embodiments, crystalline Form E is further characterized by a differential scanning calorimetry (DSC) thermogram including an endothermic peak at about 190.2° C. In some embodiments, crystalline Form E is further characterized by a differential scanning calorimetry (DSC) thermogram including an onset temperature of about 188.0° C. and an endothermic peak at about 190.2° C.

Figure 6:
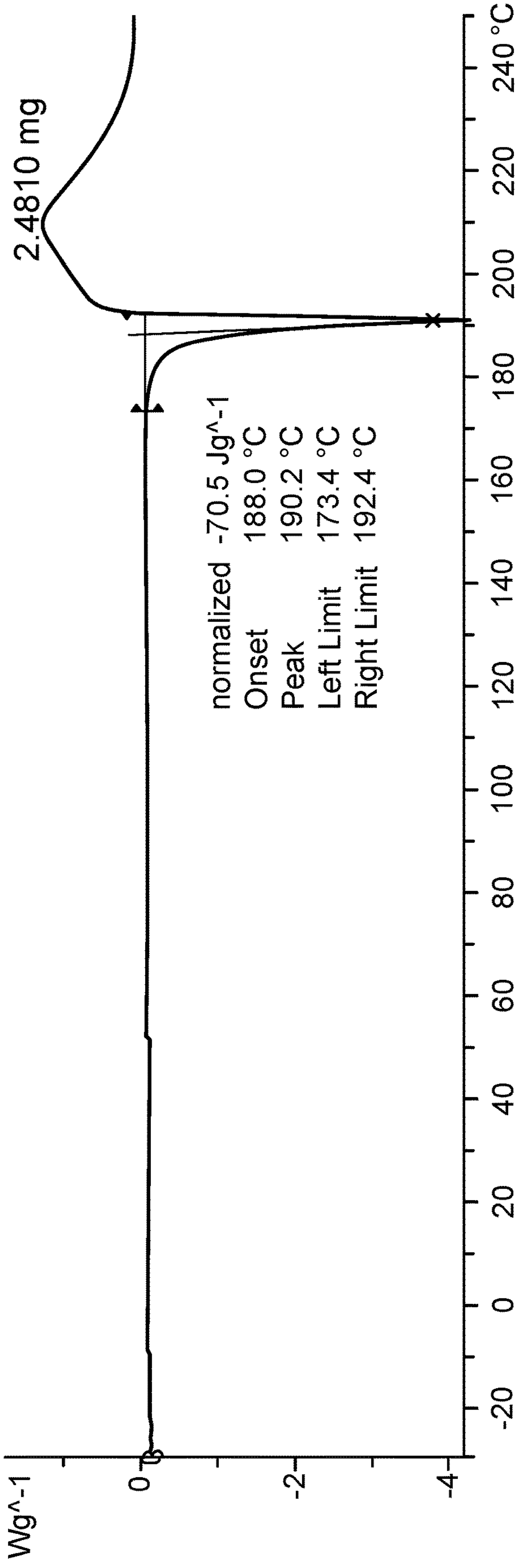
FIG. 6 shows a differential scanning calorimetry (DSC) thermogram of crystalline Form E.

In some embodiments, crystalline Form E is further characterized by a differential scanning calorimetry (DSC) thermogram substantially in accordance with FIG. 6.

In some embodiments, crystalline Form E is further characterized by a weight loss of about 0.3% upon heating from about 39° C. to about 180° C., as measured by a thermal gravimetric analysis (TGA).

Figure 7:
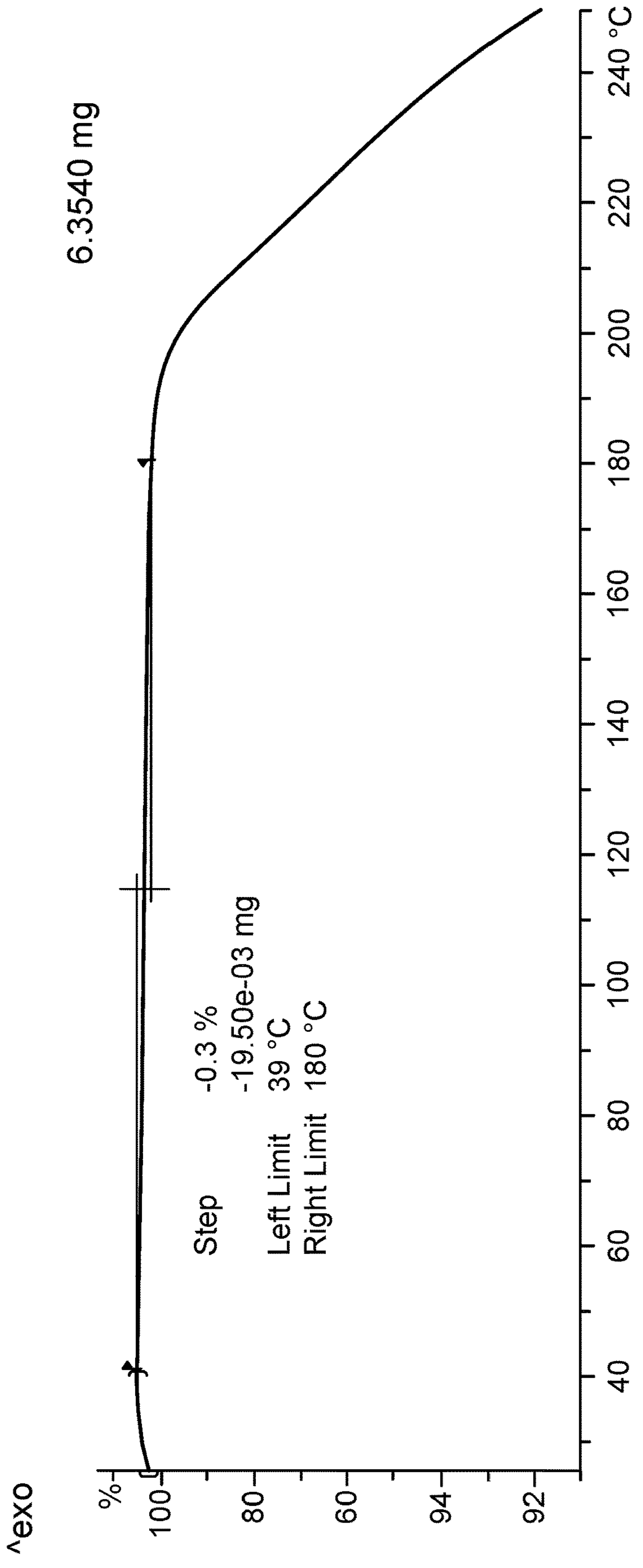
FIG. 7 shows a thermal gravimetric analysis (TGA) thermogram of crystalline Form E.

In some embodiments, crystalline Form E is further characterized by a thermal gravimetric analysis (TGA) thermogram substantially in accordance with FIG. 7.

In some embodiments, crystalline Form E is in an anhydrous form.

In some embodiments, crystalline Form E is characterized by an X-ray powder diffraction pattern substantially in accordance with FIG. 5; and is further characterized by a differential scanning calorimetry (DSC) thermogram substantially in accordance with FIG. 6. In some embodiments, crystalline Form E is characterized by an X-ray powder diffraction pattern substantially in accordance with FIG. 5; is further characterized by a differential scanning calorimetry (DSC) thermogram substantially in accordance with FIG. 6; and is further characterized by a thermal gravimetric analysis (TGA) thermogram substantially in accordance with FIG. 7.

III-3. Crystalline Form F

In one embodiment, the present disclosure provides crystalline Form F of a compound having formula (I), characterized by an X-ray powder diffraction (XRPD) pattern including peaks at 12.1, 17.8, 19.3, 22.1, and 23.3 degrees 2θ (±0.2 degrees 2θ). In some embodiments, the X-ray powder diffraction pattern further comprises peaks at 18.9, 19.2, 19.5, 21.1, and 22.4 degrees 2θ (±0.2 degrees 2θ). In some embodiments, crystalline Form F is characterized by an X-ray powder diffraction (XRPD) pattern including peaks (i.e., the first 10 peaks ranked according to relative peak intensity %) at 12.1, 17.8, 18.9, 19.2, 19.3, 19.5, 21.1, 22.1, 22.4, and 23.3 degrees 2θ (±0.2 degrees 2θ). In some embodiments, crystalline Form F is characterized by an X-ray powder diffraction (XRPD) pattern including one, two, three, four, five or more peaks listed in Table 6A or Table 6B. In some embodiments, crystalline Form F is characterized by an X-ray powder diffraction (XRPD) pattern including at least five peaks listed in Table 6A or Table 6B.

Figure 8:
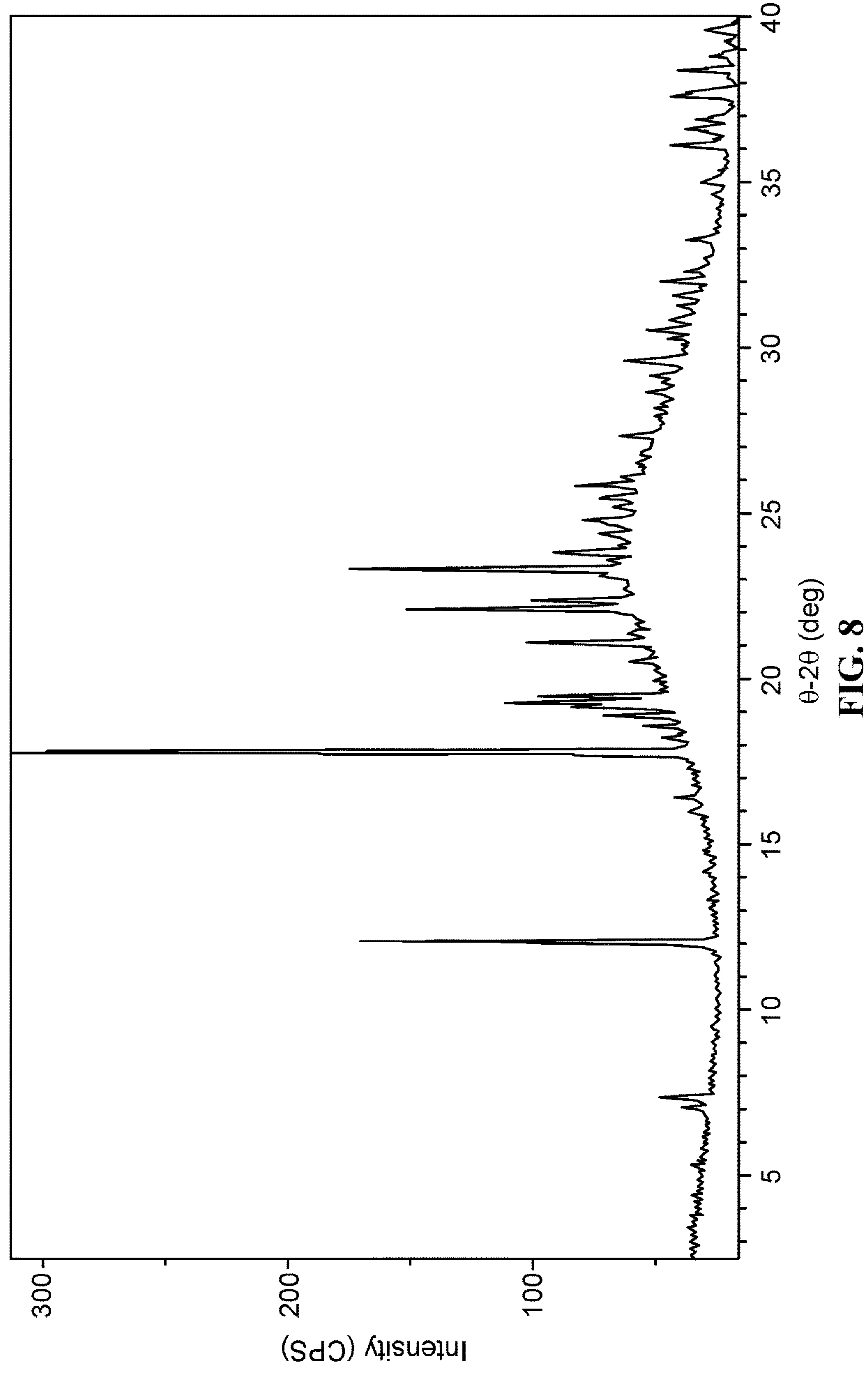
FIG. 8 shows an X-ray powder diffraction (XRPD) pattern of crystalline Form F.

In some embodiments, crystalline Form F of a compound having formula (I), is characterized by an X-ray powder diffraction pattern substantially in accordance with FIG. 8.

In some embodiments, crystalline Form F is substantially free of other crystalline or amorphous forms of the compound having formula (I).

In some embodiments, crystalline Form F is further characterized by a differential scanning calorimetry (DSC) thermogram including one or more endothermic peaks at about 162.7° C. and 187.5° C. In some embodiments, crystalline Form F is further characterized by a differential scanning calorimetry (DSC) thermogram including an onset temperature of about 158.9° C. and an endothermic peak at about 162.7° C. In some embodiments, crystalline Form F is further characterized by a differential scanning calorimetry (DSC) thermogram including an onset temperature of about 185.3° C. and an endothermic peak at about 187.5° C.

Figure 9:
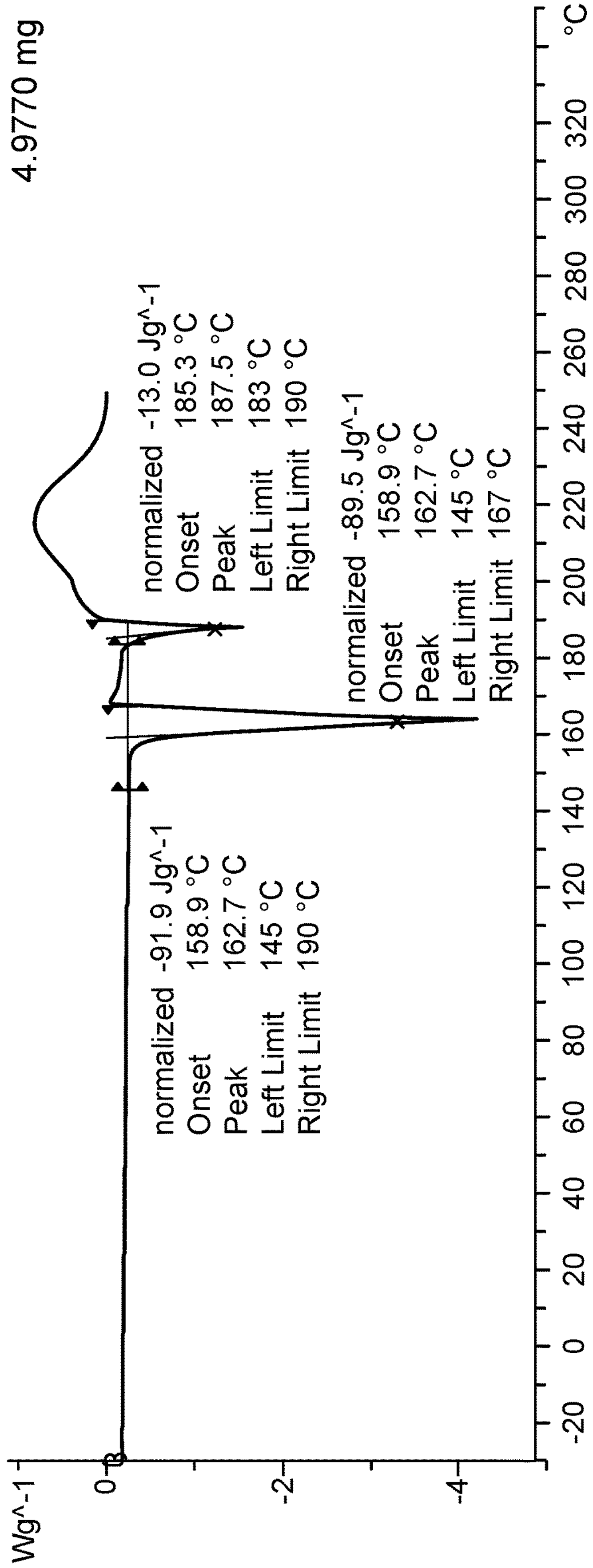
FIG. 9 shows a differential scanning calorimetry (DSC) thermogram of crystalline Form F.

In some embodiments, crystalline Form F is further characterized by a differential scanning calorimetry (DSC) thermogram substantially in accordance with FIG. 9.

In some embodiments, crystalline Form F is further characterized by a weight loss of about 0.4% upon heating from about 50° C. to about 180° C., as measured by a thermal gravimetric analysis (TGA).

Figure 10:
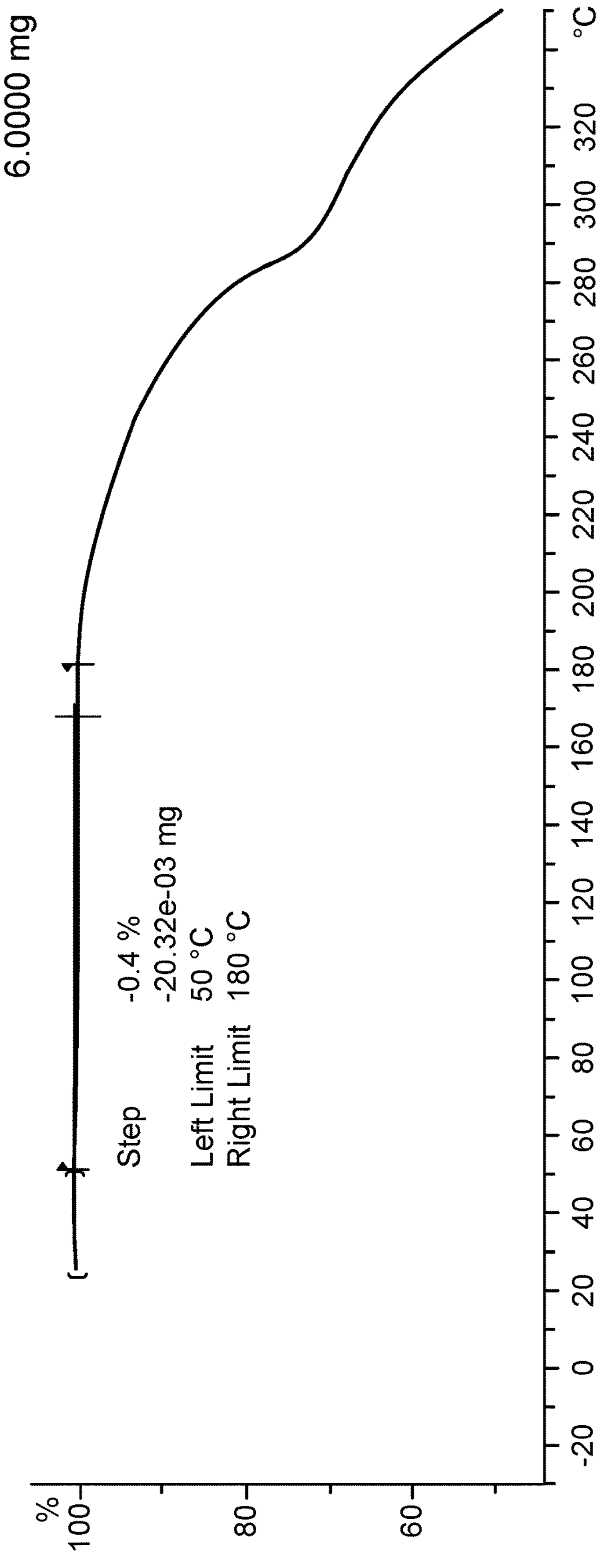
FIG. 10 shows a thermal gravimetric analysis (TGA) thermogram of crystalline Form F.

In some embodiments, crystalline Form F is further characterized by a thermal gravimetric analysis (TGA) thermogram substantially in accordance with FIG. 10.

In some embodiments, crystalline Form F is in an anhydrous form.

In some embodiments, crystalline Form F is characterized by an X-ray powder diffraction pattern substantially in accordance with FIG. 8; and is further characterized by a differential scanning calorimetry (DSC) thermogram substantially in accordance with FIG. 9. In some embodiments, crystalline Form F is characterized by an X-ray powder diffraction pattern substantially in accordance with FIG. 8; is further characterized by a differential scanning calorimetry (DSC) thermogram substantially in accordance with FIG. 9; and is further characterized by a thermal gravimetric analysis (TGA) thermogram substantially in accordance with FIG. 10.

III-4. Crystalline Form B

In one embodiment, the present disclosure provides crystalline Form B of a compound having formula (I), characterized by an X-ray powder diffraction (XRPD) pattern including peaks at 5.1, 15.1, 17.3, 17.8, and 23.8 degrees 2θ (±0.2 degrees 2θ). In some embodiments, the X-ray powder diffraction pattern further comprises peaks at 14.8, 16.5, 20.8, 25.0, and 28.5 degrees 2θ (±0.2 degrees 2θ). In some embodiments, crystalline Form B is characterized by an X-ray powder diffraction (XRPD) pattern including peaks (i.e., the first 10 peaks ranked according to relative peak intensity %) at 5.1, 14.8, 15.1, 16.5, 17.3, 17.8, 20.8, 23.8, 25.0, and 28.5 degrees 2θ (±0.2 degrees 2θ). In some embodiments, crystalline Form B is characterized by an X-ray powder diffraction (XRPD) pattern including three, four, five or more peaks listed in Table 8A or Table 8B. In some embodiments, crystalline Form B is characterized by an X-ray powder diffraction (XRPD) pattern including at least five peaks listed in Table 8A or Table 8B.

Figure 11:
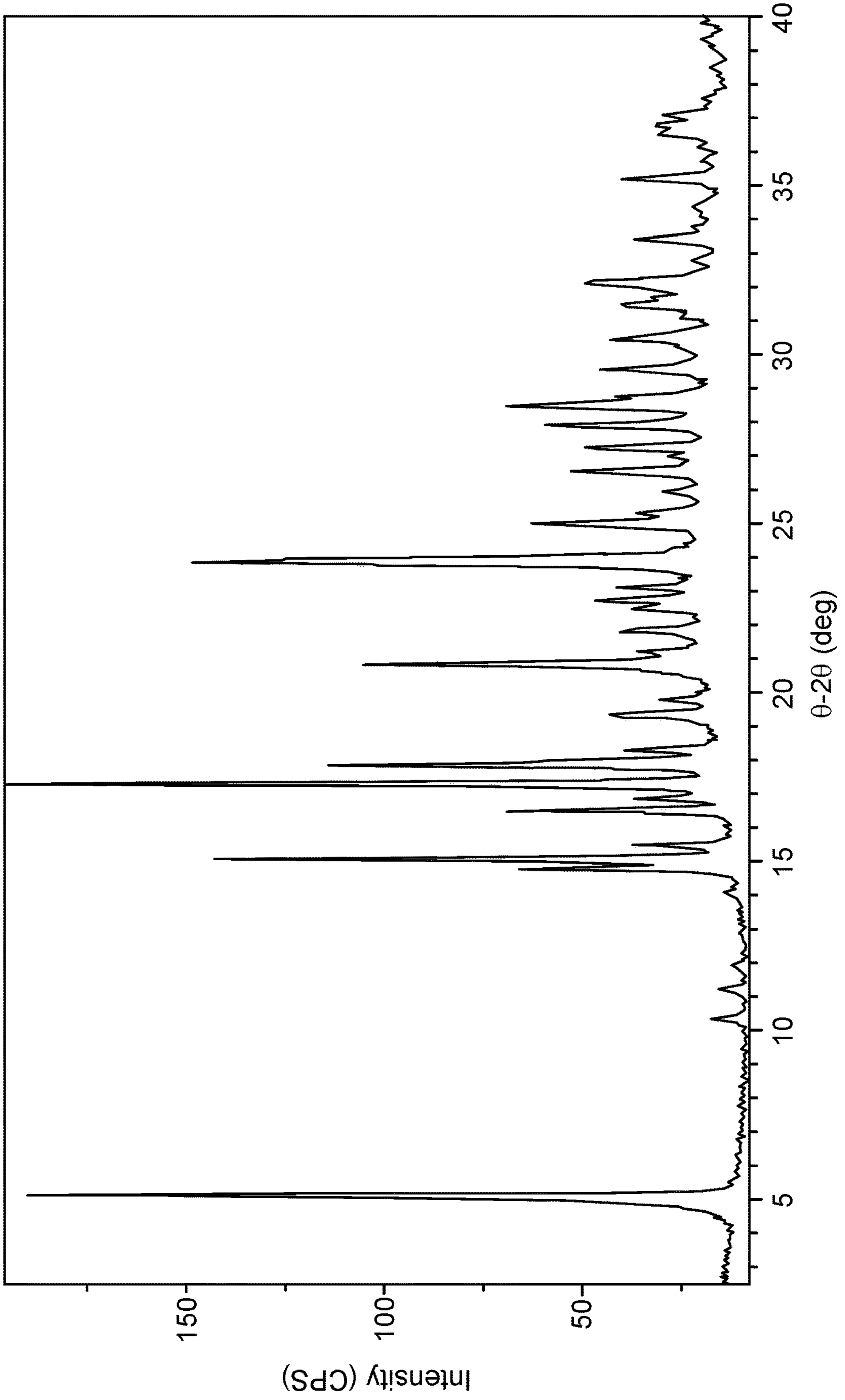
FIG. 11 shows an X-ray powder diffraction (XRPD) pattern of crystalline Form B.

In some embodiments, crystalline Form B of a compound having formula (I), is characterized by an X-ray powder diffraction pattern substantially in accordance with FIG. 11.

In some embodiments, crystalline Form B is substantially free of other crystalline or amorphous forms of the compound having formula (I).

In some embodiments, crystalline Form B is further characterized by a differential scanning calorimetry (DSC) thermogram including an endothermic peak at about 95.4° C. In some embodiments, crystalline Form B is further characterized by a differential scanning calorimetry (DSC) thermogram including an onset temperature of about 80.0° C. and an endothermic peak at about 95.4° C. In some embodiments, the differential scanning calorimetry (DSC) thermogram further includes one or more endothermic peaks at about 151.1° C., about 170.3° C., and 185.3° C.

Figure 12:
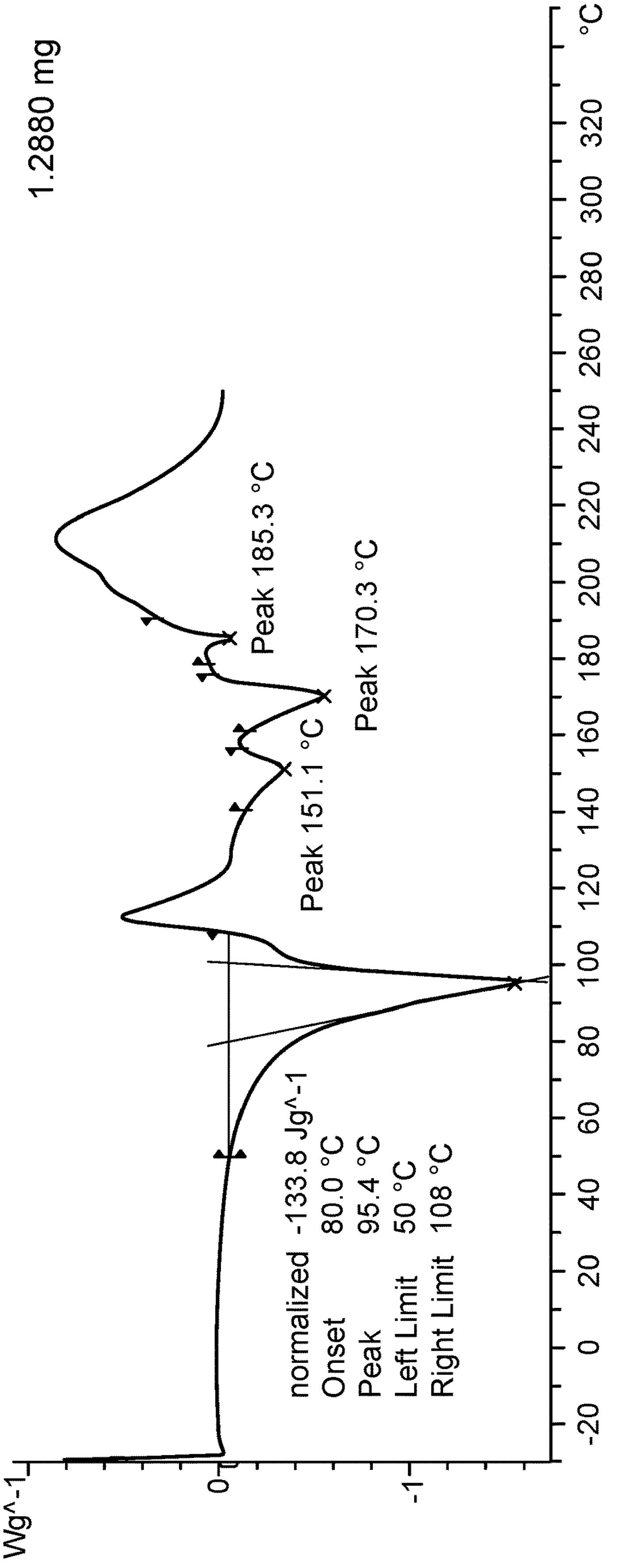
FIG. 12 shows a differential scanning calorimetry (DSC) thermogram of crystalline Form B.

In some embodiments, crystalline Form B is further characterized by a differential scanning calorimetry (DSC) thermogram substantially in accordance with FIG. 12.

In some embodiments, crystalline Form B is further characterized by a weight loss of about 3.4% upon heating from about 80° C. to about 145° C., as measured by a thermal gravimetric analysis (TGA).

Figure 13:
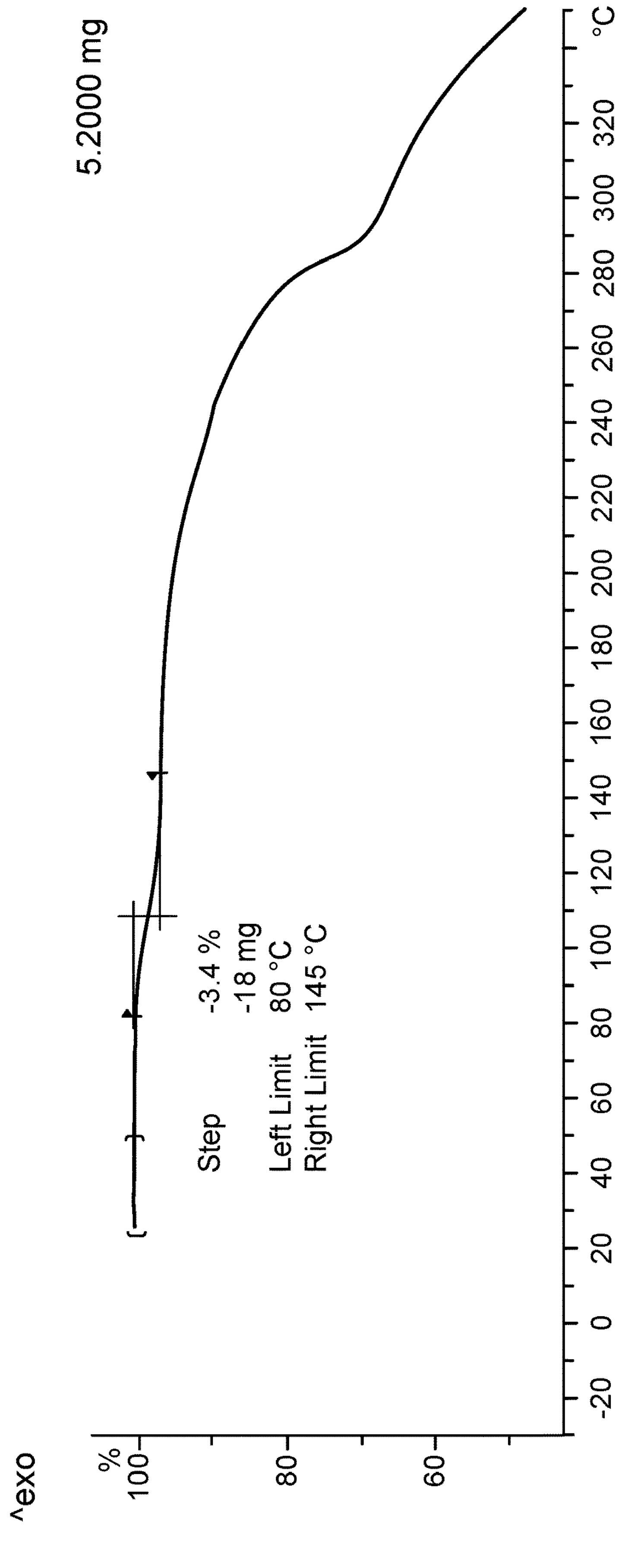
FIG. 13 shows a thermal gravimetric analysis (TGA) thermogram of crystalline Form B.

In some embodiments, crystalline Form B is further characterized by a thermal gravimetric analysis (TGA) thermogram substantially in accordance with FIG. 13.

In some embodiments, crystalline Form B is in a hydrate form. In some embodiments, crystalline Form B is in a monohydrate form.

In some embodiments, crystalline Form B is characterized by an X-ray powder diffraction pattern substantially in accordance with FIG. 11; and is further characterized by a differential scanning calorimetry (DSC) thermogram substantially in accordance with FIG. 12. In some embodiments, crystalline Form B is characterized by an X-ray powder diffraction pattern substantially in accordance with FIG. 11; is further characterized by a differential scanning calorimetry (DSC) thermogram substantially in accordance with FIG. 12; and is further characterized by a thermal gravimetric analysis (TGA) thermogram substantially in accordance with FIG. 13.

III-5. Crystalline Form C

In one embodiment, the present disclosure provides crystalline Form C of a compound having formula (I), characterized by an X-ray powder diffraction (XRPD) pattern including peaks at 14.4, 17.4, 19.1, 19.4, and 22.3 degrees 2θ (±0.2 degrees 2θ). In some embodiments, the X-ray powder diffraction pattern further comprises peaks at 6.9, 11.7, 23.7, 24.9, and 25.1 degrees 2θ (±0.2 degrees 2θ). In some embodiments, crystalline Form C is characterized by an X-ray powder diffraction (XRPD) pattern including peaks (i.e., the first 10 peaks ranked according to relative peak intensity %) at 6.9, 11.7, 14.4, 17.4, 19.1, 19.4, 22.3, 23.7, 24.9, and 25.1 degrees 2θ (±0.2 degrees 2θ). In some embodiments, crystalline Form C is characterized by an X-ray powder diffraction (XRPD) pattern including three, four, five or more peaks listed in Table 10A or Table 10B. In some embodiments, crystalline Form C is characterized by an X-ray powder diffraction (XRPD) pattern including at least five peaks listed in Table 10A or Table 10B.

Figure 14:
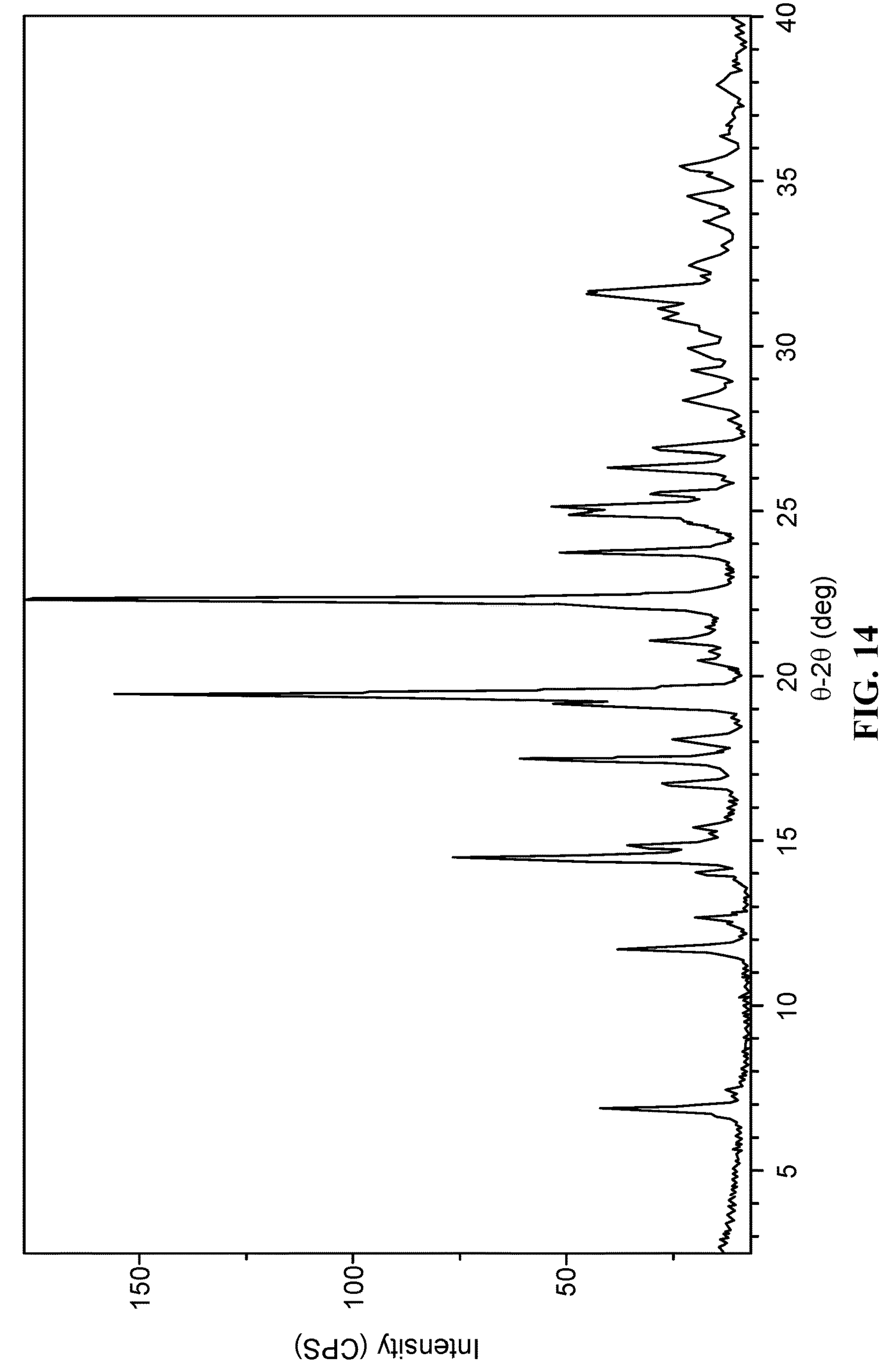
FIG. 14 shows an X-ray powder diffraction (XRPD) pattern of crystalline Form C.

In some embodiments, crystalline Form C of a compound having formula (I), is characterized by an X-ray powder diffraction pattern substantially in accordance with FIG. 14.

In some embodiments, crystalline Form C is substantially free of other crystalline or amorphous forms of the compound having formula (I).

Figure 15A:
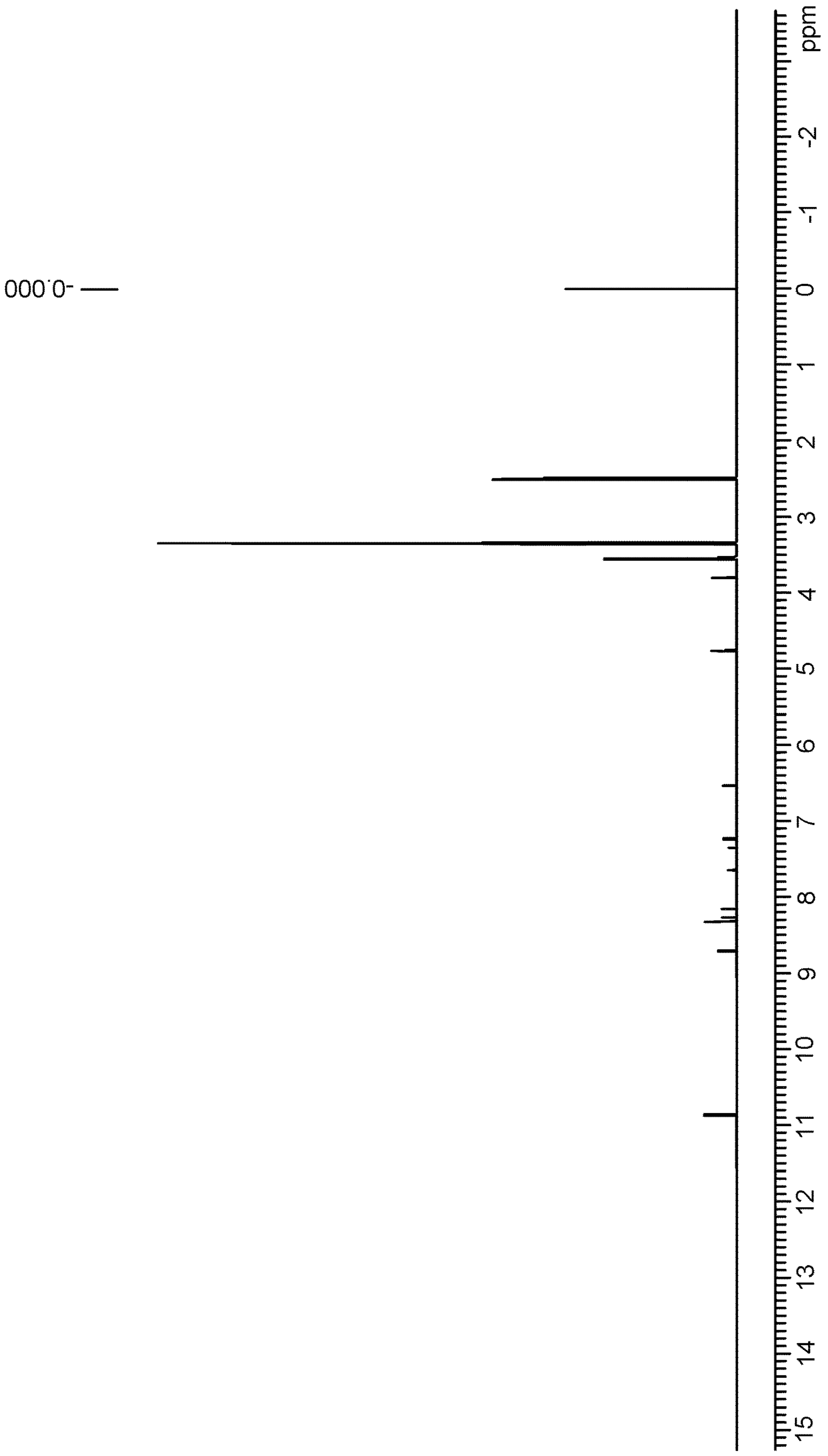
FIGS. 15A and 15B show a $^1$H NMR spectrum of crystalline Form C.
Figure 15B:
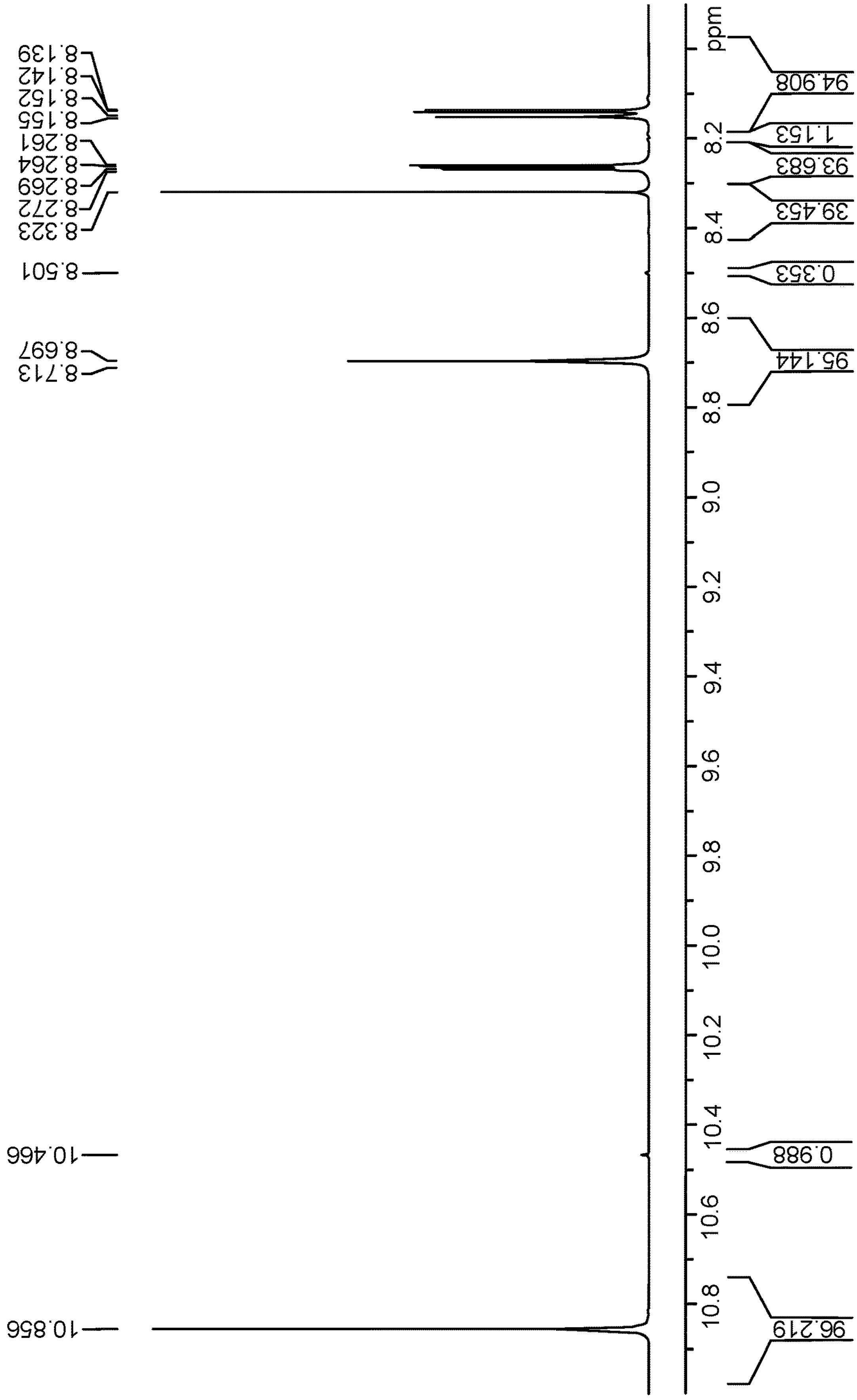

In some embodiments, crystalline Form C is further characterized by a 1H NMR spectrum as shown in FIG. 15A and FIG. 15B.

In some embodiments, crystalline Form C is in a solvate form. In some embodiments, crystalline Form C is in a chloroform solvate form. In some embodiments, crystalline Form C is in a chloroform solvate form; and a ratio of chloroform to the compound of formula (I) is no more than 1:1 by mole, as determined by a crystal volume of the X-ray powder diffraction (XRPD). In some embodiments, crystalline Form C is in a chloroform solvate form; and a ratio of chloroform to the compound of formula (I) is about 0.4:1 by mole, as determined by a 1H NMR spectrum as shown in FIG. 15A and FIG. 15B.

In some embodiments, crystalline Form C is characterized by an X-ray powder diffraction pattern substantially in accordance with FIG. 14; and is further characterized by a 1H NMR spectrum as shown in FIG. 15A and FIG. 15B.

III-6. Crystalline Form H

In one embodiment, the present disclosure provides crystalline Form H of a compound having formula (I), characterized by an X-ray powder diffraction (XRPD) pattern including peaks at 5.1, 17.3, 18.7, 23.4, and 25.6 degrees 2θ (±0.2 degrees 2θ). In some embodiments, the X-ray powder diffraction pattern further comprises peaks at 14.3, 16.5, 18.1, 21.02, and 22.5 degrees 2θ (±0.2 degrees 2θ). In some embodiments, the X-ray powder diffraction pattern further comprises peaks at 15.8, 16.3, 18.9, and 19.6 degrees 2θ (±0.2 degrees 2θ). In some embodiments, crystalline Form H is characterized by an X-ray powder diffraction (XRPD) pattern including peaks (i.e., the first 10 peaks ranked according to relative peak intensity %) at 5.1, 14.3, 16.5, 17.3, 18.1, 18.7, 21.02, 22.5, 23.4, and 25.6 degrees 2θ (±0.2 degrees 2θ). In some embodiments, crystalline Form H is characterized by an X-ray powder diffraction (XRPD) pattern including three, four, five or more peaks listed in Table 12A or Table 12B. In some embodiments, crystalline Form H is characterized by an X-ray powder diffraction (XRPD) pattern including at least five peaks listed in Table 12A or Table 12B.

Figure 16:
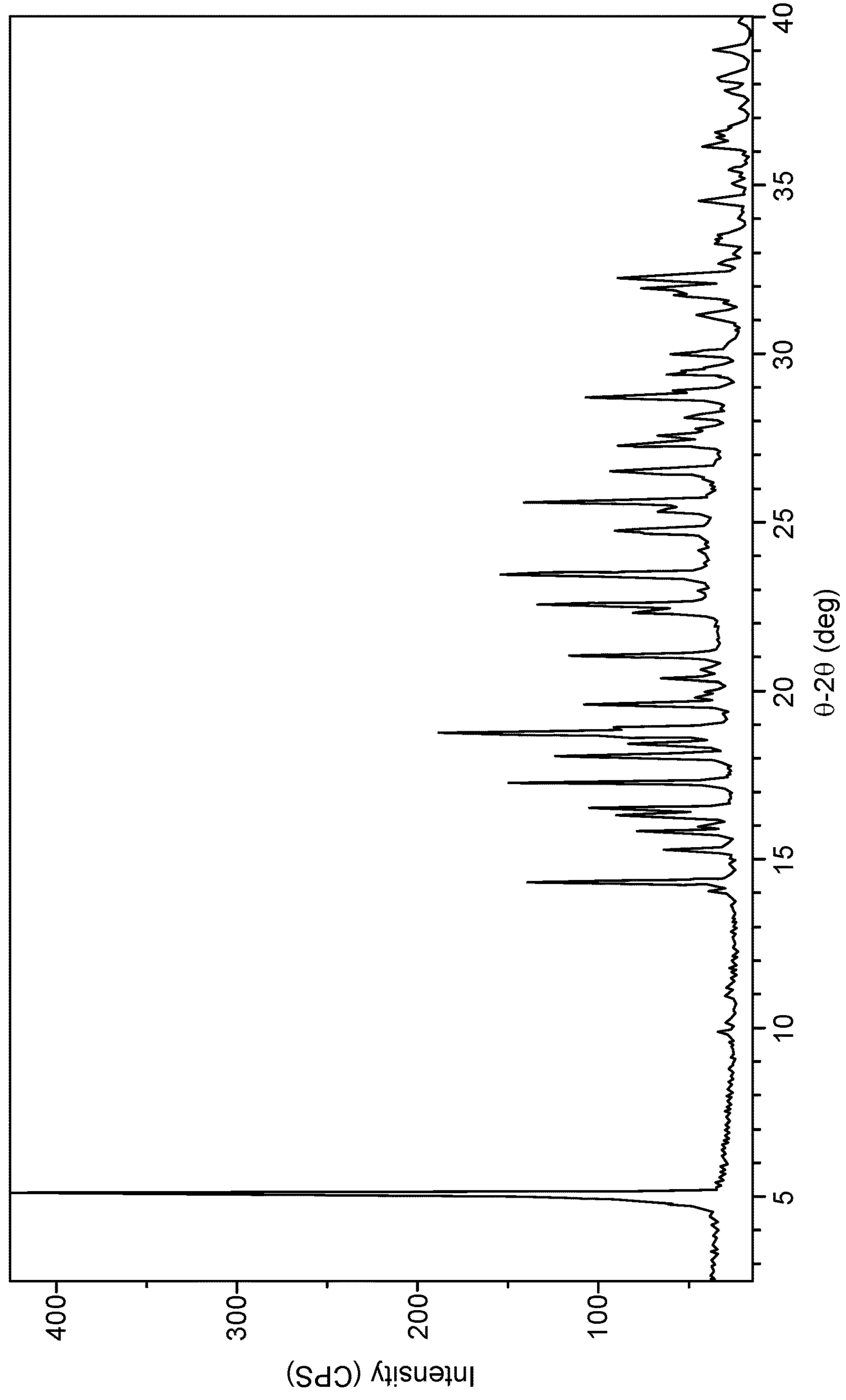
FIG. 16 shows an X-ray powder diffraction (XRPD) pattern of crystalline Form H.

In some embodiments, crystalline Form H of a compound having formula (I), is characterized by an X-ray powder diffraction pattern substantially in accordance with FIG. 16.

In some embodiments, crystalline Form H is substantially free of other crystalline or amorphous forms of the compound having formula (I).

In some embodiments, crystalline Form H is in a solvate form. In some embodiments, crystalline Form His in a methanol solvate form. In some embodiments, crystalline Form H is in a methanol solvate form; and a ratio of methanol to the compound of formula (I) is no more than 1:1 by mole, as determined by a crystal volume of the X-ray powder diffraction (XRPD).

IV. Method for Preparing Crystalline Form A

In one aspect, the present disclosure provides a method for preparing crystalline Form A as described herein via a crystallization method (referred hereafter as a first method). The first method includes:

a) forming a first mixture including a compound having formula (I):

(I)

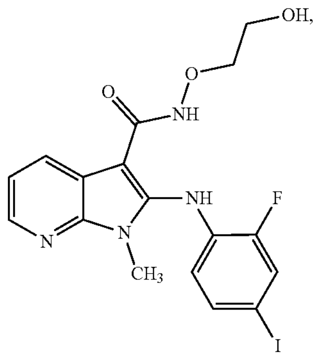

and tetrahydrofuran (THF) at a first temperature of from about 50° C. to about 65° C.;

b) cooling the first mixture to a second temperature of from about 35° C. to about 45° C.;

c) adding one or more seeds of the crystalline Form A prior to step d) to form a second mixture, or during step d);

d) adding methyl-tertiary-butyl ether (MTBE) to form a third mixture;

e) cooling the third mixture to a third temperature of no more than about 25° C. to form a fourth mixture including a precipitate; and f) isolating the precipitate from the fourth mixture to provide the crystalline Form A, wherein steps c) and d) are each maintained at the second temperature.

With reference to the first method, the compound of formula (I) can be in any form (e.g., a crystalline form or amorphous form). In some embodiments, the compound of formula (I) is in a crystalline form (e.g., Forms A, E, F, B, C, and H, as described herein). In some embodiments, the compound of formula (I) is in Form A, Form E, Form F, Form B, Form C, Form H, or a combination thereof. In some embodiments, the compound of formula (I) is in Form A, provided that the compound of formula (I) in Form A has a purity of less than about 99%. In some embodiments, the compound of formula (I) is a crystalline form other than Form A. In some embodiments, the compound of formula (I) is in an amorphous form.

With reference to the first method, in some embodiments, the compound of formula (I) has a purity of at least about 90%. In some embodiments, the compound of formula (I) has a purity of from about 90% to about 99%. In some embodiments, the compound of formula (I) has a purity of from about 95% to about 99%. In some embodiments, the compound of formula (I) has a purity of from about 96% to about 99%, from about 97% to about 99%, or from about 98% to about 99%. In some embodiments, the compound of formula (I) has a purity of about 96%. In some embodiments, the compound of formula (I) has a purity of about 97%. In some embodiments, the compound of formula (I) has a purity of about 98%. In some embodiments, the compound of formula (I) has a purity of about 99%.

With reference to the first method, in some embodiments, the compound of formula (I) is present in the first mixture in an amount of from about 50 g/L to about 150 g/L, from about 75 g/L to about 125 g/L, from about 90 g/L to about 110 g/L, or about 100 g/L. In some embodiments, the compound of formula (I) is present in the first mixture in an amount of from about 75 g/L to about 125 g/L. In some embodiments, the compound of formula (I) is present in the first mixture in an amount of from about 90 g/L to about 110 g/L. In some embodiments, the compound of formula (I) is present in the first mixture in an amount of about 100 g/L.

With reference to the first method, in some embodiments, a ratio of THF to MTBE is from about 1:4 to about 2:1 by volume. In some embodiments, a ratio of THF to MTBE is from about 1:3 to about 1:1 by volume. In some embodiments, a ratio of THF to MTBE is about 1:2 by volume.

With reference to the first method, in some embodiments, the one or more seeds of the crystalline Form A are added prior to step d) to form the second mixture. In some embodiments, the one or more seeds of the crystalline Form A are added during step d) to form the third mixture. In some embodiments, the one or more seeds of the crystalline Form A are added in step d), after addition of about ⅕ by volume of a total amount of MTBE (e.g., 4 out of 20 volumes of MTBE). In some embodiments, the one or more seeds of the crystalline Form A are added in step d), after addition of about ⅖ by volume of a total amount of MTBE (e.g., 8 out of 20 volumes of MTBE).

With reference to the first method, in some embodiments, the one or more seeds of the crystalline Form A are added in an amount of about 0.5% to about 2% by weight of the compound of formula (I). In some embodiments, the one or more seeds of the crystalline Form A are added in an amount of about 1% to about 1.5% by weight of the compound of formula (I). In some embodiments, the one or more seeds of the crystalline Form A are the Form A of Example 2, characterized according to Table 1.

With reference to the first method, in some embodiments, the first mixture is a solution. In some embodiments, the first mixture is a solution substantially free of a solid. In some embodiments, the second mixture and/or the third mixture are each a slurry. In some embodiments, the second mixture is a first slurry. In some embodiments, the third mixture is a second slurry.

With reference to the first method, in some embodiments, the second mixture is further stirred for a period of from about 20 to 120 minutes prior to step d), while maintaining at the second temperature. In some embodiments, the second mixture is further stirred for a period of from about 20 to 60 minutes prior to step d), while maintaining at the second temperature. In some embodiments, the second mixture is further stirred for a period of about 30 minutes prior to step d), while maintaining at about 40° C.

With reference to the first method, in some embodiments, step d) is conducted over a period of from about 1 to 3 hours while maintaining at the second temperature. In some embodiments, step d) is conducted over a period of from about 1.5 hours while maintaining at about 40° C.

With reference to the first method, in some embodiments, the cooling of step e) is conducted over a period of from about 1 to 3 hours. In some embodiments, the cooling of step e) is conducted over a period of about 2 hours.

With reference to the first method, in some embodiments, the fourth mixture is further stirred for a period of from about 1 to 24 hours while maintaining at the third temperature. In some embodiments, the fourth mixture is further stirred for a period of from about 1 to 24 hours while maintaining at about 20° C. In some embodiments, the fourth mixture is further stirred for a period of about 1 hour while maintaining at about 20° C.

With reference to the first method, in some embodiments, the first temperature is from about 55° C. to 65° C. In some embodiments, the first temperature is from about 60° C. to 65° C. In some embodiments, the first temperature is about 55° C. to 60° C. In some embodiments, the first temperature is about 55° C. In some embodiments, the second temperature is about 40° C. In some embodiments, the third temperature is about 20° C.

In another aspect, the present disclosure provides a method for preparing for preparing crystalline Form A as described herein via a slurry-to-slurry method (referred hereafter as a second method). The second method includes:

a) forming a third slurry including a compound having formula (I):

(I)

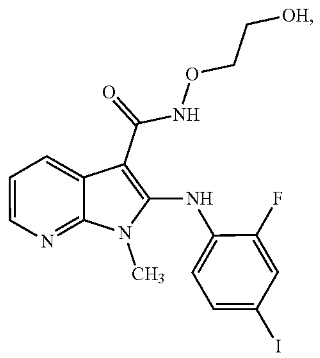

tetrahydrofuran (THF) and methyl-tertiary-butyl ether (MTBE);

b) adding one or more seeds of the crystalline Form A to form a fourth slurry;

c) stirring the fourth slurry to form a fifth slurry; and d) isolating a precipitate from the fifth slurry to provide the crystalline Form A, wherein the one or more seeds of the crystalline Form A are in an amount of at least about 5% by weight of the compound of formula (I); and steps a) to c) are each maintained at a temperature of from about 40° C. to about 50° C.

With reference to the second method, the compound of formula (I) can be in any form (e.g., a crystalline form or amorphous form). In some embodiments, the compound of formula (I) is in a crystalline form (e.g., Forms A, E, F, B, C, and H, as described herein). In some embodiments, the compound of formula (I) is in Form A, Form E, Form F, Form B, Form C, Form H, or a combination thereof. In some embodiments, the compound of formula (I) is in Form A, provided that the compound of formula (I) in Form A has a purity of less than about 99%. In some embodiments, the compound of formula (I) is a crystalline form other than Form A. In some embodiments, the compound of formula (I) is in an amorphous form.

With reference to the second method, in some embodiments, the compound of formula (I) has a purity of at least about 90%. In some embodiments, the compound of formula (I) has a purity of from about 90% to about 99%. In some embodiments, the compound of formula (I) has a purity of from about 95% to about 99%. In some embodiments, the compound of formula (I) has a purity of from about 96% to about 99%, from about 97% to about 99%, or from about 98% to about 99%. In some embodiments, the compound of formula (I) has a purity of about 96%. In some embodiments, the compound of formula (I) is has a purity of about 97%. In some embodiments, the compound of formula (I) has a purity of about 98%. In some embodiments, the compound of formula (I) has a purity of about 99%.

With reference to the second method, in some embodiments, the compound of formula (I) is present in the third slurry in an amount of from about 20 g/L to about 50 g/L, from about 25 g/L to about 40 g/L, from about 30 g/L to about 35 g/L, or about 33 g/L. In some embodiments, the compound of formula (I) is present in the third slurry in an amount of from about 25 g/L to about 40 g/L. In some embodiments, the compound of formula (I) is present in the third slurry in an amount of from about 30 g/L to about 35 g/L. In some embodiments, the compound of formula (I) is present in the third slurry in an amount of about 33 g/L.

With reference to the second method, in some embodiments, a ratio of THF to MTBE in the third slurry is from about 1:4 to about 2:1 by volume. In some embodiments, a ratio of THF to MTBE in the third slurry is from about 1:3 to about 1:1 by volume. In some embodiments, a ratio of THF to MTBE in the third slurry is about 1:2 by volume.

With reference to the second method, in some embodiments, the one or more seeds of the crystalline Form A are in an amount of from about 5% to 20% by weight of the compound of formula (I). In some embodiments, the one or more seeds of the crystalline Form A are in an amount of about 5% by weight of the compound of formula (I). In some embodiments, the one or more seeds of the crystalline Form A are in an amount of about 10% by weight of the compound of formula (I).

With reference to the second method, in some embodiments, step c) of the stirring is conducted for a period of from about 1 to 5 days. In some embodiments, step c) of the stirring is conducted for a period of from about 1 to 2 days. In some embodiments, step c) of the stirring is conducted for a period of about 1.5 days.

With reference to the second method, in some embodiments, steps a) to c) are each maintained at a temperature of about 45° C.

With reference to the second method, after step c), in some embodiments, the fifth slurry is further cooled to a temperature of no more than about 25° C. and stirred for a period of from about 1 to 24 hours while maintaining at the temperature of no more than about 25° C. In some embodiments, the fifth slurry is further cooled to about 20° C. over a period of from about 1 to 3 hours; and is further stirred for a period of from about 1 to 24 hours while maintaining at about 20° C. In some embodiments, the fifth slurry is further cooled to about 20° C. over a period of about 2 hours; and is further stirred for a period of from about 1 hour while maintaining at about 20° C.

In general, the crystalline Form A of the compound of formula (I) can be isolated by common methods (e.g., filtration and/drying). With reference to both the first and second methods as described above, in some embodiments, the precipitate is isolated by filtration. In some embodiments, the isolated precipitate is further dried to provide the crystalline Form A. In some embodiments, the isolated precipitate is further dried by heating (e.g., 45° C.) to provide the crystalline Form A. In some embodiments, the isolated precipitate is further dried by heating (e.g., 45° C.) for several days (e.g., 1-2 days) to provide the crystalline Form A.

With reference to both the first and second methods, in some embodiments, the crystalline Form A of the compound of formula (I) isolated has a purity of at least about 99%. In some embodiments, the crystalline Form A of the compound of formula (I) isolated has a purity of at least about 99.5%. In some embodiments, the crystalline Form A of the compound of formula (I) isolated has a purity of about 99.9%.

The crystalline Form A of the compound of formula (I), prepared by both the first and second methods as described herein, can be characterized according to Section III-1. In some embodiments, the crystalline Form A of the compound of formula (I), prepared by both the first and second methods as described herein, has a X-ray powder diffraction pattern substantially in accordance with FIG. 1.

V. Compositions

In another aspect, the present disclosure provides a pharmaceutical composition prepared by a method including combining a crystalline form of the compound of formula (I) with one or more pharmaceutically acceptable carriers, wherein the crystalline form is any one of crystalline Forms A, B, C, E, F, and H, each of which is as defined and described herein. In some embodiments, the crystalline form is Form A as defined and described herein.

The crystalline forms provided herein can be formulated into pharmaceutical compositions using methods available in the art and those disclosed herein. Any of the crystalline forms disclosed herein can be provided in the appropriate pharmaceutical composition and be administered by a suitable route of administration.

Administration of the composition described herein to a subject may be local or non-systemic, e.g., topical, subcutaneously, intradermal, or intralesional. In some embodiments, the composition can be administered by topical administration. In some embodiments, the composition can be administered by intradermal administration. In some embodiments, the composition can be administered by intralesional administration, e.g., by intralesional injection.

The methods provided herein encompass administering pharmaceutical compositions prepared from at least one crystalline form of the compound as described herein, either alone or in the form of a combination with one or more compatible and pharmaceutically acceptable carriers, such as diluents or adjuvants, or with another agent for the treatment of a MEK-inhibitor responsive disorder or disease, a MEK-inhibitor responsive dermal disorder or disease, a MEK-mediated disorder or disease, or a MEK-mediated dermal disorder or disease where the subject is in need thereof.

In some embodiments, the second agent can be formulated or packaged with the crystalline form of the compound provided herein. Of course, the second agent will only be formulated with the crystalline form of the compound provided herein when, according to the judgment of those of skill in the art, such co-formulation should not interfere with the activity of either agent or the method of administration. In some embodiments, the crystalline form of the compound provided herein and the second agent are formulated separately. They can be packaged together, or packaged separately, for the convenience of the practitioner of skill in the art.

In clinical practice the active agents provided herein may be administered by any conventional route, in particular topically, subcutaneously, intradermally, intralesionally, orally, parenterally, rectally or by inhalation (e.g. in the form of aerosols). In some embodiments, the composition prepared from the crystalline form of the compound provided herein is administered topically, subcutaneously, intradermally, or intralesionally. In some embodiments, the composition prepared from the crystalline form of the compound provided herein is administered topically. In some embodiments, the composition prepared from the crystalline form of the compound provided herein is administered intradermally. In some embodiments, the composition prepared from the crystalline form of the compound provided herein is administered intralesionally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, in some embodiments, wetting, sweetening or flavoring products.

Use may be made, of compositions for topical administration as lotions, tinctures, creams, emulsions, gels or ointments. In these compositions, the active product is mixed with one or more inert excipients including water, acetone, ethanol, ethylene glycol, propylene glycol, butane 1,3 diol, isopropyl myristate, isopropyl palmitate, mineral oil, and mixtures thereof.

The compositions for parenteral, intralesional, or intradermal administration can be emulsions or sterile solutions. Use may be made, as solvent or vehicle, of propylene glycol, a polyethylene glycol, vegetable oils, in particular olive oil, or injectable organic esters, in some embodiments, ethyl oleate. These compositions can also contain adjuvants, in particular wetting, isotonizing, emulsifying, dispersing and stabilizing agents. Sterilization can be carried out in several ways, in some embodiments, using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, in some embodiments, dextran, mannitol or lactose.

In some embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Remington: The Science and Practice of Pharmacy; Pharmaceutical Press; 22 edition (Sep. 15, 2012).

Typical pharmaceutical compositions and dosage forms comprise one or more excipients. Suitable excipients are well-known to those skilled in the art of pharmacy, and in some embodiments, suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, in some embodiments, in the U.S. Pharmacopeia (USP 36-NF 31 S2). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. In some embodiments, suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in some embodiments, in purified form, together with a suitable amount of carrier so as to provide the form for proper administration to the subject. The formulation should suit the mode of administration. In some embodiments, the pharmaceutical compositions or single unit dosage forms are sterile and in suitable form for administration to a subject, in some embodiments, an animal subject, such as a mammalian subject, in some embodiments, a human subject.

A pharmaceutical composition is formulated to be compatible with its intended route of administration. In some embodiments, routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In some embodiments, the route of administration is intradermal, topical, or intralesional administration. In some embodiments, the route of administration is non-systemic administration. In some embodiments, the composition is formulated in accordance with routine procedures as a pharmaceutical composition adapted for intravenous, subcutaneous, intramuscular, oral, intranasal or topical administration to human beings. In some embodiments, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

In some embodiments, dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. In some embodiments, a dosage form used in the initial treatment of a MEK-inhibitor responsive disorder or disease, a MEK-inhibitor responsive dermal disorder or disease, a MEK-mediated disorder or disease, or a MEK-mediated dermal disorder or disease may contain larger amounts of one or more of the active ingredients it comprises than a dosage form used in the maintenance treatment of the same disorder or disease. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington: The Science and Practice of Pharmacy; Pharmaceutical Press; 22 edition (Sep. 15, 2012).

Generally, the ingredients of compositions are supplied either separately or mixed together in unit dosage form, in some embodiments, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington: The Science and Practice of Pharmacy; Pharmaceutical Press; 22 edition (Sep. 15, 2012).

In some embodiments, the oral dosage forms are solid and prepared under anhydrous diseases or disorders with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. In some embodiments, excipients suitable for use in oral liquid or aerosol dosage forms include, but are not limited to, water, glycols, oils, alcohols, flavoring agents, preservatives, and coloring agents. In some embodiments, excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In some embodiments, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In some embodiments, excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

In some embodiments, fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

In some embodiments, suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, PA), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, in some embodiments, a syloid silica gel (AEROSIL 200, manufactured by W.R. Grace Co. of Baltimore, MD), a coagulated aerosol of synthetic silica (marketed by Degussa Co. of Plano, TX), CAB O SIL (a pyrogenic silicon dioxide product sold by Cabot Co. of Boston, MA), and mixtures thereof. If used at all, lubricants are typically used in an amount of less than about 1 weight percent of the pharmaceutical compositions or dosage forms into which they are incorporated.

Delayed Release Dosage Forms

Compositions prepared from active ingredients such as the crystalline forms of the compound provided herein can be administered by controlled release means or by delivery devices that are well known to those of ordinary skill in the art. In some embodiments, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, in some embodiments, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the disease or disorder in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various diseases or disorders including, but not limited to, pH, temperature, enzymes, water, or other physiological diseases or disorders or compounds.

In some embodiments, the drug may be administered using intravenous infusion, an implantable osmotic pump, a transdermal patch, liposomes, or other modes of administration. In some embodiments, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In some embodiments, polymeric materials can be used. In some embodiments, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249: 1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In some embodiments, provided are parenteral dosage forms. In some embodiments, parenteral dosage forms can be administered to subjects by various routes including, but not limited to, subcutaneous, intravenous (including bolus injection), intramuscular, and intra-arterial. In some embodiments, parenteral dosage forms can be administered to subjects by various routes including, but not limited to, topical, intradermal, or intralesional. Because their administration typically bypasses subjects' natural defenses against contaminants, parenteral dosage forms are typically, sterile or capable of being sterilized prior to administration to a subject. In some embodiments, parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. In some embodiments, suitable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy; Pharmaceutical Press; 22 edition (Sep. 15, 2012); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Suitable carriers (e.g., excipients and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical carriers include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. In some embodiments, materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. Moisturizers or humectants can also be added to pharmaceutical compositions and dosage forms if desired. Examples of such additional ingredients are well known in the art. See, e.g., Remington: The Science and Practice of Pharmacy; Pharmaceutical Press; 22 edition (Sep. 15, 2012).

Depending on the specific tissue to be treated, additional components may be used prior to, in conjunction with, or subsequent to treatment with active ingredients provided. In some embodiments, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Topical Formulations

In some embodiments, the pharmaceutical composition as described herein is a topical formulation. The topical formulations can be any one of the formulations as described in PCT/US2019/000066, the content of which is incorporated herein in its entirety for all purposes. In some embodiments, the topical formulation is prepared from any one of crystalline forms of the compound of formula (I), wherein the crystalline form is any one of crystalline Forms A, B, C, E, F, and H, each of which is as defined and described herein. In some embodiments, the topical formulation is prepared from crystalline Form A of the compound of formula (I), wherein crystalline Form A is as defined and described herein.

In some embodiments, the topical formulation is in a paint, a lotion, a spray, an ointment, a cream, a gel, or a patch.

VI. Methods

In a third aspect, the present disclosure provides a method of treating a skin disorder. The method includes administering a crystalline form of the compound of formula (I) or a pharmaceutical composition thereof, thereby treating the skin disease, wherein the crystalline form is any one of crystalline Forms A, B, C, E, F, and H, each of which is as defined and described herein; and the pharmaceutical composition is defined and described herein. In some embodiments, the crystalline form is Form A as defined and described herein.

In some embodiments, provided herein is a method for treating a skin disorder where the subject is in need thereof and the skin disorder is a MEK-inhibitor responsive dermal disorder or disease or a MEK-mediated dermal disorder or disease in a subject. In some embodiments, the method includes administering the subject with a therapeutically or prophylactically effective amount of a crystalline form of the compound of formula (I) or a pharmaceutical composition thereof, thereby treating the skin disease, wherein the crystalline form is any one of crystalline Forms A, B, C, E, F, and H, each of which is as defined and described herein; and the pharmaceutical composition is defined and described herein. In some embodiments, the method includes administering the subject with a therapeutically or prophylactically effective amount of crystalline Form A of the compound of formula (I) or a pharmaceutical composition thereof, thereby treating the skin disease, wherein crystalline Form A and the pharmaceutical composition are each defined and described herein. In some embodiments, the method includes administering the subject with a therapeutically effective amount of a crystalline form of the compound of formula (I) or a pharmaceutical composition thereof, thereby treating the skin disease, wherein the crystalline form is any one of crystalline Forms A, B, C, E, F, and H, each of which is as defined and described herein; and the pharmaceutical composition is defined and described herein. In some embodiments, the method includes administering the subject with a therapeutically effective amount of crystalline Form A of the compound of formula (I) or a pharmaceutical composition thereof, thereby treating the skin disease, wherein crystalline Form A and the pharmaceutical composition are each defined and described herein.

In some embodiments, the MEK-inhibitor responsive dermal disorder or MEK-mediated dermal disorder is selected from the group consisting of dermal rasopathy, neurofibromatosis type 1, dermal neurofibroma, subdermal neurofibroma, and superficial plexiform neurofibroma.

In some embodiments, the MEK-inhibitor responsive dermal disorder or MEK-mediated dermal disorder is neurofibromatosis type 1.

In some embodiments, administering includes contacting the crystalline form of the compound of formula (I) or the pharmaceutical composition thereof with the skin, mucous membranes, vagina, penis, larynx, vulva, cervix, or anus of the subject, by local or non-systemic application, e.g., topical application, wherein the crystalline form is any one of crystalline Forms A, B, C, E, F, and H, each of which is as defined and described herein; and the pharmaceutical composition thereof is as defined and described herein. In some embodiments, the crystalline form is crystalline Form A as defined and described herein.

In some embodiments, the tumor associated with neurofibromatosis type 1 (NF1), e.g., a dermal neurofibroma, a subdermal neurofibroma, or a superficial plexiform neurofibroma, is reduced, e.g., the size or the total tumor volume is reduced, by at least about 15% relative to the reference standard (e.g., from about 15% to about 60%), thereby treating the subject. In some embodiments, the reference standard is the size or the total tumor volume in an untreated control, e.g., from the same subject or a different subject.

In some embodiments, the size or total tumor volume of the tumor associated with neurofibromatosis type 1 (NF1), e.g., a dermal neurofibroma, a subdermal neurofibroma, or a superficial plexiform neurofibroma, is reduced by at least about 15%, by at least about 20%, by at least about 25%, by at least about 30%, by at least about 35%, by at least about 40%, by at least about 45%, by at least about 50%, by at least about 55%, by at least about 60% relative to the reference standard. In some embodiments, the reference standard is the size or the total tumor volume in an untreated control, e.g., from the same subject or a different subject.

In some embodiments, the method includes evaluating the subject with magnetic resonance imaging (MRI), or optical imaging, e.g., evaluating the volume of tumors obtained from the subject, e.g., prior to, during and/or after treatment.

Neurofibromatosis type 1 (NF1): In some embodiments, the dermal disorder is associated with NF1. NF1, also known as von Recklinghausen Neurofibromatosis or Peripheral Neurofibromatosis, occurs in approximately 1:3,000 births, and is one of the most prevalent genetic disorders and the most common neurocutaneous disorders. NF1 is caused by a deficiency in neurofibromin, which leads to hyperactivation of various cell-signaling pathways, e.g., Ras and Rho, is associated with several dermal disorders, including dermal neurofibromas (DFs); subdermal neurofibromas; superficial plexiform neurofibromas (PFs); cutaneous neurofibromas (CFs); café au lait spots; and axillary and inguinal freckling. DFs occur in over 95% of NF1 patients. DFs can appear anywhere on the body, with 88% of NF1 patients over 40 years of age having over 100 DFs. DFs can cause both severe physical pain, disfigurement, as well as social anxiety. Facial DFs can create significant social anxiety issues and pain among affected individuals. DFs (also known as cutaneous neurofibromas or discrete neurofibromas) grow from small nerves in the skin or just under the skin and appear as small bumps typically beginning around the time of puberty. Current treatment options for DF are limited to surgical excisin and $CO_2$ laser removal, both of which cause scarring and neither of which is preventative.

Other Dermal Rasopathies: In some embodiments, the dermal disorder is associated with enhanced activation of Ras. In some embodiments, the dermal disorder is selected from: psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots and Multiple lentigines syndrome (formerly called Leopard syndrome).

In some or any embodiments, the disease to be reduced, ameliorated, treated, or prevented is not cancer (e.g. melanoma).

In some embodiments, the disease to be reduced, ameliorated, treated, or prevented is cancer, a dermal rasopathy, a dermal disorder associated with neurofibromatosis type 1, a dermal neurofibroma, a subdermal neurofibroma, or a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

In some embodiments, the disease to be reduced, ameliorated, treated, or prevented is cancer. In some embodiments, the disease to be reduced, ameliorated, treated, or prevented is selected from the group consisting of basal cell carcinoma, squamous cell carcinoma, actinic keratosis, Kaposi's sarcoma, dermal lymphoma, cervical cancer, HPV-related squamous cell carcinoma, and melanoma.

In some embodiments, the disease to be reduced, ameliorated, treated, or prevented is a dermal rasopathy, a dermal disorder associated with neurofibromatosis type 1, a dermal neurofibroma, a subdermal neurofibroma, or a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

In some embodiments, the crystalline forms of the compound of formula (I) or pharmaceutical compositions thereof described herein are used for the reduction of a MEK-inhibitor responsive dermal disorder or disease or a MEK-mediated dermal disorder or disease where the subject is in need thereof.

In some embodiments, the crystalline forms of the compound of formula (I) or pharmaceutical compositions thereof described herein are used for the amelioration of a MEK-inhibitor responsive dermal disorder or disease or a MEK-mediated dermal disorder or disease where the subject is in need thereof.

In some embodiments, the crystalline forms of the compound of formula (I) or pharmaceutical compositions thereof described herein are used for prevention of a MEK-inhibitor responsive dermal disorder or disease or a MEK-mediated dermal disorder or disease where the subject is in need thereof.

In some embodiments, the crystalline forms of the compound of formula (I) or pharmaceutical compositions thereof described herein are used for treatment of a MEK-inhibitor responsive dermal disorder or disease or a MEK-mediated dermal disorder or disease where the subject is in need thereof.

In some embodiments, provided herein is a method for treating a skin disorder where the subject is in need thereof and the skin disorder is a birthmark in a subject. In some embodiments, the method includes administering the subject with a therapeutically or prophylactically effective amount of a crystalline form of a compound of formula (I) or a pharmaceutical composition thereof, wherein the crystalline form is any one of crystalline Forms A, B, C, E, F, and H, each of which is as defined and described herein; and the pharmaceutical composition thereof is as defined and described herein. In some embodiments, the crystalline form is crystalline Form A as defined and described herein.

In some embodiments, the birthmark is a port-wine stain (capillary malformation). Port-wine stains may be present at birth. Port-wine stains may be present at birth. Port-wine stains can occur anywhere on the body and the area of affected skin grows in proportion to general growth. Thickening of the lesion or the development of small lumps may occur in adulthood and can interfere with normal function (e.g., where the port-wine stain is near the eye or mouth). Port-wine stains may, in some cases, be part of a syndrome such as Sturge-Weber syndrome or Klippel-Trénaunay-Weber syndrome.

In some embodiments, provided herein is a method of treating a port-wine stain (capillary malformation) birthmark to reduce the cosmetic disfigurement or progression of the birthmark. In some embodiments, provided herein is a method of prophylactically treating a port-wine stain (capillary malformation) birthmark to prevent the progression of the birthmark, delaying the onset of the birthmark, or delaying the progression of the birthmark.

In some embodiments, the birthmark is epidermal nevi. Epidermal nevus is a benign skin growth with localized epidermal thickening that is often present at birth or within the first year of life. It typically appears as one or more oblong or linear growths that are skin colored, brown or gray in color. The surface can be wart-like or velvety with sharp borders. Malignant transformation can occur in some cases in middle aged or elderly subjects. Epidermal nevi are subdivided into keratinocytic and organoid nevi. Organoid nevi include nevus sebaceous (NS). In some embodiments, the birthmark is nevus sebaceous. Non-organoid keratinocytic epidermal nevus (KEN) is characterized by benign congenital hyperpigmented skin lesions. Contemplated within the scope of embodiments presented herein are other types of epidermal nevi, including nevus comedonicus. Nevus comedonicus (NC) is a hamartoma of the pilosebaceous unit that, like other epidermal nevi, typically presents at birth or during childhood. Clinically, NC lesions consist of linear arrays or clusters of dilated, keratin-plugged follicular orifices resembling comedones.

In some embodiments, provided herein is a method of treating epidermal nevi to reduce the cosmetic disfigurement or progression of the birthmark. In some embodiments, provided herein is a method of prophylactically treating epidermal nevi to prevent the progression of the birthmark, delaying the onset of the birthmark, or delaying the progression of the birthmark.

In some embodiments, the birthmark is nevus sebaceous. In some embodiments, provided herein is a method of treating a nevus sebaceous birthmark to reduce the cosmetic disfigurement or progression of the birthmark. In some embodiments, provided herein is a method of prophylactically treating a nevus sebaceous birthmark to prevent the progression of the birthmark, delaying the onset of the birthmark, or delaying the progression of the birthmark.

In some embodiments the birthmark is melanocytic nevus, including congenital nevi, blue nevi, and acquired melanocytic nevi. Malignant melanoma occasionally develops from the melanocytic nevus (also known as nevocytic nevus, nevus-cell nevus and commonly as a mole). Reasons for treatment of pigmented nevi (i.e., nevus cellular nevus) include prevention of malignant change, limiting malignant progression, cosmetic improvement, or prevention of other functional or anatomical changes.

In some embodiments, provided herein is a method of treating a melanocytic nevus to reduce the risk of cosmetic disfigurement or progression of the birthmark. In some embodiments, provided herein is a method of prophylactically treating a melanocytic nevus to prevent the progression of the birthmark, delaying the onset of the birthmark, or delaying the progression of the birthmark.

In some embodiments, the birthmark is dysplastic nevi. Dysplastic nevi (or atypical moles) are unusual-looking benign moles and may resemble melanoma. People who have atypical moles are at increased risk of developing melanoma in a mole or elsewhere on the body.

In some embodiments, provided herein is a method of treating dysplastic nevi to reduce the cosmetic disfigurement or progression of the birthmark. In some embodiments, provided herein is a method of prophylactically treating dysplastic nevi to prevent the progression of the birthmark, delaying the onset of the birthmark, or delaying the progression of the birthmark.

In some embodiments, the birthmark is a nevus spilus. Nevus spilus (also known as speckled lentiginous nevus and zosteriform lentiginous nevus) is a skin lesion that presents as a light brown patch of pigmentation, and within this patch, are multiple tiny dark brown spots.

In some embodiments, provided herein is a method of treating a nevus spilus birthmark to reduce the cosmetic disfigurement or progression of the birthmark. In some embodiments, provided herein is a method of prophylactically treating a nevus spilus birthmark to prevent the progression of the birthmark, delaying the onset of the birthmark, or delaying the progression of the birthmark.

In some embodiments, the birthmark is an arterio-venous malformation in the skin (e.g., blue rubber bleb nevus syndrome) which may present as skin lesions comprised of compressible blue subcutaneous nodules.

In some embodiments, provided herein is a method of treating an arterio-venous malformation to reduce the cosmetic disfigurement or progression of the birthmark. In some embodiments, provided herein is a method of prophylactically treating an arterio-venous malformation to prevent the progression of the birthmark, delaying the onset of the birthmark, or delaying the progression of the birthmark.

In some embodiments, the birthmark is a lymphatic malformation. A lymphatic malformation is a type of vascular nevus or birthmark due to malformed and dilated lymphatic vessels. The cystic hygroma (also called 'cystic lymphangioma' and 'lymphangioma cysticum') is a 'macrocytic' lymphatic malformation, and is composed of large fluid-filled spaces. It appears as a skin colored, red or bluish, somewhat transparent, swelling under the skin. Cavernous lymphangioma can affect any site on the body, including the tongue. Lymphangioma circumscriptum is a 'microcytic' lymphatic malformation. It appears as a cluster of small firm blisters filled with lymph fluid, resembling frogspawn.

In some embodiments, provided herein is a method of treating a lymphatic malformation to reduce the risk of the cosmetic disfigurement or progression of the birthmark. In some embodiments, provided herein is a method of prophylactically treating a lymphatic malformation to prevent the progression of the birthmark, delaying the onset of the birthmark, or delaying the progression of the birthmark.

In some embodiments, the birthmark is a congenital melanocytic nevus. The congenital melanocytic nevus appears as a circumscribed, light brown to black patch or plaque, heterogeneous in consistency, covering any size surface area and any part of the body. Congenital melanocytic nevus poses a risk for malignancy degeneration.

In some embodiments, provided herein is a method of treating a congenital melanocytic nevus to reduce the risk of cosmetic disfigurement or progression of the birthmark. In some embodiments, provided herein is a method of prophylactically treating a congenital melanocytic nevus to prevent the progression of the birthmark, delaying the onset of the birthmark, or delaying the progression of the birthmark.

In some embodiments, the crystalline forms of the compound of formula (I) or pharmaceutical compositions thereof described herein are used for the reduction of a birthmark in a subject in need thereof.

In some embodiments, the crystalline forms of the compound of formula (I) or pharmaceutical compositions thereof described herein are used for the amelioration of a birthmark in a subject in need thereof.

In some embodiments, the crystalline forms of the compound of formula (I) or pharmaceutical compositions thereof described herein are used for prevention of a birthmark (e.g., MEK-inhibitor responsive or MEK-mediated birthmarks) and/or prevention of worsening of a birthmark (e.g., where the birthmark may progress to a proliferative disease) in a subject in need thereof.

In some embodiments, the subject in need thereof is a human.

The birthmark is not cafe au lait spots.

In some embodiments, administering includes contacting the crystalline form of the compound of formula (I) or a pharmaceutical composition thereof with the skin of the subject, e.g., an affected region of the skin, e.g., a region of the skin having a birthmark.

In some embodiments, the appearance of a birthmark is reduced, e.g., the size, volume, or the total surface area is reduced, by at least about 15% relative to the reference standard (e.g., the size of the birthmark prior to start of treatment), thereby treating the subject. In some embodiments, the size, volume, or the total surface area on skin is reduced, by at least about 15%, by at least about 20%, by at least about 25%, by at least about 30%, by at least about 35%, by at least about 40%, by at least about 45%, by at least about 50%, by at least about 55%, by at least about 60% relative to the reference standard. In one embodiment, the reference standard is the size of the birthmark prior to start of treatment.

In some embodiments, provided herein is a method for treating a skin disorder where the subject is in need thereof and the skin disorder is a skin cancer in a subject. In some embodiments, the method includes administering the subject with a therapeutically or prophylactically effective amount of a crystalline form of a compound of formula (I) or a pharmaceutical composition thereof, wherein the crystalline form is any one of crystalline Forms A, B, C, E, F, and H, each of which is as defined and described herein; and the pharmaceutical composition thereof is as defined and described herein. In some embodiments, the crystalline form is crystalline Form A as defined and described herein.

In some embodiments, the skin cancer is a MEK-inhibitor responsive or MEK-mediated skin cancer.

In some embodiments, the skin cancer is a cutaneous squamous-cell carcinoma (cSCC).

In some embodiments, the cutaneous squamous-cell carcinoma is associate with exposure to ultraviolet radiation or immunosuppression in solid organ transplantation recipients (SOTRs). In some embodiments, the cutaneous squamous-cell carcinoma is associate with immunosuppression in solid organ transplantation recipients.

In some embodiments, the cutaneous squamous-cell carcinoma in solid organ transplantation recipients is a MEK-inhibitor responsive or MEK-mediated cutaneous squamous-cell carcinoma.

In some embodiments, administering includes contacting the crystalline form of the compound of formula (I) or a pharmaceutical composition thereof with the skin, mucous membranes, vagina, penis, larynx, vulva, cervix, or anus of the subject, by local or non-systemic application, e.g., topical, intradermal, or intralesional application or application by suppository, of the soft MEK inhibitor, wherein the crystalline form is any one of crystalline Forms A, B, C, E, F, and H, each of which is as defined and described herein; and the pharmaceutical composition thereof is as defined and described herein. In some embodiments, the crystalline form is crystalline Form A as defined and described herein.

In some embodiments, the tumor associated with cutaneous squamous-cell carcinoma (cSCC), e.g., a dermal carcinoma, is reduced, e.g., the size or the total tumor volume is reduced, by at least about 15% relative to the reference standard (e.g., from about 15% to about 60%), thereby treating the subject. In some embodiments, the reference standard is the size or the total tumor volume in an untreated control, e.g., from the same subject or a different subject.

In the SOTR population, these include patients who currently have SCC, who have had cSCC previously, or who have pre-cancers including squamous cell carcinoma in Situ (also known as Bowen's disease), or Actinic Keratoses, both of which are known to progress to SCC.

In some embodiments, provided herein is a method of treating a cutaneous squamous-cell carcinoma in solid organ transplantation recipients to reduce the progression of the cutaneous squamous-cell carcinoma (cSCC), wherein solid organ transplantation recipients currently have cutaneous squamous-cell carcinoma (cSCC), have had cutaneous squamous-cell carcinoma (cSCC) previously, have pre-cancers including squamous cell carcinoma in Situ (also known as Bowen's disease), or have Actinic Keratoses. In some embodiments, provided herein is a method of treating a cutaneous squamous-cell carcinoma in solid organ transplantation recipients to reduce the progression of the cutaneous squamous-cell carcinoma (cSCC). In some embodiments, provided herein is a method of treating a cutaneous squamous-cell carcinoma in solid organ transplantation recipients to reduce the progression of the cutaneous squamous-cell carcinoma (cSCC), wherein solid organ transplantation recipients have had cutaneous squamous-cell carcinoma (cSCC) previously. In some embodiments, provided herein is a method of treating a cutaneous squamous-cell carcinoma in solid organ transplantation recipients to reduce the progression of the cutaneous squamous-cell carcinoma (cSCC), wherein solid organ transplantation recipients have pre-cancers including squamous cell carcinoma in Situ (also known as Bowen's disease). In some embodiments, provided herein is a method of treating a cutaneous squamous-cell carcinoma in solid organ transplantation recipients to reduce the progression of the cutaneous squamous-cell carcinoma (cSCC), wherein solid organ transplantation recipients currently have Actinic Keratoses.

In some embodiments, provided herein is a method of prophylactically treating or preventing a cutaneous squamous-cell carcinoma in solid organ transplantation recipients to reduce the risk of tumor progression of the cutaneous squamous-cell carcinoma (cSCC), wherein solid organ transplantation recipients currently have cutaneous squamous-cell carcinoma (cSCC), have had cutaneous squamous-cell carcinoma (cSCC) previously, have pre-cancers including squamous cell carcinoma in Situ (also known as Bowen's disease), or have Actinic Keratoses. In some embodiments, provided herein is a method of prophylactically treating or preventing a cutaneous squamous-cell carcinoma in solid organ transplantation recipients to reduce the risk of tumor progression of the cutaneous squamous-cell carcinoma (cSCC). In some embodiments, provided herein is a method of prophylactically treating or preventing a cutaneous squamous-cell carcinoma in solid organ transplantation recipients to reduce the risk of tumor progression of the cutaneous squamous-cell carcinoma (cSCC), wherein solid organ transplantation recipients have had cutaneous squamous-cell carcinoma (cSCC) previously. In some embodiments, provided herein is a method of prophylactically treating or preventing a cutaneous squamous-cell carcinoma in solid organ transplantation recipients to reduce the risk of tumor progression of the cutaneous squamous-cell carcinoma (cSCC), wherein solid organ transplantation recipients have pre-cancers including squamous cell carcinoma in Situ (also known as Bowen's disease). In some embodiments, provided herein is a method of prophylactically treating or preventing a cutaneous squamous-cell carcinoma in solid organ transplantation recipients to reduce the risk of tumor progression of the cutaneous squamous-cell carcinoma (cSCC), wherein solid organ transplantation recipients currently have Actinic Keratoses.

In some embodiments, provided herein is a method of prophylactically treating or preventing a cutaneous squamous-cell carcinoma in solid organ transplantation recipients to delay the progression of the cutaneous squamous-cell carcinoma (cSCC), wherein solid organ transplantation recipients currently have cutaneous squamous-cell carcinoma (cSCC), have had cutaneous squamous-cell carcinoma (cSCC) previously, have pre-cancers including squamous cell carcinoma in Situ (also known as Bowen's disease), or have Actinic Keratoses. In some embodiments, provided herein is a method of prophylactically treating or preventing a cutaneous squamous-cell carcinoma in solid organ transplantation recipients to delay the progression of the cutaneous squamous-cell carcinoma (cSCC). In some embodiments, provided herein is a method of prophylactically treating or preventing a cutaneous squamous-cell carcinoma in solid organ transplantation recipients to delay the progression of the cutaneous squamous-cell carcinoma (cSCC), wherein solid organ transplantation recipients have had cutaneous squamous-cell carcinoma (cSCC) previously. In some embodiments, provided herein is a method of prophylactically treating or preventing a cutaneous squamous-cell carcinoma in solid organ transplantation recipients to delay the progression of the cutaneous squamous-cell carcinoma (cSCC), wherein solid organ transplantation recipients have pre-cancers including squamous cell carcinoma in Situ (also known as Bowen's disease). In some embodiments, provided herein is a method of prophylactically treating or preventing a cutaneous squamous-cell carcinoma in solid organ transplantation recipients to delay the progression of the cutaneous squamous-cell carcinoma (cSCC), wherein solid organ transplantation recipients currently have Actinic Keratoses.

In some embodiments, provided herein is a method of prophylactically treating or preventing a cutaneous squamous-cell carcinoma in solid organ transplantation recipients to prevent the progression of the cutaneous squamous-cell carcinoma (cSCC), wherein solid organ transplantation recipients currently have cutaneous squamous-cell carcinoma (cSCC), have had cutaneous squamous-cell carcinoma (cSCC) previously, have pre-cancers including squamous cell carcinoma in Situ (also known as Bowen's disease), or have Actinic Keratoses. In some embodiments, provided herein is a method of prophylactically treating or preventing a cutaneous squamous-cell carcinoma in solid organ transplantation recipients to prevent the progression of the cutaneous squamous-cell carcinoma (cSCC). In some embodiments, provided herein is a method of prophylactically treating or preventing a cutaneous squamous-cell carcinoma in solid organ transplantation recipients to prevent the progression of the cutaneous squamous-cell carcinoma (cSCC), wherein solid organ transplantation recipients have had cutaneous squamous-cell carcinoma (cSCC) previously. In some embodiments, provided herein is a method of prophylactically treating or preventing a cutaneous squamous-cell carcinoma in solid organ transplantation recipients to prevent the progression of the cutaneous squamous-cell carcinoma (cSCC), wherein solid organ transplantation recipients have pre-cancers including squamous cell carcinoma in Situ (also known as Bowen's disease). In some embodiments, provided herein is a method of prophylactically treating or preventing a cutaneous squamous-cell carcinoma in solid organ transplantation recipients to prevent the progression of the cutaneous squamous-cell carcinoma (cSCC), wherein solid organ transplantation recipients currently have Actinic Keratoses.

In some embodiments, provided herein is a method of treating a cutaneous squamous-cell carcinoma in patients to reduce the progression of the cutaneous squamous-cell carcinoma (cSCC), wherein the patients have chronic lymphocytic leukemia (CLL) and are also immunocompromised and susceptible to significantly elevated rates of cSCC. In some embodiments, provided herein is a method of prophylactically treating or preventing a cutaneous squamous-cell carcinoma in patients to reduce the risk of tumor progression of the cutaneous squamous-cell carcinoma (cSCC), wherein the patients have chronic lymphocytic leukemia (CLL) and are also immunocompromised and susceptible to significantly elevated rates of cSCC. In some embodiments, provided herein is a method of prophylactically treating or preventing a cutaneous squamous-cell carcinoma in patients to delay or prevent the progression of the cutaneous squamous-cell carcinoma (cSCC), wherein the patients have chronic lymphocytic leukemia (CLL) and are also immunocompromised and susceptible to significantly elevated rates of cSCC.

In some embodiments, provided herein is a method of treating a cutaneous squamous-cell carcinoma in patients to reduce the progression of the cSCC, wherein the patients have inoperable cSCC. In some embodiments, provided herein is a method of prophylactically treating or preventing a cutaneous squamous-cell carcinoma in patients to reduce the risk of tumor progression of the cSCC, wherein the patients have inoperable cSCC. In some embodiments, provided herein is a method of prophylactically treating or preventing a cutaneous squamous-cell carcinoma in patients to delay or prevent the progression of the cSCC, wherein the patients have inoperable cSCC.

In some embodiments, provided herein is a method of treating a cutaneous squamous-cell carcinoma in patients to reduce the progression of the cSCC, wherein the patients have cSCC previously removed surgically. In some embodiments, provided herein is a method of prophylactically treating or preventing a cutaneous squamous-cell carcinoma in patients to reduce the risk of tumor progression of the cSCC, wherein the patients have cSCC previously removed surgically. In some embodiments, provided herein is a method of prophylactically treating or preventing a cutaneous squamous-cell carcinoma in patients to delay or prevent the progression of the cSCC, wherein the patients have cSCC previously removed surgically.

In some or any embodiments, the tumor or skin cancer associated with cutaneous squamous-cell carcinoma to be reduced, prophylactically treated, or prevented, using the methods described herein is carcinoma.

In some embodiments, the disease to be reduced, ameliorated, treated, or prevented is a skin cancer. In some embodiments, the disease to be reduced, ameliorated, treated, or prevented is selected from the group consisting of basal cell carcinoma, squamous cell carcinoma, squamous cell carcinoma in Situ (also known as Bowen's disease), aktinic keratosis, and HPV-related squamous cell carcinoma. In some embodiments, the disease to be reduced, ameliorated, treated, or prevented is a dermal disorder associated with squamous cell carcinoma. In some embodiments, the disease to be reduced, ameliorated, treated, or prevented is a dermal disorder associated with squamous cell carcinoma in solid organ transplantation recipients. In some embodiments, the disease to be reduced, ameliorated, treated, or prevented is a dermal disorder associated with squamous cell carcinoma in patients with chronic lymphocytic leukemia (CLL).

In some embodiments, the crystalline forms of the compound of formula (I) or pharmaceutical compositions thereof described herein are used for the reduction of a MEK-inhibitor responsive skin cancer or MEK-mediated skin cancer where the subject is in need thereof.

In some embodiments, the crystalline forms of the compound of formula (I) or pharmaceutical compositions thereof described herein are used for the amelioration of a MEK-inhibitor responsive skin cancer or MEK-mediated skin cancer where the subject is in need thereof.

In some embodiments, the crystalline forms of the compound of formula (I) or pharmaceutical compositions thereof described herein are used for prevention of a MEK-inhibitor responsive skin cancer or MEK-mediated skin cancer where the subject is in need thereof.

In some embodiments, the crystalline forms of the compound of formula (I) or pharmaceutical compositions thereof described herein are used for treatment of a MEK-inhibitor responsive squamous cell carcinoma or MEK-mediated squamous cell carcinoma where the subject is in need thereof.

In some embodiments, the crystalline forms of the compound of formula (I) or pharmaceutical compositions thereof described herein are used for the reduction of a MEK-inhibitor responsive squamous cell carcinoma or MEK-mediated squamous cell carcinoma where the subject is in need thereof.

In some embodiments, the crystalline forms of the compound of formula (I) or pharmaceutical compositions thereof described herein are used for the amelioration of a MEK-inhibitor responsive squamous cell carcinoma or MEK-mediated squamous cell carcinoma where the subject is in need thereof.

In some embodiments, the crystalline forms of the compound of formula (I) or pharmaceutical compositions thereof described herein are used for prevention of a MEK-inhibitor responsive squamous cell carcinoma or MEK-mediated squamous cell carcinoma where the subject is in need thereof.

In some embodiments, the crystalline forms of the compound of formula (I) or pharmaceutical compositions thereof described herein are used for treatment of a cutaneous squamous-cell carcinoma in a subject in need thereof.

In some embodiments, the crystalline forms of the compound of formula (I) or pharmaceutical compositions thereof described herein are used for the reduction of a cutaneous squamous-cell carcinoma in a subject in need thereof.

In some embodiments, the crystalline forms of the compound of formula (I) or pharmaceutical compositions thereof described herein are used for the amelioration of a cutaneous squamous-cell carcinoma in a subject in need thereof.

In some embodiments, the crystalline forms of the compound of formula (I) or pharmaceutical compositions thereof described herein are used for prevention of a cutaneous squamous-cell carcinoma in a subject in need thereof.

In some embodiments, the subject in need thereof is a human.

In some embodiments, when the pharmaceutical composition is a topical formulation, the topical formulation is administered topically.

In some embodiments, the topical formulation is administered as a paint, a lotion, a spray, an ointment, a cream, a gel, or a patch.

VII. Combination Therapies

In some embodiments, the crystalline forms of the compound of formula (I) or a pharmaceutical composition thereof provided herein are useful in methods of treatment of a skin disorder where the subject is in need thereof, that comprise further administration of a second agent effective for the treatment of a skin disorder. The second agent can be any agent known to those of skill in the art to be effective for the treatment of dermal disorders or diseases, including those currently approved by the United States Food and Drug Administration, or other similar body of a country foreign to the United States.

In some embodiments, a crystalline form of the compound of formula (I) or a pharmaceutical composition thereof provided herein is administered in combination with one second agent. In further embodiments, a crystalline form of the compound of formula (I) or a pharmaceutical composition thereof provided herein is administered in combination with two second agents. In still further embodiments, a crystalline form of the compound of formula (I) or a pharmaceutical composition thereof provided herein is administered in combination with two or more second agents.

In some embodiments, the methods encompass the step of administering (e.g., topically) to the subject in need thereof an amount of a crystalline form of the compound of formula (I) or a pharmaceutical composition thereof provided herein in combination with a second agent effective for the treatment or prevention of skin disorders (e.g., MEK-inhibitor responsive or MEK-mediated skin disorders). The crystalline form of the compound of formula (I) can be any one of crystalline Forms A, E, F, B, C, and H as described herein; the pharmaceutical composition thereof can be any one of compositions as described herein; and the second agent can be any second agent described in the art or herein.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce one or more adverse or unwanted side effects associated with the use of either therapy alone.

The crystalline form of the compound of formula (I) or a pharmaceutical composition thereof provided herein can be administered in combination or alternation with another therapeutic agent, in particular an agent effective in the treatment of a skin disorder (e.g., MEK-inhibitor responsive or MEK-mediated skin disorders) where the subject is in need thereof. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the birthmark to be alleviated. It is to be further understood that for any particular subject, specific dosage regimens and schedules should be adjusted over time according to the individual need and the professional judgment of the person administering or supervising the administration of the compositions.

In some embodiments, dosages of the second agents to be used in a combination therapy are provided herein. In some embodiments, dosages lower than those which have been or are currently being used to treat MEK-inhibitor responsive or MEK-mediated skin conditions are used in the combination therapies provided herein. The recommended dosages of second agents can be obtained from the knowledge of those of skill in the art. For those second agents that are approved for clinical use, recommended dosages are described in, for example, Hardman et al., eds., 1996, Goodman & Gilman's The Pharmacological Basis Of Therapeutics $9^{th}$ Ed, McGraw-Hill, New York; Physician's Desk Reference (PDR) $57^{th}$ Ed., 2003, Medical Economics Co., Inc., Montvale, NJ; which are incorporated herein by reference in their entirety.

The disclosure provides combination treatments by administration of a crystalline form of the compound of formula (I) or a pharmaceutical composition thereof described herein with one or more additional agent(s) or a composition thereof. In some embodiments, the one or more additional agent(s) is selected from:

- agents that treat acne (e.g., Accutane, Azelaic acid, Benzoyl Peroxide, Salicylic acid);
- analgesics (e.g., Acetaminophen, Capsaicin), e.g., a Cox2 Inhibitor, e.g. Celecoxib);
- anesthetics (e.g., Benzocaine, Benzocaine/Menthol, Dibucaine, Diperodon, Lidocaine, Lidocaine/Prilocaine, Pramoxine);
- anti-infectives (e.g., Crotamiton);
- anti-prurittus (e.g., Ammonium lactate, Benzocaine, an ascomycin macrolactam, e.g., Pimecrolimus);
- anti-prurittus/5HT3 receptor antagonists (e.g., Ondansetron);
- antibiotics (e.g., clindamycin, doxycycline, erythromycin, tetracycline);
- anticholinergic antiemetics (e.g., diphenhydramine);
- antifibrotics (e.g., Collagenase, Pirfenidone);
- antihistamines (e.g., Triprolidine (Actifed®), Fexofenadine (Allergra®, Allegra® D-12, Allegra®-24), Astepro/Astelin Nasal Spray (Azalastine) (Dymista®), Hydroxyzine hydrochloride (Atarax®), Diphenhydramine Hydrochloride (Benadryl®), Brompheniramine (Dimetapp® Cold and Allergy Elixir), Zyrtec® (Cetirizine), Chlor-Trimeton® (Chlorpheniramine), Descoratadine (Clarinex®, Clarinex® D-12, and Clarinex® D-24), Loratadine (Claritin®, Claritin® D-12, Claritin® D-24, and Alavert®), Dimenhydrinate (Dramamine®), Diphenhydramine (Benadryl® Allergy, Nytol®, Sominex®), Doxylamine (Vicks® NyQuil®, Alka-Seltzer® Plus Night-Time Cold Medicine), Cyproheptadine (Periactin®), Promethazine (Phenergan®), Acrivastine (Semprex®, Semprex®-D), Clemastine (Tavist®), doxylamine (Unisom®), Levoceterizine (Xyzal®);
- mast cell stabalizers (e.g. Beta2-adrenergic agonists, Cromoglicic acid, cromolyn sodium, Gastrocrom®, Ketotifen, Methylxanthines, Omalizumab, Pemirolast, Quercetin, Ketotifen (Zaditen®));
- anti-inflammatory agents (e.g., NSAID (e.g. Aspirin, Choline and magnesium salicylates, Diclofenac potassium (Cataflam®), Diclofenac sodium (Voltaren®, Voltaren® XR), Diclofenac sodium with misoprostol (Arthrotec®), Diflunisal (Dolobid®), Etodolac (Lodine®, Lodine® XL), Fenoprofen calcium (Nalfon®), Flurbiprofen (Ansaid®), Ibuprofen (Advil®, Motrin®, Motrin® IB, Nuprin®), Indomethacin (Indocin®, Indocin® SR), Ketoprofen (Actron®, Orudis®, Orudis® KT, Oruvail®), Magnesium salicylate (Arthritab, Bayer® Select, Doan's Pills, Magan, Mobidin, Mobogesic) Meclofenamate sodium (Meclomen®), Mefenamic acid (Ponstel®), Meloxicam (Mobic®), Nabumetone (Relafen®), Naproxen (Naprosyn®, Naprelan®), Naproxen sodium (Aleve®, Anaprox®), Oxaprozin (Daypro®), Piroxicam (Feldene®), Rofecoxib (Vioxx®), Salsalate (Amigesic, Anaflex 750, Disalcid, Marthritic, Mono-Gesic, Salflex, Salsitab), Sodium salicylate, Sulindac (Clinoril®), Tolmetin sodium (Tolectin®), Valdecoxib (Bextra®));

Receptor Tyrosine Kinase Inhibitor (e.g. Sunitinib);

Alkylating Agents (e.g., Dacarbazine, Carboplatin);

CDK 4/6 Inhibitors (e.g., LEE011);

PKC Inhibitors (e.g., AEB071);

MAPK inhibitors (e.g., RAS Inhibitors/Farnesyltransferase inhibitor (e.g. Tipifarnib), Raf Kinase Inhibitor (e.g. Sorafenib (BAY 43-9006, Nexavar), Vemurafenib, Dabrafenib, LGX818, TAK-632, MLN2480, PLX-4720), ERK Inhibitors (e.g., SCH772984, VTX11e);

BRAF inhibitors (e.g., vemurafenib, dabrafenib)

PI3K Inhibitor (e.g., LY294002);

AKT Inhibitor (e.g., MK 2206);

PI3K/AKT Inhibitor (e.g. buparlisib, Cixutumumab);

mTOR Inhibitors (e.g. Topical Rapamycin, RAD001 (Everolimus/Rapamycin), Temsirolimus, Sirolimus);

Tyrosine Kinase Inhibitors (e.g. Imatinib (Gleevec®), Cabozantinib (inhibitor of tyrosine kinases c-Met and VEGFR2), Nilotinib (Tasigna®);

VEGF Inhibitor (e.g. Ranibizumab (Lucentis®), Cediranib);

Immune Response Modifier (e.g. Topical Imiquimod, Interferon, PEG Interferon);

Calcium Channel Blocker (e.g. Avocil (Mederma)/15% Verapamil, vitamin D separately, Doxycyline Injections);

Statin (e.g. Lovastatin, Methotrexate, Vinblastine, Pregabalin, Temozolomide, PLX3397);

HDAC Inhibitor (e.g. AR-42);

HSP-90 Inhibitors (e.g. Ganetespib);

retinoids (e.g. adapalene, Isotretinoin, tazarotene, tretinoin);

steroids (e.g. Alclometasone, Amcinonide, Betamethasone, Betamethasone dipropionate, Betamethasone dipropionate, augmented, Budesonide, Clobetasol propionate, Cortisone, Desonide, Dexamethasone, Diflorasone diacetate, Fluocinolone acetonide, Fluocinonide, Flurandrenolide, Fluticasone propionate, Halobetasol propionate, Halocinonide, Hydrocortisone, Hydrocortisone butyrate, Hydrocortisone valerate, Methylprednisolone, Mometasone, Mometasone furoate, Prednicarbate, Prednisolone, Prednisone, Triamcinolone, Triamcinolone acetonide);

topical calcineurin inhibitors (e.g., pimecrolimus (Elidel® Cream 1%, Novartis, tacrolimus (Protopic® Ointment, Astellas)); and Non-pharmaceutical Interventions (e.g. photodynamic Therapy (Levulan Kerastick Topical+light), Electrodesication (ED), YAG Laser).

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In some embodiments, two or more therapies are administered within the same patient visit. In some embodiments, the crystalline form of the compound provided herein and the second agent are administered concurrently.

In some embodiments, the crystalline form of the compound or a pharmaceutical composition thereof provided herein and the second agent are administered at about 2 to 4 days apart, at about 4 to 6 days apart, at about 1 week part, at about 1 to 2 weeks apart, or more than 2 weeks apart.

In some embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In some embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In some embodiments, a compound provided herein and a second agent are administered to a patient, in some embodiments, a mammal, such as a human, in a sequence and within a time interval such that the compound provided herein can act together with the other agent to provide an increased benefit than if they were administered otherwise. In some embodiments, the second active agent can be administered at the same time or sequentially in any order at different points in time; however, if not administered at the same time, they should be administered sufficiently close in time so as to provide the desired therapeutic or prophylactic effect. In some embodiments, the crystalline form of the compound provided herein and the second active agent exert their effect at times which overlap. Each second active agent can be administered separately, in any appropriate form and by any suitable route. In some embodiments, the crystalline form of the compound or a pharmaceutical composition thereof provided herein is administered before, concurrently or after administration of the second active agent.

In some embodiments, the crystalline form of the compound or a pharmaceutical composition thereof provided herein and the second agent are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce one or more of the side effects of one of the therapies, and/or improve the efficacy of the treatment.

In some embodiments, the crystalline form of the compound or a pharmaceutical composition thereof provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In some embodiments, courses of treatment are administered concurrently to a patient, i.e., individual doses of the second agent are administered separately yet within a time interval such that the compound provided herein can work together with the second active agent. In some embodiments, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In some embodiments, the crystalline form of the compound provided herein is administered concurrently with one or more second agents in the same pharmaceutical composition. In some embodiments, a compound provided herein is administered concurrently with one or more second agents in separate pharmaceutical compositions. In some embodiments, a compound provided herein is administered prior to or subsequent to administration of a second agent. Also contemplated are administration of a compound provided herein and a second agent by the same or different routes of administration, e.g., oral and parenteral. In some embodiments, when the compound provided herein is administered concurrently with a second agent that potentially produces one or more adverse side effects including, but not limited to, toxicity, the second active agent can advantageously be administered at a dose that falls below the threshold that the adverse side effect is elicited.

VIII. Kits

Also provided are kits for use in methods of treatment of a MEK-inhibitor responsive disorder or disease, a MEK-inhibitor responsive dermal disorder or disease, a MEK-mediated disorder or disease, or a MEK-mediated dermal disorder or disease where the subject is in need thereof; or a MEK-inhibitor responsive disorder or disease, a MEK-inhibitor responsive dermal disorder or disease, a MEK-mediated disorder or disease, or a MEK-mediated dermal disorder or disease. In some embodiments, the kit includes a crystalline form of the compound of formula (I) or a pharmaceutical composition thereof provided herein, a second agent or composition, and instructions providing information to a health care provider regarding usage for treating a MEK-inhibitor responsive disorder or disease, a MEK-inhibitor responsive dermal disorder or disease, a MEK-mediated disorder or disease, or a MEK-mediated dermal disorder or disease. Instructions may be provided in printed form or in the form of an electronic medium such as a floppy disc, CD, or DVD, or in the form of a website address where such instructions may be obtained. A unit dose of a compound or a pharmaceutical composition thereof provided herein, or a second agent or composition, can include a dosage such that when administered to a subject, a therapeutically or prophylactically effective plasma level of the compound or the pharmaceutical composition can be maintained in the subject for at least 1 day.

Also provided are kits for use in methods of treatment of a birthmark (e.g., a MEK-inhibitor responsive or MEK-mediated birthmark), where the subject is in need thereof. In some embodiments, the kit includes a crystalline form of the compound of formula (I) or a pharmaceutical composition thereof provided herein, a second agent or composition, and instructions providing information to a health care provider regarding usage for treating a birthmark (e.g., a MEK-inhibitor responsive or MEK-mediated birthmark). Instructions may be provided in printed form or in the form of an electronic medium such as a floppy disc, CD, or DVD, or in the form of a website address where such instructions may be obtained. A unit dose of a compound or a pharmaceutical composition provided herein, or a second agent or composition, can include a dosage such that when administered to a subject, a therapeutically effective plasma level of the compound or the pharmaceutical composition can be maintained in the subject for at least 1 day.

Also provided are kits for use in methods of treatment of a skin cancer (e.g., a MEK-inhibitor responsive or MEK-mediated skin cancer), where the subject is in need thereof. In some embodiments, the kit includes a crystalline form of the compound of formula (I) or a pharmaceutical composition thereof provided herein, a second agent or composition, and instructions providing information to a health care provider regarding usage for treating a skin cancer (e.g., a MEK-inhibitor responsive or MEK-mediated skin cancer). Instructions may be provided in printed form or in the form of an electronic medium such as a floppy disc, CD, or DVD, or in the form of a website address where such instructions may be obtained. A unit dose of a compound or a pharmaceutical composition provided herein, or a second agent or composition, can include a dosage such that when administered to a subject, a therapeutically effective plasma level of the compound or the pharmaceutical composition can be maintained in the subject for at least 1 day.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

IX. Embodiments

IX-1. Crystalline Form E

Embodiment E1. Crystalline Form E of a compound having formula (I):

(I)

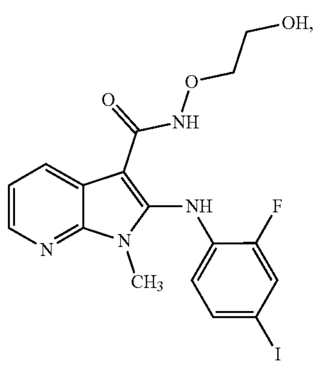

characterized by an X-ray powder diffraction (XRPD) pattern comprising peaks at 18.0, 18.3, 20.1, 20.4, and 23.5 degrees 2θ (±0.2 degrees 2θ).

Embodiment E2. The crystalline Form E of Embodiment E1, wherein the X-ray powder diffraction pattern further comprises peaks at 7.3, 15.1, 21.2, 22.8, and 24.4 degrees 2θ (±0.2 degrees 2θ).

Embodiment E3. The crystalline Form E of Embodiment E1 or E2, wherein the X-ray powder diffraction pattern further comprises peaks at 18.5, 21.9, 24.6, and 25.8 degrees 2θ (+0.2 degrees 2θ).

Embodiment E4. The crystalline Form E of Embodiment E1, wherein the X-ray powder diffraction pattern is substantially in accordance with FIG. 5.

Embodiment E5. The crystalline Form E of any one of Embodiments E1 to E4, which is substantially free of other crystalline or amorphous forms of the compound having formula (I).

Embodiment E6. The crystalline Form E of any one of embodiments E1 to E5, further characterized by a differential scanning calorimetry (DSC) thermogram comprising an endothermic peak at about 190.2° C.

Embodiment E7. The crystalline Form E of Embodiment E6, wherein the endothermic peak has an onset temperature of about 188.0° C.

Embodiment E8. The crystalline Form E of Embodiment E6, wherein the DSC thermogram is substantially in accordance with FIG. 6.

Embodiemtn E9. The crystalline Form E of any one of Embodiments E1 to E8, further characterized by a weight loss of about 0.3% upon heating from about 39° C. to about 180° C., as measured by a thermal gravimetric analysis (TGA).

Embodiment E10. The crystalline Form E of any one of Embodiments E1 to E8, further characterized by a thermal gravimetric analysis (TGA) thermogram substantially in accordance with FIG. 7.

Embodiment E11. The crystalline Form E of any one of embodiments E1 to E10, in an anhydrous form.

IX-2. Crystalline Form F

Embodiment F1. Crystalline Form F of a compound having formula (I):

(I)

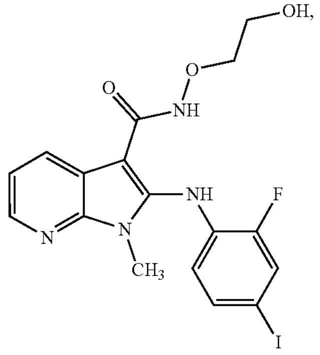

characterized by an X-ray powder diffraction (XRPD) pattern comprising peaks at 12.1, 17.8, 19.3, 22.1, and 23.3 degrees 2θ (±0.2 degrees 2θ).

Embodiment F2. The crystalline Form F of Embodiment F1, wherein the X-ray powder diffraction pattern further comprises peaks at 18.9, 19.2, 19.5, 21.1, and 22.4 degrees 2θ (±0.2 degrees 2θ).

Embodiment F3. The crystalline Form F of Embodiment F1, wherein the X-ray powder diffraction pattern is substantially in accordance with FIG. 8.

Embodiment F4. The crystalline Form F of any one of Embodiments F1 to F3, which is substantially free of other crystalline or amorphous forms of the compound having formula (I).

Embodiment F5. The crystalline Form F of any one of Embodiments F1 to F4, further characterized by a differential scanning calorimetry (DSC) thermogram comprising one or more endothermic peaks at about 162.7° C. and 187.5° C.

Embodiment F6. The crystalline Form F of Embodiment F5, wherein the endothermic peak at about 162.7° C. has an onset temperature of about 158.9° C.

Embodiment F7. The crystalline Form F of Embodiment F5, wherein the endothermic peak at about 187.5° C. has an onset temperature of about 185.3° C.

Embodiment F8. The crystalline Form F of Embodiment F5, wherein the DSC thermogram is substantially in accordance with FIG. 9.

Embodiment F9. The crystalline Form F of any one of Embodiments F1 to F8, further characterized by a weight loss of about 0.4% upon heating from about 50° C. to about 180° C., as measured by a thermal gravimetric analysis (TGA).

Embodiment F10. The crystalline Form F of any one of Embodiments F1 to F8, further characterized by a thermal gravimetric analysis (TGA) thermogram substantially in accordance with FIG. 10.

Embodiment F11. The crystalline Form F of any one of Embodiments F1 to F10, in an anhydrous form.

IX-3. Crystalline Form B

Embodiment B1. Crystalline Form B of a compound having formula (I):

(I)

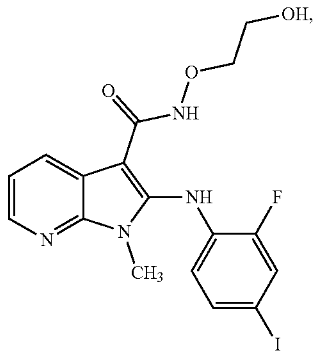

characterized by an X-ray powder diffraction (XRPD) pattern comprising peaks at 5.1, 15.1, 17.3, 17.8, and 23.8 degrees 2θ (±0.2 degrees 2θ).

Embodiment B2. The crystalline Form B of Embodiment B1, wherein the X-ray powder diffraction pattern further comprises peaks at 14.8, 16.5, 20.8, 25.0, and 28.5 degrees 2θ (±0.2 degrees 2θ).

Embodiment B3. The crystalline Form B of Embodiment B1, wherein the X-ray powder diffraction pattern is substantially in accordance with FIG. 11.

Embodiment B4. The crystalline Form B of any one of Embodiments B1 to B3, which is substantially free of other crystalline or amorphous forms of the compound having formula (I).

Embodiment B5. The crystalline Form B of any one of Embodiments B1 to B4, further characterized by a differential scanning calorimetry (DSC) thermogram comprising an endothermic peak at about 95.4° C.

Embodiment B6. The crystalline Form B of Embodiment B5, wherein the endothermic peak at about 95.4° C. has an onset temperature of about 80.0° C.

Embodiment B7. The crystalline Form B of Embodiment B5 or B6, wherein the DSC thermogram further comprises one or more endothermic peaks at about 151.1° C., about 170.3° C., and 185.3° C.

Embodiment B8. The crystalline Form B of Embodiment B5, wherein the DSC thermogram is substantially in accordance with FIG. 12.

Embodiment B9. The crystalline Form B of any one of Embodiments B1 to B8, further characterized by a weight loss of about 3.4% upon heating from about 80° C. to about 145° C., as measured by a thermal gravimetric analysis (TGA).

Embodiment B10. The crystalline Form B of any one of Embodiments B1 to B8, further characterized by a thermal gravimetric analysis (TGA) thermogram substantially in accordance with FIG. 13.

Embodiment B11. The crystalline Form B of any one of Embodiments B1 to B10, in a monohydrate form.

IX-4. Crystalline Form C

Embodiment C1. Crystalline Form C of a compound having formula (I):

(I)

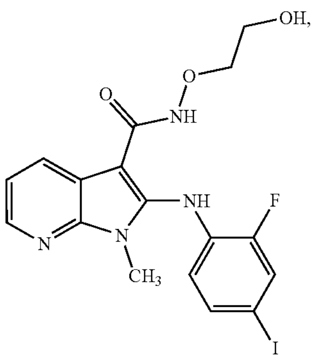

characterized by an X-ray powder diffraction (XRPD) pattern comprising peaks at 14.4, 17.4, 19.1, 19.4, and 22.3 degrees 2θ (±0.2 degrees 2θ).

Embodiment C2. The crystalline Form C of Embodiment C1, wherein the X-ray powder diffraction pattern further comprises peaks at 6.9, 11.7, 23.7, 24.9, and 25.1 degrees 2θ (±0.2 degrees 2θ).

Embodiment C3. The crystalline Form C of Embodiment C1, wherein the X-ray powder diffraction pattern is substantially in accordance with FIG. 14.

Embodiment C4. The crystalline Form C of any one of Embodiments C1 to C3, which is substantially free of other crystalline or amorphous forms of the compound having formula (I).

Embodiment C5. The crystalline Form C of any one of Embodiments C1 to C4, in a chloroform solvate form.

Embodiment C6. The crystalline Form C of Embodiment C5, wherein a ratio of chloroform to the compound of formula (I) is no more than 1:1 by mole, as determined by a crystal volume of the X-ray powder diffraction (XRPD).

Embodiment C7. The crystalline Form C of Embodiment C5, wherein a ratio of chloroform to the compound of formula (I) is about 0.4:1 by mole, as determined by a 1H NMR spectrum as shown in FIG. 15A and FIG. 15B.

IX-5. Crystalline Form H

Embodiment H1. Crystalline Form H of a compound having formula (I):

(I)

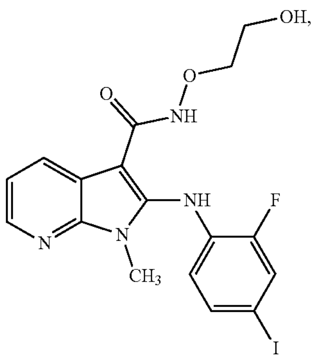

characterized by an X-ray powder diffraction (XRPD) pattern comprising peaks at 5.1, 17.3, 18.7, 23.4, and 25.6 degrees 2θ (±0.2 degrees 2θ).

Embodiment H2. The crystalline Form H of Embodiment H1, wherein the X-ray powder diffraction pattern further comprises peaks at 14.3, 16.5, 18.1, 21.02, and 22.5 degrees 2θ (±0.2 degrees 2θ).

Embodiment H3. The crystalline Form H of Embodiment H1 or H2, wherein the X-ray powder diffraction pattern further comprises peaks at 15.8, 16.3, 18.9, and 19.6 degrees 2θ (+0.2 degrees 2θ).

Embodiment H4. The crystalline Form H of Embodiment H1, wherein the X-ray powder diffraction pattern is substantially in accordance with FIG. 16.

Embodiment H5. The crystalline Form H of any one of Embodiments H1 to H4, which is substantially free of other crystalline or amorphous forms of the compound having formula (I).

Embodiment H6. The crystalline Form H of any one of Embodiments H1 to H5, in a methanol solvate form.

Embodiment H7. The crystalline Form H of Embodiment H6, wherein a ratio of methanol to the compound of formula (I) is no more than 1:1 by mole, as determined by a crystal volume of the X-ray powder diffraction (XRPD).

IX-6. Composition and Methods

Embodiment 1. A pharmaceutical composition prepared by a method comprising combining the crystalline form of any one of Embodiments E1 to E11, F1 to F11, B1 to B11, C1 to C7, and H1 to H7, with one or more pharmaceutically acceptable excipients.

Embodiment 2. The pharmaceutical composition of Embodiment 1, is a topical formulation.

Embodiment 3. The pharmaceutical composition of Embodiment 2, wherein the topical formulation in a paint, a lotion, a spray, an ointment, a cream, a gel, or a patch.

Embodiment 4. A method of treating a skin disorder comprising administering a crystalline form of any one of Embodiments E1 to E11, F1 to F11, B1 to B11, C1 to C7, and H1 to H7 or a pharmaceutical composition of any one of Embodiments 1 to 3.

Embodiment 5. The method of Embodiment 4, wherein the skin disorder is a MEK-inhibitor responsive dermal disorder or a MEK-mediated dermal disorder.

Embodiment 6. The method of Embodiment 5, wherein the MEK-inhibitor responsive dermal disorder or MEK-mediated dermal disorder is neurofibromatosis type 1.

Embodiment 7. The method of Embodiment 5, wherein the MEK-inhibitor responsive dermal disorder or MEK-mediated dermal disorder is dermal neurofibroma.

Embodiment 8. The method of Embodiment 5, wherein the MEK-inhibitor responsive dermal disorder or MEK-mediated dermal disorder is subdermal neurofibroma.

Embodiment 9. The method of Embodiment 5, wherein the MEK-inhibitor responsive dermal disorder or MEK-mediated dermal disorder is superficial plexiform neurofibroma.

Embodiment 10. The method of Embodiment 5, wherein the MEK-inhibitor responsive dermal disorder or MEK-mediated dermal disorder is dermal rasopathy.

Embodiment 11. The method of Embodiment 10, wherein the dermal rasopathy is selected from the group consisting of psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

Embodiment 12. The method of Embodiment 4, wherein the skin disorder is a birthmark.

Embodiment 13. The method of Embodiment 12, wherein the birthmark is selected from the group consisting of port-wine stains/capillary malformations, nevus cellular nevus, displastic nevi, capillary angioma, epidermal nevi, nevus sebaceous, nevus spilus, arterio-venous malformations, lymphatic malformations, and congenital melanocytic nevus.

Embodiment 14. The method of Embodiment 12 or 13, wherein the birthmark is associated with activation of p-ERK.

Embodiment 15. The method of Embodiment 13 or 14, wherein the birthmark associated with activation of p-ERK is selected from the group consisting of epidermal nevi, nevus sebaceous, nevus spilus, arterio-venous malformations, capillary malformations/port-wine stain, congenital melanocytic nevus, and lymphatic malformations.

Embodiment 16. The method of Embodiment 4, wherein the skin disorder is a skin cancer.

Embodiment 17. The method of Embodiment 16, wherein the skin cancer is a cutaneous squamous-cell carcinoma.

Embodiment 18. The method of Embodiment 16, wherein the skin cancer is a MEK-inhibitor responsive or MEK-mediated cutaneous squamous-cell carcinoma.

Embodiment 19. The method of Embodiment 17 or 18, wherein the cutaneous squamous-cell carcinoma is associated with activation of p-ERK.

Embodiment 20. The method of any one of Embodiments 4 to 19, wherein, when the pharmaceutical composition is a topical formulation, the topical formulation is administered topically.

Embodiment 21. The method of Embodiment 20, wherein the topical formulation is administered as a paint, a lotion, a spray, an ointment, a cream, a gel, or a patch

X. EXAMPLES

The following examples are provided to examples are provided to illustrate, but not limit the current description.

A. Abbreviations and Acronyms

A1 - Analytical Techniques

| Abbreviations/Acronyms | Full Name/Description |
|---|---|
| DSC | Differential scanning calorimetry |
| DVS | Dynamic (water) vapor sorption |
| NMR | Nuclear magnetic resonance spectroscopy |
| PLM | Polarized light microscopy |
| TGA | Thermogravimetry or Thermogravimetric analysis |
| vtXRPD | Variable temperature X-ray powder diffraction |
| XRPD | X-ray powder diffraction |

A2 - Crystalization Techniques

| Abbreviations/Acronyms | Full Name/Description |
|---|---|
| CC | Crash cooling |
| FE | Fast evaporation |
| SC | Slow cooling |
| SE | Slow evaporation |
| VD | Vapor diffusion |
| VS | Vapor stress |

A3 - Miscellaneous

| Abbreviations/Acronyms | Full Name/Description |
|---|---|
| API | Active pharmaceutical ingredient |
| B/E | Birefringence and extinction |
| BR | Birefringence |
| Endo/endo | Endotherm or endothermic |
| eq | Equivalent |
| Exo/exo | Exotherm or exothermic |
| FF | Free form |
| IS | Insufficient solids/sample |
| LIMS | Laboratory Information Management System |
| Max/max | Maximum or maxima |
| Obs | Observation |
| PO | Preferred orientation |
| ppt | Precipitate or precipitation |
| RH | Relative humidity |
| RT | Room temperature |
| Soln/soln | Solution |
| vac | Vacuum |

A4 - Solvents

| Abbreviations/Acronyms | Full Name/Description |
|---|---|
| ACN | Acetonitrile |
| DCM | Dichloromethane |
| $Et_2O$ | Diethyl ether |
| DMSO | Dimethylsulfoxide |
| EtOH | Ethanol |
| EtOAc | Ethyl acetate |
| IPA | Isopropyl alcohol, 2-propanol |

-continued

A4 - Solvents

| Abbreviations/Acronyms | Full Name/Description |
|---|---|
| MeOH | Methanol |
| MTBE | Methyl-tertiary-butyl ether |
| THF | Tetrahydrofuran |

Other standard abbreviations are used, including the following: NMR=nuclear magnetic resonance; d=doublet; dd=doublet of doublets; t=triplet; m=multiplet; g=gram; mg=milligram; μg=microgram; ng=nanogram; μM=micromolar; mM=millimolar; nM=nanomolar; h or hr=hour(s); min=minute(s); kDa=kilodalton; kg=kilogram; 1 or L=liter; ml or mL=milliliter; μl or μL=microliter; LC=liquid chromatography; HPLC=high-performance liquid chromatography; UPLC=ultra-performance liquid chromatography; AUC (in chromatogram)=area under the curve; LCMS=liquid chromatography and mass spectrometry; m/z=mass to charge ratio; MS=mass spectrometry; M=molarity; N=normality; rac=racemic; Rt=retention time; sat.=saturated; TLC=thin layer chromatography.

B. Glossary

B1 - Hygroscopicity

| Term | Definition[1] |
|---|---|
| Low hygroscopicity | Material exhibits <0.5 wt % water uptake over a specified RH range. |
| Limited hygroscopicity | Material exhibits <2.0 wt % water uptake over a specified RH range. |
| Significant hygroscopicity | Material exhibits ≥2.0 wt % water uptake over a specified RH range. |
| Deliquescence | Spontaneous liquefaction associated with water sorption at a specified RH condition. |
| Stoichiometric hydrate | Crystalline material with a defined water content over an extended RH range. Typical stoichiometric hydrates are hemihydrates, monohydrates, sesquihydrates, dihydrates, etc. |
| Variable hydrate | Crystalline material with variable water content over an extended RH range, yet with no phase change. |

[1]Hygroscopicity terms and definitions developed by SSCI are based in part on concepts presented in the following: Newman, A. W.; Reutzel-Edens, S. M.; Zografi, G. Characterization of the "Hygroscopic" Properties of Active Pharmaceutical Ingredients. *J. Pharm. Sci.* 2008, 97, 1047-1059.

B2 - Solubility

| Term | Definition |
|---|---|
| Low solubility | <1 mg/mL |
| Limited solubility | 1-20 mg/mL |
| Intermediate solubility | 20-100 mg/mL |
| Good solubility | 100-200 mg/mL |
| High solubility | >200 mg/mL |

B3 - XRPD Terminology

| Term | Definition |
|---|---|
| Crystalline | XRPD pattern with sharp peaks (similar to instrumental peak widths) and weak diffuse scattering relative to the peaks. |
| Disordered crystalline | XRPD pattern with broad peaks (relative to instrumental peak widths) and/or strong diffuse scattering relative to the peaks. Disordered materials may be: 1) microcrystalline, 2) crystalline with large defect density, 3) mixtures of crystalline and X-ray amorphous phases, or 4) a combination of the above. Additional analysis may be required to differentiate among these options. |
| Insufficient signal | Insufficient signal above the expected background scattering was observed. This may indicate that the X-ray beam missed the sample and/or that the sample was of insufficient mass for analysis. |
| Particle statistics artifacts | The specimen contains a small number of large crystals, which may lead to sharp spikes in the XRPD pattern. |
| Preferred orientation artifacts | The particle morphology is prone to non-random orientation in the sample holder, which may lead to subtle and/or dramatic changes in relative peak intensities. |
| No peaks | No Bragg peaks are observed in the XRPD pattern. The absence of peaks may be due to an X-ray amorphous sample and/or insufficient signal. |
| Single crystalline phase | An XRPD pattern is judged to contain evidence of a single crystalline phase if the Bragg peaks can be indexed with a single unit cell. Indexing is the process of assigning Miller index labels to each peak in a diffraction pattern. More useful than the labels is the size and shape of the crystal unit cell, which is determined during the indexing process. |
| X-ray amorphous | Diffuse scatter present, but no evidence for Bragg peaks in the XRPD pattern. X-ray amorphous materials may be: 1) nano-crystalline, 2) crystalline with a very large defect density, 3) kinetic amorphous material, 4) thermodynamic amorphous material, or 5) a combination of the above. Additional analysis may be required to differentiate among these options. |

C. Instrumental Techniques

The following methods were used for characterizing the compound of formula (I).

X-ray Powder Diffraction (XRPD)

Transmission: XRPD pattern was collected with a PANalytical X'Pert PRO MPD or PANalytical Empyrean diffractometer using an incident beam of Cu radiation produced using a long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening and asymmetry from axial divergence. Diffraction patterns were collected using a scanning position-sensitive detector (X'Celerator) located 240 mm from the specimen and Data Collector software v. 5.5.

Reflection: XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 5.5.

XRPD Indexing: Within the figure referenced for a given indexed XRPD pattern, agreement between the allowed peak positions, marked with red bars, and the observed peaks indicates a consistent unit cell determination. Successful indexing of a pattern indicates that the sample is composed primarily of a single crystalline phase unless otherwise stated. Space groups consistent with the assigned extinction symbol, unit cell parameters, and derived quantities are tabulated below the figure. To confirm the tentative indexing solution, the molecular packing motifs within the crystallographic unit cells must be determined. No attempts at molecular packing were performed.

Differential Scanning Calorimetry (DSC)

DSC was performed using a Mettler-Toledo DSC3+ differential scanning calorimeter. Temperature calibration was performed using octane, phenyl salicylate, indium, tin, and zinc. The sample was placed into a hermetically sealed aluminum DSC pan, the weight was accurately recorded, the lid was pierced, and the sample was inserted into the DSC cell. A weighed aluminum pan configured as the sample pan was placed on the reference side of the cell. The sample was analyzed from −30° C. to 250° C. at 10° C./min Thermogravimetric Analysis (TGA)

TG analysis was performed using a Mettler-Toledo TGA/DSC3+ analyzer. Temperature calibration was performed using calcium oxalate, indium, tin, and zinc. The sample was placed in an aluminum pan. The pan was hermetically sealed, the lid pierced, then inserted into the TG furnace. A weighed aluminum pan configured as the sample pan was placed on the reference platform. The furnace was heated under nitrogen. The samples was analyzed from 25° C. to 350° C. at 10° C./min.

Dynamic Vapor Sorption (DVS)

Automated vapor sorption (VS) data were collected on a Surface Measurement System DVS Intrinsic instrument. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples. Post-analysis sample was submitted for XRPD analysis.

Liquid-State Nuclear Magnetic Resonance (NMR)

The solution NMR spectra were acquired with an Avance 600 MHz NMR spectrometer. The samples were prepared by dissolving approximately 5 mg of sample in DMSO-$d_6$ containing TMS.

High-Performance or Ultra-Performance Liquid Chromatography (HPLC or UPLC)

HPLC analyses were obtained on a Waters Alliance 2695 HPLC with a Waters 2487 Dual Wavelength Detector using the methods below with the detector at the specified wavelength. LCMS analysis was conducted on a Perkin Elmer Sciex API 150EX mass spectrometer connected to a Shimadzu LC-10AD HPLC.

General Analytical Methods

UPLC Method for Purity Determination of the Compound of Formula (I)

Column: Acquity UPLC CSH C18, 1.7 μm, 2.1×150 mm
Column Temperature: 55° C.
Autosampler Temperature: 25° C.
Detection: 248 nm
Mobile Phase A: 0.05% Formic acid in water
Mobile Phase B: Acetonitrile
Gradient: see Table below
Flow Rate: 0.3 mL/min
Injection Volume: 1 μL
Injection Mode: Gradient start at injection for H-Class
Data Collection Time: 22 min
Re-equilibration Time: 7 min
Total Analysis Time: 29 min
Needle Wash: Methanol
Seal Wash: Acetonitrile/water, 50:50

| Time (min) | % A | % B |
|---|---|---|
| Initial | 90.0 | 10.0 |
| 0.5 | 90.0 | 10.0 |
| 2.0 | 75.0 | 25.0 |
| 20.0 | 10.0 | 90.0 |
| 22.0 | 10.0 | 90.0 |
| 22.5 | 90.0 | 10.0 |

Chemical Development HPLC Method

Column: Waters Atlantis T3, C18, 3.5 μm, 150×4.6 mm
Detection: 254 nm
Mobile Phase A: 0.05% formic acid in water
Mobile Phase B: 0.05% formic acid in Acetonitrile
Gradient: see Table below
Flow Rate: 0.8 mL/min

| Time (min) | % A | % B |
|---|---|---|
| 0.0 | 95.0 | 5.0 |
| 5.0 | 95.0 | 5.0 |
| 15.0 | 5.0 | 95.0 |
| 25.0 | 5.0 | 95.0 |
| 25.1 | 95.0 | 5.0 |
| 30.0 | 95.0 | 5.0 |

Example 1: Process for Preparing 2-((2-fluoro-4-iodophenyl)amino)-N-(2-hydroxyethyl)-1-methyl-1H-pyrrolo[2,3-b]pyridine-3-carboxamide (i.e., Formula (I))

Steps 1a) and 1b): Preparation of the Compound of Formula (VII)

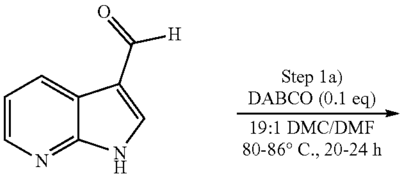

(IX)

-continued

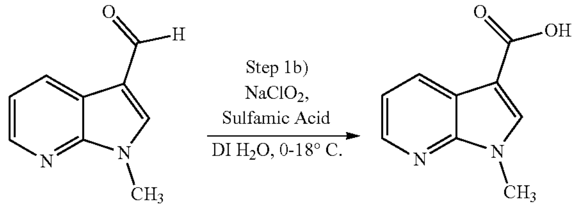

(VIII) (VII)

To a 400 L reactor was charged compound (IX) (17.0 kg), DABCO (1.31 kg), and dimethyl carbonate (164 kg, 9 vol). Stirring was started, dimethylformamide (16.0 kg, 1 vol) was charged, and the reactor was heated to 87.4° C. for 24 h. HPLC analysis showed 99.58% conversion, so the batch was cooled to 20-30° C. and was vacuum distilled (27.5 in Hg, 35.1° C.) to a final volume of 87 L (5 vol). Ethyl acetate (153 kg, 10 vol) was charged to the reactor and the batch was vacuum distilled (27.5 in Hg, <40° C.) to a final volume of 84 L (5 vol). EtOAc (153 kg, 10 vol) was charged to the reactor, and the batch was vacuum distilled (27.5 in Hg, <40° C.) to a final volume of 85 L (5 vol), and then the temperature was adjusted to 15-25° C.

To a separate vessel, a citric acid solution was prepared by charging DI $H_2O$ (50 L, 3 vol), citric acid (6.70 kg), and was stirred for 45 minutes to fully dissolve the solids. The citric acid solution was added to the reactor over 1 hour with stirring. (Note: the citric acid solution addition is slightly exothermic). EtOAc (46 kg, 3 vol) was charged to the reactor and the batch was stirred for 30 min at 15-25° C. The layers were separated (which took 20 minutes), the aqueous layer was recharged to the reactor, followed by EtOAc (123 kg, 8 vol). The layers were stirred for 20 min, were separated, the aqueous layer was recharged, followed by EtOAc (123 kg, 8 vol). The layers were stirred for 20 min, were separated, and the combined EtOAc layers were recharged to the 400 L reactor. The batch was vacuum distilled (27.5 in Hg, <40° C.) to a final volume of 80 L (5 vol). 1H NMR revealed 0% residual DABCO remained, so DI $H_2O$ (171 L, 10 vol) was charged over 30 min while maintaining the internal temperature <55° C. (Note: the water addition is exothermic). The batch was vacuum distilled (29.1 in Hg, <55° C.) to a final volume of 84 L (5 vol), and the batch was adjusted to the 13.6° C.

To a separate vessel, a sulfamic acid solution was prepared by charging DI $H_2O$ (170 L, 10 vol), sulfamic acid (28.2 kg), and stirring for 20 min. (Note: all solids may not dissolve). The sulfamic acid solution was added to the reactor with stirring over a 15 min period while maintaining the internal temperature at 8-18° C. A sodium bisulfite scrubber (48.0 kg; 250 L DI $H_2O$) and attached to the reactor. To a separate vessel, a sodium chlorite solution was prepared by charging DI $H_2O$ (85.0 L, 5 vol), sodium chlorite (25.0 kg), and was stirred for 30 min. The sodium chlorite solution was charged to the reactor over a 6 h period, with an $N_2$ flow rate of 60 L/min, while maintaining the internal batch temperature between 8-18° C. The batch temperature was then adjusted to 6.7° C. and the batch was transferred to the Rosenmund hastelloy agitated filtered and was conditioned until liquids stopped eluting. The reactor was charged with DI $H_2O$ (37.0 L, 2 vol) and the rinse was passed over the solids and was conditioned until liquids stopped eluting. The reactor was again charged with DI $H_2O$ (36.0 L, 2 vol) and the rinse was passed over the solids and was conditioned until liquids stopped eluting. The solids were transferred to a vacuum oven and dried at 45-55° C. for 100 h to give product (VII) (12.7 kg, 62%).

Specifications of obtained solid: 1H NMR (consistent with the compound (VII)); appearance: light yellow solid; KF (% water): 0.60%, 1H NMR ($d_6$-DMSO) weight assay versus 1,4-dimethoxybenzene (92.29%); and HPLC purity (area % @ 247 nm): 77.8%.

Step 2): Preparation of the Compound of Formula (VI)

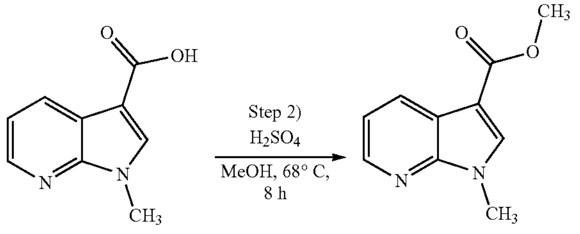

(VII) (VI)

To a 400 L reactor, inerted with $N_2$ flow at 10 L/min for 19 h, was charged compound (VII) (12.7 kg) and Methanol (202 kg, 20 vol). The stirring, which was performed at 60 RPM, was started and the batch temperature was adjusted to 10° C. Concentrated sulfuric acid (23.4 kg, 1 vol) was charged over 45 min period while maintaining the batch temperature at 10-20° C. (Note: this addition is exothermic.) The batch temperature was adjusted to 58-68° C. and was maintained in this range for 21 h. The batch was cooled to 15-25° C., and HPLC analysis revealed that compound (VI) was formed >97% relative to compound (VII), so the batch was vacuum distilled (28 in Hg, <40° C.) to a final volume of 64 L (5 vol).

In a separate vessel, a sodium hydroxide solution was prepared by mixing DI $H_2O$ (154 L, 12 vol) with 50 wt % sodium hydroxide (18.3 kg) with stirring. (Note: this addition is exothermic). The batch was cooled to 9.8° C., and the sodium hydroxide solution was added to the reactor over 45 min while maintaining the batch temperature at 10-20° C. (Note: this addition is exothermic). Upon completion of the addition, the pH was 1.73. In a separate vessel, a sodium bicarbonate solution was prepared by charging DI $H_2O$ (38 L, 3 vol), sodium bicarbonate (3.67 kg), and stirring for 30 min until all solids were fully dissolved. The sodium bicarbonate solution was charged to the reactor over 20 min, and upon completion of the addition, the pH was 6.66. The batch temperature was adjusted to 15-25° C. and the batch was transferred to the Rosenmund hastelloy agitated filtered and was conditioned until liquids stopped eluting. The reactor was charged with DI $H_2O$ (101 L, 8 vol), the rinse was transferred from the kettle onto the cake as a displacement wash. The reactor was charged with DI $H_2O$ (38.1 L, 3 vol), the rinse was transferred from the kettle to the solids, and was conditioned until liquid stopped eluting. The product was dried under nitrogen flow at 50° C. for 10 days to give compound (VI) (12.1 kg, 88% yield).

Specifications of obtained solid: 1H NMR (consistent with compound (VI)); appearance: off-white solid; KF (% water): 0.52%; 1H NMR ($d_6$-DMSO) weight assay versus 1,4-dimethoxybenzene (90.84%); and HPLC purity (area % @ 247 nm): 97.2%.

Step 3): Preparation of the Compound of Formula (V)

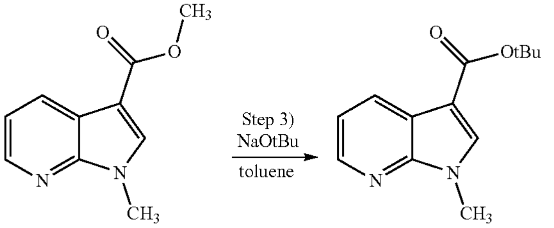

(VI) (V)

To a 400 L reactor, inerted with $N_2$ flow at 20 L/min for 20 h, was charged compound (VI) (12.1 kg), sodium tert-butoxide (21.4 kg), and anhydrous toluene (109 L, 9 vol) which was treated with StatSafe (50 ppm). The batch was stirred 80 RPM, was heated over the course of 90 min to 103° C., was held at this temperature for 45 min, and was cooled to −5-5° C. HPLC analysis showed 94.3% product.

In a separate vessel, a sodium bicarbonate solution was prepared by charging DI $H_2O$ (54.5 L, 4.5 vol), ammonium chloride (20.1 kg), and stirring the solution until all solids are fully dissolved. A 2 M HCl scrubber was attached to the reactor, and the ammonium chloride solution was charged to the reactor over 5 h while maintaining the batch temperature at 5-10° C. (Note: this addition is extremely exothermic, and heating above 15° C. will lead to decomposition). DI $H_2O$ (73.0 L, 6 vol) was charged to the reactor and the batch temperature was adjusted to 15-25° C. (Note: The DI $H_2O$ addition is slightly exothermic). EtOAc (44 kg, 4 vol) was charged, the batch was stirred for 15 minutes, and the layers were separated. The aqueous layer was recharged to the reactor, followed by EtOAc (87.5 L, 8 vol), and the layers were stirred for 15 min. The layers were separated and the combined organic layers from the first two extractions were recharged to the kettle.

The batch was vacuum distilled (29 in Hg, <65° C.) to a final volume of 124 L (10 vol). Methanol (182 L, 15 vol) was charged to the reactor and the batch was vacuum distilled (27.5 in Hg, 16.7° C.) until the final volume was 128 L (10 vol). Methanol (182 L, 15 vol) was charged to the reactor and the batch was vacuum distilled (27.3 in Hg, 17.0° C.) until the final volume was 128 L (10 vol). The batch was adjusted to 50.5° C. and DI $H_2O$ (182 L, 15 vol) was charged over 2 hours such that the batch temperature remained at 45-55° C. The batch was vacuum distilled (28.4 in Hg, <65° C.) to a final volume of 122 L (10 vol). DI $H_2O$ (60.5 L, 5 vol) was charged to the batch, and the temperature was brought to 15-25° C. The batch was stirred at this temperature for 60 hours and the batch was transferred to the Rosenmund hastelloy agitated filter and was conditioned until liquid stopped eluting. To the reactor was charged DI $H_2O$ (121 L, 10 vol) and the rinse was transferred to the solids and was conditioned until liquid stopped eluting. The product was dried under nitrogen flow at 40-70° C. for 6 days to give compound (V) (13.0 kg, 88% yield).

Specifications of obtained solid: 1H NMR (consistent with compound (V)); appearance: light yellow solid; KF (% water): 0.02%; 1H NMR ($d_6$-DMSO) weight assay versus 1,4-dimethoxybenzene (96.3%); and HPLC purity (area % @ 247 nm): 99.1%.

Steps 4a) and 4b): Preparation of the Compound of Formula (III)

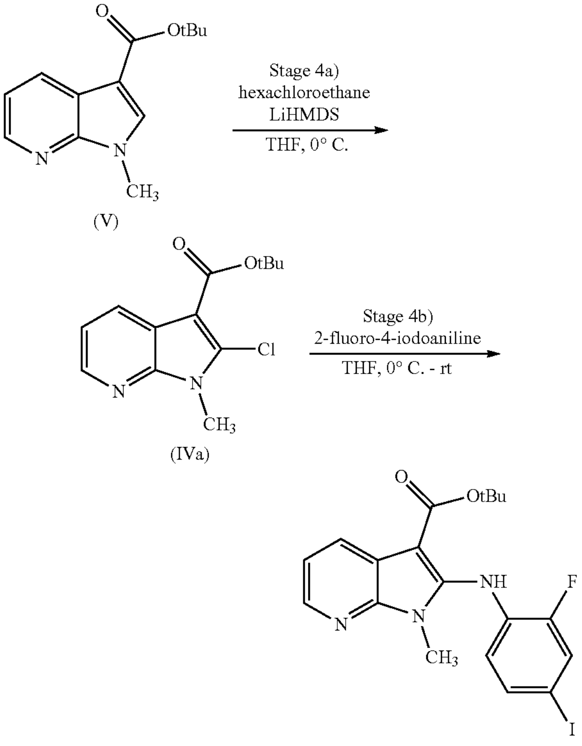

(V) (IVa) (III)

To a 400 L reactor, inerted with $N_2$ flow at 15 L/min for days, was charged 1 M LiHMDS (83.5 kg, 15.1 vol), stirring was started, and the batch temperature was adjusted to −5-5° C. In a separate vessel, inerted with $N_2$ flow at 15 L/min for days, was charged compound (V) (6.20 kg), anhydrous THF (23.1 kg (with 4.45 kg withheld to wash the kettle and lines after the transfer), 5 vol (total)), and hexachloroethane (7.27 kg), and the contents were stirred for 20 minutes to ensure all solids completely dissolved. The reaction solution was transferred to the reactor over 50 minutes to ensure the batch temperature remained at 0-10° C. (the 4.45 kg of THF withheld was used to rinse the noted solution vessel and this was also charged to the reactor during this time). After stirring for 1 h at 0-10° C., HPLC analysis revealed 100% conversion to compound (IVa).

To a separate vessel, inerted with $N_2$ flow at 15 L/min for 1 h, was charged 2-fluoro-4-iodoaniline (6.64 kg) and anhydrous THF (11.1 kg, 2 vol), and was stirred for 75 min to ensure all solids were completely dissolved. The 2-fluoro-4-iodoaniline solution was charged to the reactor over the course of 1 h to ensure the batch temperature remained at 0-10° C. The batch temperature was adjusted to 15-25° C. and stirred for 9.5 h. HPLC analysis revealed 1.2% remaining compound (IVa), so the batch temperature was adjusted to −5-5° C.

In a separate vessel, an ammonium chloride solution was prepared by charging DI $H_2O$ (18.6 kg, 3 vol) and ammonium chloride (6.88 kg) and stirring the solution for 12 minutes. (Note: all solids may not fully dissolve). The ammonium chloride solution was transferred to the reactor over the course of 75 min to ensure the batch temperature remained at 5-15° C., and the batch was vacuum distilled (27.16 in Hg, max temp 35.2° C.) to a final volume of 48.5 L (8 vol). DI $H_2O$ (75 L, 12 vol) was charged and the batch was vacuum distilled to a final volume of 94 L (16 vol). The batch temperature was adjusted to 10-20° C., EtOH (22.0 kg, 4.5 vol) was charged while maintaining the batch temperature at 10-20° C., the resulting suspension was stirred for 15 min, and the batch was filtered. The reactor was rinsed with DI $H_2O$ (62.8 L, 10 vol), the rinse was transferred to the filter, and the solids were conditioned until liquids stopped dripping.

To the reactor was charged the filtered solids, EtOH (48.9 kg, 10 vol), and the batch was heated to 40-50° C. with stirring. The batch was held at 40-50° C. for 30 min, and was then cooled to 0-10° C. The batch was filtered to the same filter used previously, the reactor was charged with EtOH (25 kg, 5 vol), and the rinse was passed over the filtered solids. The solids were conditioned until liquid stopped dripping, transferred to a vacuum oven at 50° C., and were dried for 64 h to give product (III) (11.7 kg, 93.6%).

Specifications of obtained solid: 1H NMR (consistent with compound (III)); appearance: brown solid; KF (% water): 0.041%; 1H NMR ($d_6$-DMSO) weight assay versus 1,4-dimethoxybenzene (99.4%); and HPLC purity (area % @ 247 nm): 100%.

Step 5): Preparation of the Compound of Formula (II)

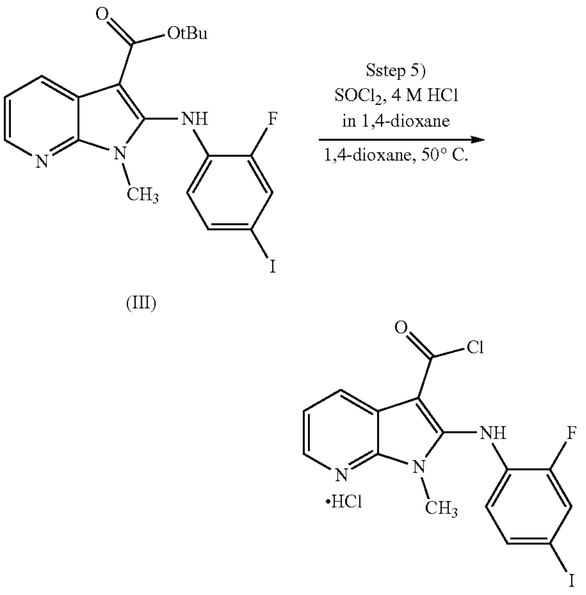

(III)

(II)

To a 400 L reactor, inerted with $N_2$ flow at 10 L/min for 1 day with a 2 M NaOH scrubber attached, was charged compound (III) (11.7 kg), 1,4-dioxane (52.5 L, 4.5 vol), and stirring was started with the batch held between 15-25° C. While maintaining the batch temperature <30° C., thionyl chloride (29.7 kg) was charged over a 45 minute period. (Note: this addition is slightly exothermic). While maintaining the batch temperature <30° C., 4 M HCl in 1,4-dioxane (39.3 kg, 6.0 eq.) was charged over a 45 minute period. (Note: this addition is slightly exothermic). The batch was heated to 50-55° C. and held at this temperature for 17 h. HPLC analysis revealed 98% conversion of compound (III) to compound (II), so the batch temperature was adjusted to 15-25° C.

To the reactor was charged n-heptane (120 L, 10 vol, treated with 200 ppm Statsafe 6000) and the batch was vacuum distilled (28 in Hg, max temp 35.6° C.) to a final volume of 86 L (7.5 vol). To the reactor was charged n-heptane (123 L, 10 vol) and the batch was vacuum distilled (28 in Hg, max temp 24.0° C.) to a final volume of 86 L (7.5 vol). To the reactor was charged n-heptane (123 L, 10 vol) and the batch was vacuum distilled (29 in Hg, max temp 20.6° C.) to a final volume of 86 L (7.5 vol). To the reactor was charged n-heptane (116 L, 10 vol) and the batch was vacuum distilled (29 in Hg, max temp 21.0° C.) to a final volume of 80 L (7.5 vol). To the reactor was charged n-heptane (120 L, 10 vol) and the batch was vacuum distilled (28 in Hg, max temp 22.0° C.) to a final volume of 83 L (7.5 vol). The batch was filtered under $N_2$, the reactor was rinsed with n-heptane (55.0 L, 5 vol), and the rinse was passed over the filtered solids. The material was dried in the filter, under vacuum, with an $N_2$ flow of 50 L/min for 3 days to give product (II) (11.8 kg, >100%).

Specifications of obtained solid: 1H NMR (NA); appearance: grey powder; KF (% water): 0.015%; 1H NMR ($d_6$-DMSO) weight assay versus 1,4-dimethoxybenzene (NA); and HPLC purity (area % @ 247 nm): 95.9%.

Steps 6a) and 6b): Preparation of the Compound of Formula (I)

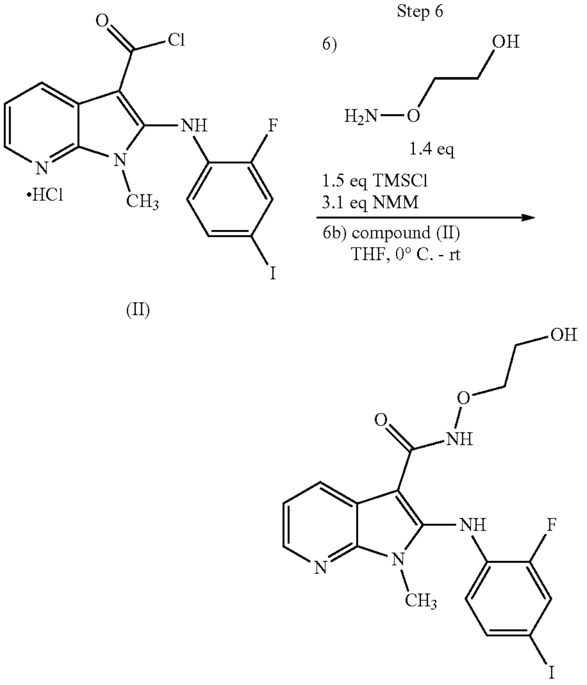

(II)

(I)

To a 400 L reactor, inerted with $N_2$ flow at 15 L/min for 26.5 h, was charged 2-(aminooxy) ethanol (2.43 kg), THF (63 L, 6 vol) and 4-methylmorpholine (7.68 L) and the batch temperature was adjusted to −5-5° C. with stirring. Chlorotrimethylsilane (4.29 L) was charged over 30 minutes such that the batch temperature remained between 0-10° C. and was stirred at this temperature for 45 min.

To a separate vessel, inerted with $N_2$ flow at 10 L/min for 5 h, was charged compound (II) (10.5 kg) and THF (105 L, 10 vol) and was stirred for 20 min at rt to form a homogeneous suspension. The compound (II) suspension was charged to the reactor over a 1.5 h period such that the batch temperature remained <10° C., and the batch was stirred at −5-5° C. for 30 min. HPLC analysis revealed 0.87% residual compound (II) relative to compound (I), so the batch temperature was adjusted to 15-25° C.

To a 200 L Schott reactor, inerted with $N_2$ flow at 20 L/min for 2 h, was charged Darco G-60 (5.25 kg). The batch was transferred to the Schott reactor and stirred with the charcoal for 45 min. This was filtered through a 0.4 μm in-line filter and was transferred back to the reactor. DI $H_2O$ (105 L, 10 vol) was charged to the reactor over a 45 min period (during which time the batch temperature rose from 13.6° C. to 24.0° C.). The batch was vacuum distilled (27 in Hg, max temp 20.7° C.) to a total of volume of 155 L (15 vol). The batch temperature was maintained at 15-25° C. and MTBE (94.5 L, 9 vol) was charged to the reactor. The batch was vacuum distilled (26 in Hg, max temp 26.6° C.) to a final volume of 133 L (13 vol). The batch temperature was maintained at 15-25° C. and MTBE (94.5 L, 9 vol) was charged to the reactor. The batch was vacuum distilled (26 in Hg, max temp 19.3° C.) to a final volume of 133 L (13 vol). The batch temperature was maintained at 15-25° C. and EtOH (94.5 L) was charged to the reactor.

The solids were filtered, the reactor was charged with DI $H_2O$ (52.5 L, 5 vol), and the rinse was passed over the collected solids. The reactor was charged with MTBE (52.5 L, 5 vol), and the rinse was passed over the collected solids. The reactor was again charged with MTBE (52.5 L, 5 vol) and the rinse was passed over the collected. The solids were charged to the reactor, followed by DI $H_2O$ (105 L, 10 vol), and the suspension was stirred at 15-25° C. for 40 min. The batch was filtered using the same filter setup, and the solids were conditioned until liquid stopped dripping. The solids were charged to the reactor, followed by EtOH (141 L, 13.5 vol), and the batch was heated to 70-80° C. and was stirred at this temperature for 32 min until the solids are nearly completely dissolved. To the reactor was charged DI $H_2O$ (105 L, 10 vol) over a minimum of 2 hours such that the batch temperature remains at 70-80° C. The batch was cooled to 10-20° C. over a 13 h period and the batch was filtered into a newly setup filter. The reactor was charged four separate times with DI $H_2O$ (52.5 L, 5 vol), and each time the rinse was passed over the collected solids as a displacement wash. The solids were conditioned until liquids stopped dripping, and were dried in a vacuum oven at 70° C. for seven days to give product (I) (5.7 kg, 53.7%).

Example 2: Crystalline Form A

The crystalline Form A was prepared according to Step-6 of Example 1.

An XRPD pattern of Form A was successfully indexed, indicating that the pattern is representative of a single crystalline phase. The indexing result provided a crystal volume estimate consistent with an anhydrous form. Form A was characterized by methods as shown in Table 1.

TABLE 1

Characterization of Crystalline Form A

| Method | Result | FIG. |
|---|---|---|
| XRPD | Form A; indexed, crystal cell volume consistent with an anhydrous form | FIG. 1 |
| DSC | endo onset 187° C. associated with decomposition | FIG. 2 |
| TGA | 0.3% wt loss up to 100° C., decomposition above 200° C. | FIG. 3 |
| KF | 0.35% (n = 3) (USP<921>) | N/A |
| $^1$H NMR | consistent with chemical structure; and no residual solvents were observed. | Not shown |
| DVS | 5-95% RH: 1.1% wt gain; and 95-5% RH: 1.2% wt loss | FIG. 4 |
| post-DVS XRPD | Form A | Not shown |

Anhydrous Form A demonstrated limited hygroscopicity, and exhibited concomitant melt/decomposition near 187° C. Form A was identified as the most thermodynamically stable form, relative to anhydrous Forms E and F, between room temperature and 50° C. (see Examples 9 and 10). In addition, Form A was found to be the predominant form, relative to the known hydrates, in solvent systems with water activity values at 0.3 or below (see Example 11).

An XRPD pattern was analyzed for Form A, and preferred orientation and particle statistic effects were not assessed. Observed peaks are shown in FIG. 1 and Table 2A, and prominent peaks are listed in Table 2B.

TABLE 2A

Observed peaks of XRPD pattern as shown in FIG. 1 of Form A

| degrees 2θ (±0.2 degrees 2θ) | d space (Å) | Intensity (%) |
|---|---|---|
| 5.34 ± 0.20 | 16.536 ± 0.619 | 93 |
| 6.66 ± 0.20 | 13.261 ± 0.398 | 13 |
| 7.95 ± 0.20 | 11.112 ± 0.279 | 77 |
| 9.59 ± 0.20 | 9.215 ± 0.192 | 20 |
| 10.70 ± 0.20 | 8.261 ± 0.154 | 6 |
| 11.42 ± 0.20 | 7.742 ± 0.135 | 15 |
| 13.10 ± 0.20 | 6.753 ± 0.103 | 45 |
| 13.33 ± 0.20 | 6.636 ± 0.099 | 4 |
| 15.97 ± 0.20 | 5.545 ± 0.069 | 23 |
| 16.58 ± 0.20 | 5.342 ± 0.064 | 23 |
| 16.85 ± 0.20 | 5.257 ± 0.062 | 4 |
| 17.98 ± 0.20 | 4.930 ± 0.054 | 14 |
| 18.28 ± 0.20 | 4.849 ± 0.053 | 100 |
| 18.52 ± 0.20 | 4.787 ± 0.051 | 79 |
| 19.28 ± 0.20 | 4.600 ± 0.047 | 38 |
| 19.81 ± 0.20 | 4.478 ± 0.045 | 15 |
| 19.96 ± 0.20 | 4.445 ± 0.044 | 11 |
| 20.21 ± 0.20 | 4.390 ± 0.043 | 24 |
| 20.51 ± 0.20 | 4.327 ± 0.042 | 44 |
| 20.71 ± 0.20 | 4.285 ± 0.041 | 41 |
| 21.06 ± 0.20 | 4.215 ± 0.040 | 25 |
| 21.39 ± 0.20 | 4.151 ± 0.038 | 38 |
| 21.74 ± 0.20 | 4.085 ± 0.037 | 43 |
| 21.88 ± 0.20 | 4.059 ± 0.037 | 34 |
| 22.41 ± 0.20 | 3.964 ± 0.035 | 28 |
| 22.55 ± 0.20 | 3.940 ± 0.034 | 32 |
| 22.75 ± 0.20 | 3.906 ± 0.034 | 27 |
| 22.95 ± 0.20 | 3.872 ± 0.033 | 22 |
| 23.20 ± 0.20 | 3.831 ± 0.033 | 8 |
| 23.98 ± 0.20 | 3.708 ± 0.030 | 51 |
| 24.30 ± 0.20 | 3.660 ± 0.030 | 88 |
| 24.67 ± 0.20 | 3.606 ± 0.029 | 30 |
| 24.79 ± 0.20 | 3.589 ± 0.028 | 26 |
| 25.60 ± 0.20 | 3.477 ± 0.027 | 16 |
| 26.44 ± 0.20 | 3.368 ± 0.025 | 33 |
| 27.17 ± 0.20 | 3.279 ± 0.024 | 34 |
| 27.42 ± 0.20 | 3.250 ± 0.023 | 10 |
| 27.77 ± 0.20 | 3.210 ± 0.023 | 29 |
| 28.26 ± 0.20 | 3.155 ± 0.022 | 30 |
| 28.66 ± 0.20 | 3.112 ± 0.021 | 7 |
| 29.18 ± 0.20 | 3.058 ± 0.021 | 21 |
| 29.40 ± 0.20 | 3.036 ± 0.020 | 18 |

TABLE 3B

| Prominent peaks of XRPD pattern as shown in FIG. 1 of Form A | | |
|---|---|---|
| degrees 2θ (±0.2 degrees 2θ) | d space (Å) | Intensity (%) |
| 5.34 ± 0.20 | 16.536 ± 0.619 | 93 |
| 7.95 ± 0.20 | 11.112 ± 0.279 | 77 |
| 9.59 ± 0.20 | 9.215 ± 0.192 | 20 |
| 13.10 ± 0.20 | 6.753 ± 0.103 | 45 |
| 15.97 ± 0.20 | 5.545 ± 0.069 | 23 |
| 16.58 ± 0.20 | 5.342 ± 0.064 | 23 |
| 18.28 ± 0.20 | 4.849 ± 0.053 | 100 |
| 18.52 ± 0.20 | 4.787 ± 0.051 | 79 |
| 19.28 ± 0.20 | 4.600 ± 0.047 | 38 |
| 20.51 ± 0.20 | 4.327 ± 0.042 | 44 |
| 20.71 ± 0.20 | 4.285 ± 0.041 | 41 |
| 21.39 ± 0.20 | 4.151 ± 0.038 | 38 |
| 21.74 ± 0.20 | 4.085 ± 0.037 | 43 |
| 23.98 ± 0.20 | 3.708 ± 0.030 | 51 |
| 24.30 ± 0.20 | 3.660 ± 0.030 | 88 |

Example 3: Crystalline Form E

An XRPD pattern of Form E was successfully indexed. The indexing results indicated that the pattern is representative of a single crystalline phase and provided a crystal volume estimate consistent with an anhydrous form. Form E was characterized by methods as shown Table 3.

TABLE 3

| Characterization of Crystalline Form E | | |
|---|---|---|
| Method | Result | FIG. |
| XRPD | Form E indexed; crystal volume consistent with anhydrous form | FIG. 5 |
| DSC | endo onset 188.0° C. immediately followed by decomposition | FIG. 6 |
| TGA | 0.3% weight loss over 39° C. to 174° C. | FIG. 7 |

The DSC thermogram of FIG. 6 exhibits a concomitant melt/decomposition endotherm with an onset near 188° C. This event is identical to that observed for Form A. The TGA thermogram of FIG. 7 exhibits a negligible weight loss prior to 180° C., consistent with an anhydrous form. Significant weight loss above 180° C. is attributed to decomposition.

Anhydrous Form E was identified as more thermodynamically stable than Form F but less stable than Form A between room temperature and 50° C. (see Examples 9 and 10). Form E was most frequently observed as a mixture with other forms from a few experiments such as an elevated temperature slurry in IPA, vapor diffusion in acetone and MTBE, and a slow cooling experiment in dry CAN (see Example 12).

The XRPD pattern was analyzed for Form E, and preferred orientation and particle statistic effects were not assessed. Observed peaks are shown in FIG. 5 and Table 4A, and prominent peaks are listed in Table 4B.

TABLE 4A

| Observed peaks of XRPD pattern as shown in FIG. 5 of Form E | | |
|---|---|---|
| degrees 2θ (±0.2 degrees 2θ) | d space (Å) | Intensity (%) |
| 3.61 ± 0.20 | 24.455 ± 1.354 | 15 |
| 6.23 ± 0.20 | 14.175 ± 0.455 | 23 |
| 6.99 ± 0.20 | 12.636 ± 0.361 | 23 |

TABLE 4A-continued

| Observed peaks of XRPD pattern as shown in FIG. 5 of Form E | | |
|---|---|---|
| degrees 2θ (±0.2 degrees 2θ) | d space (Å) | Intensity (%) |
| 7.25 ± 0.20 | 12.183 ± 0.336 | 48 |
| 8.08 ± 0.20 | 10.933 ± 0.270 | 20 |
| 9.40 ± 0.20 | 9.401 ± 0.200 | 11 |
| 10.90 ± 0.20 | 8.110 ± 0.148 | 13 |
| 12.49 ± 0.20 | 7.081 ± 0.113 | 18 |
| 13.17 ± 0.20 | 6.717 ± 0.102 | 21 |
| 14.08 ± 0.20 | 6.285 ± 0.089 | 20 |
| 14.57 ± 0.20 | 6.075 ± 0.083 | 13 |
| 15.06 ± 0.20 | 5.878 ± 0.078 | 42 |
| 15.76 ± 0.20 | 5.619 ± 0.071 | 15 |
| 16.23 ± 0.20 | 5.457 ± 0.067 | 11 |
| 18.00 ± 0.20 | 4.924 ± 0.054 | 77 |
| 18.25 ± 0.20 | 4.857 ± 0.053 | 100 |
| 18.52 ± 0.20 | 4.787 ± 0.051 | 32 |
| 18.96 ± 0.20 | 4.677 ± 0.049 | 29 |
| 19.25 ± 0.20 | 4.607 ± 0.047 | 24 |
| 19.45 ± 0.20 | 4.560 ± 0.046 | 11 |
| 19.68 ± 0.20 | 4.507 ± 0.045 | 12 |
| 20.13 ± 0.20 | 4.408 ± 0.043 | 71 |
| 20.35 ± 0.20 | 4.360 ± 0.042 | 59 |
| 21.23 ± 0.20 | 4.182 ± 0.039 | 47 |
| 21.68 ± 0.20 | 4.096 ± 0.037 | 24 |
| 21.91 ± 0.20 | 4.053 ± 0.037 | 36 |
| 22.10 ± 0.20 | 4.019 ± 0.036 | 23 |
| 22.26 ± 0.20 | 3.990 ± 0.035 | 23 |
| 22.84 ± 0.20 | 3.890 ± 0.034 | 38 |
| 23.50 ± 0.20 | 3.783 ± 0.032 | 65 |
| 23.76 ± 0.20 | 3.742 ± 0.031 | 26 |
| 23.83 ± 0.20 | 3.731 ± 0.031 | 25 |
| 24.10 ± 0.20 | 3.690 ± 0.030 | 16 |
| 24.39 ± 0.20 | 3.647 ± 0.029 | 38 |
| 24.58 ± 0.20 | 3.619 ± 0.029 | 34 |
| 25.16 ± 0.20 | 3.537 ± 0.028 | 17 |
| 25.60 ± 0.20 | 3.477 ± 0.027 | 22 |
| 25.83 ± 0.20 | 3.446 ± 0.026 | 35 |
| 26.08 ± 0.20 | 3.414 ± 0.026 | 17 |
| 26.58 ± 0.20 | 3.351 ± 0.025 | 18 |
| 26.73 ± 0.20 | 3.332 ± 0.024 | 26 |
| 27.13 ± 0.20 | 3.284 ± 0.024 | 16 |
| 27.82 ± 0.20 | 3.204 ± 0.023 | 20 |
| 28.41 ± 0.20 | 3.139 ± 0.022 | 24 |
| 28.58 ± 0.20 | 3.120 ± 0.021 | 22 |
| 29.30 ± 0.20 | 3.046 ± 0.020 | 10 |
| 29.96 ± 0.20 | 2.980 ± 0.019 | 15 |
| — | — | — |

TABLE 5B

| Prominent peaks of XRPD pattern as shown in FIG. 5 of Form E | | |
|---|---|---|
| degrees 2θ (±0.2 degrees 2θ) | d space (Å) | Intensity (%) |
| 5.34 ± 0.20 | 16.536 ± 0.619 | 93 |
| 7.25 ± 0.20 | 12.183 ± 0.336 | 48 |
| 15.06 ± 0.20 | 5.878 ± 0.078 | 42 |
| 18.00 ± 0.20 | 4.924 ± 0.054 | 77 |
| 18.25 ± 0.20 | 4.857 ± 0.053 | 100 |
| 18.52 ± 0.20 | 4.787 ± 0.051 | 32 |
| 20.13 ± 0.20 | 4.408 ± 0.043 | 71 |
| 20.35 ± 0.20 | 4.360 ± 0.042 | 59 |
| 21.23 ± 0.20 | 4.182 ± 0.039 | 47 |
| 21.91 ± 0.20 | 4.053 ± 0.037 | 36 |
| 22.84 ± 0.20 | 3.890 ± 0.034 | 38 |
| 23.50 ± 0.20 | 3.783 ± 0.032 | 65 |
| 24.39 ± 0.20 | 3.647 ± 0.029 | 38 |
| 24.58 ± 0.20 | 3.619 ± 0.029 | 34 |
| 25.83 ± 0.20 | 3.446 ± 0.026 | 35 |

Example 4: Crystalline Form F

An XRPD pattern of Form F was successfully indexed, indicating the pattern is representative of a single crystalline phase. The indexing results provided a crystal volume estimate in agreement with an anhydrous form. Form F was characterized by methods as shown Table 5.

TABLE 5

| Characterization of Crystalline Form F | | |
|---|---|---|
| Method | Result | FIG. |
| XRPD | Form F<br>indexed; crystal volume consistent with anhydrous form | FIG. 8 |
| DSC | endo onset at about 159° C.<br>immediately followed by exo; and endo onset at about 185° C.<br>immediately followed by decomposition | FIG. 9 |
| TGA | 0.4% weight loss from 50° C. to 180° C. | FIG. 10 |
| $^1$H NMR | consistent with chemical structure; and a negligible amount of ACN residue. | Not shown |

The DSC thermogram of FIG. 9 exhibits a simultaneous endotherm/exotherm with an onset near 159° C. The event is most likely the melt of Form F followed by recrystallization. A concomitant melt/decomposition endotherm with an onset near 186° C. is also observed in the DSC. The TGA thermogram of FIG. 10 exhibits a negligible weight loss prior to 180° C., consistent with an anhydrous form. Significant weight loss above 180° C. is attributed to decomposition.

Anhydrous Form F was found to be the least thermodynamically stable form, relative to anhydrous Forms A and E, between room temperature and 50° C. (see Example 10). Form F was observed from several cooling experiments in ACN or toluene (see Example 12).

The XRPD pattern was analyzed for Form F, and preferred orientation and particle statistic effects were not assessed. Observed peaks are shown in FIG. 8 and Table 6A, and prominent peaks are listed in Table 6B.

TABLE 6A

| Observed peaks of XRPD pattern as shown in FIG. 8 of Form F | | |
|---|---|---|
| degrees 2θ (±0.2 degrees 2θ) | d space (Å) | Intensity (%) |
| 5.34 ± 0.20 | 16.536 ± 0.619 | 11 |
| 7.07 ± 0.20 | 12.493 ± 0.353 | 13 |
| 7.37 ± 0.20 | 11.985 ± 0.325 | 16 |
| 9.54 ± 0.20 | 9.259 ± 0.194 | 9 |
| 12.10 ± 0.20 | 7.309 ± 0.120 | 55 |
| 15.98 ± 0.20 | 5.542 ± 0.069 | 12 |
| 16.44 ± 0.20 | 5.388 ± 0.065 | 14 |
| 17.80 ± 0.20 | 4.979 ± 0.055 | 100 |
| 18.19 ± 0.20 | 4.873 ± 0.053 | 16 |
| 18.58 ± 0.20 | 4.772 ± 0.051 | 18 |
| 18.89 ± 0.20 | 4.694 ± 0.049 | 23 |
| 19.16 ± 0.20 | 4.629 ± 0.048 | 28 |
| 19.30 ± 0.20 | 4.595 ± 0.047 | 36 |
| 19.47 ± 0.20 | 4.556 ± 0.046 | 31 |
| 19.97 ± 0.20 | 4.443 ± 0.044 | 17 |
| 20.52 ± 0.20 | 4.325 ± 0.042 | 20 |
| 21.06 ± 0.20 | 4.215 ± 0.040 | 33 |
| 21.37 ± 0.20 | 4.155 ± 0.038 | 20 |
| 22.10 ± 0.20 | 4.019 ± 0.036 | 49 |
| 22.35 ± 0.20 | 3.975 ± 0.035 | 33 |
| 23.11 ± 0.20 | 3.846 ± 0.033 | 23 |
| 23.33 ± 0.20 | 3.810 ± 0.032 | 55 |
| 23.54 ± 0.20 | 3.776 ± 0.032 | 23 |

TABLE 6A-continued

| Observed peaks of XRPD pattern as shown in FIG. 8 of Form F | | |
|---|---|---|
| degrees 2θ (±0.2 degrees 2θ) | d space (Å) | Intensity (%) |
| 23.78 ± 0.20 | 3.739 ± 0.031 | 30 |
| 23.84 ± 0.20 | 3.729 ± 0.031 | 30 |
| 24.34 ± 0.20 | 3.654 ± 0.030 | 24 |
| 24.77 ± 0.20 | 3.591 ± 0.029 | 26 |
| 25.19 ± 0.20 | 3.533 ± 0.028 | 22 |
| 25.45 ± 0.20 | 3.497 ± 0.027 | 24 |
| 25.84 ± 0.20 | 3.445 ± 0.026 | 27 |
| 26.10 ± 0.20 | 3.411 ± 0.026 | 21 |
| 27.32 ± 0.20 | 3.262 ± 0.023 | 21 |
| 28.63 ± 0.20 | 3.115 ± 0.021 | 17 |
| 29.10 ± 0.20 | 3.066 ± 0.021 | 17 |
| 29.56 ± 0.20 | 3.019 ± 0.020 | 21 |
| 30.23 ± 0.20 | 2.954 ± 0.019 | 15 |
| 30.50 ± 0.20 | 2.929 ± 0.019 | 17 |
| 30.80 ± 0.20 | 2.901 ± 0.018 | 15 |

TABLE 7B

| Prominent peaks of XRPD pattern as shown in FIG. 8 of Form F | | |
|---|---|---|
| degrees 2θ (±0.2 degrees 2θ) | d space (Å) | Intensity (%) |
| 12.10 ± 0.20 | 7.309 ± 0.120 | 55 |
| 17.80 ± 0.20 | 4.979 ± 0.055 | 100 |
| 18.89 ± 0.20 | 4.694 ± 0.049 | 23 |
| 19.16 ± 0.20 | 4.629 ± 0.048 | 28 |
| 19.30 ± 0.20 | 4.595 ± 0.047 | 36 |
| 19.47 ± 0.20 | 4.556 ± 0.046 | 31 |
| 21.06 ± 0.20 | 4.215 ± 0.040 | 33 |
| 22.10 ± 0.20 | 4.019 ± 0.036 | 49 |
| 22.35 ± 0.20 | 3.975 ± 0.035 | 33 |
| 23.33 ± 0.20 | 3.810 ± 0.032 | 55 |

Example 5: Crystalline Form B

An XRPD pattern of Form B was successfully indexed. The indexing results indicated that the pattern is representative of a single crystalline phase and provided a crystal volume estimate that can accommodate 1 mol/mol water. Form B was characterized by methods as shown Table 7.

TABLE 7

| Characterization of Crystalline Form B | | |
|---|---|---|
| Method | Result | FIG. |
| XRPD | Form B<br>indexed, crystal volume accommodates 1 mol/mol $H_2O$ | FIG. 11 |
| DSC | multiple endos onset at 80.0° C. | FIG. 12 |
| TGA | 3.4% weight loss from 80° C. to 145° C., corresponding to 1 mol/mol $H_2O$ | FIG. 13 |
| $^1$H NMR | consistent with chemical structure; and a negligible amount of residual THF | Not shown |

As shown in the DSC curve of FIG. 12, a dehydration endotherm with an onset near 80° C. is followed by multiple events up to the decomposition that occurs near ~200° C. The TGA thermogram of FIG. 13 exhibits a 3.4% weight loss concurrent with the dehydration endotherm from 80° C. to 145° C. The loss corresponds to the volatilization of ~1 mol/mol of water.

The monohydrate Form B was prevalent as mixtures with other forms from many of the experiments conducted (see Example 12). Form B can be obtained readily from aqueous solvent mixtures with a water activity of 0.5 and above (see Example 11). Exposure to elevated temperature under vacuum causes the material to become disordered (see Example 9).

The XRPD pattern was analyzed for Form B, and preferred orientation and particle statistic effects were not assessed. Observed peaks are shown in FIG. 11 and Table 8A, and prominent peaks are listed in Table 8B.

TABLE 8A

Observed peaks of XRPD pattern as shown in FIG. 11 of Form B

| degrees 2θ (±0.2 degrees 2θ) | d space (Å) | Intensity (%) |
|---|---|---|
| 5.13 ± 0.20 | 17.212 ± 0.671 | 96 |
| 10.32 ± 0.20 | 8.565 ± 0.166 | 9 |
| 11.21 ± 0.20 | 7.887 ± 0.140 | 8 |
| 11.90 ± 0.20 | 7.431 ± 0.124 | 6 |
| 14.05 ± 0.20 | 6.298 ± 0.089 | 8 |
| 14.76 ± 0.20 | 5.997 ± 0.081 | 34 |
| 15.06 ± 0.20 | 5.878 ± 0.078 | 73 |
| 15.47 ± 0.20 | 5.723 ± 0.074 | 19 |
| 16.50 ± 0.20 | 5.368 ± 0.065 | 35 |
| 16.87 ± 0.20 | 5.251 ± 0.062 | 19 |
| 17.29 ± 0.20 | 5.125 ± 0.059 | 100 |
| 17.84 ± 0.20 | 4.968 ± 0.055 | 58 |
| 18.29 ± 0.20 | 4.847 ± 0.053 | 20 |
| 19.32 ± 0.20 | 4.591 ± 0.047 | 22 |
| 19.77 ± 0.20 | 4.487 ± 0.045 | 15 |
| 20.81 ± 0.20 | 4.265 ± 0.041 | 54 |
| 21.17 ± 0.20 | 4.193 ± 0.039 | 19 |
| 21.81 ± 0.20 | 4.072 ± 0.037 | 20 |
| 22.45 ± 0.20 | 3.957 ± 0.035 | 19 |
| 22.71 ± 0.20 | 3.912 ± 0.034 | 24 |
| 23.11 ± 0.20 | 3.846 ± 0.033 | 21 |
| 23.84 ± 0.20 | 3.729 ± 0.031 | 76 |
| 24.97 ± 0.20 | 3.563 ± 0.028 | 31 |
| 25.27 ± 0.20 | 3.522 ± 0.027 | 19 |
| 25.93 ± 0.20 | 3.433 ± 0.026 | 16 |
| 26.53 ± 0.20 | 3.357 ± 0.025 | 27 |
| 26.96 ± 0.20 | 3.304 ± 0.024 | 15 |
| 27.23 ± 0.20 | 3.272 ± 0.024 | 25 |
| 27.88 ± 0.20 | 3.198 ± 0.022 | 30 |
| 28.45 ± 0.20 | 3.135 ± 0.022 | 35 |
| 28.73 ± 0.20 | 3.105 ± 0.021 | 21 |
| 29.54 ± 0.20 | 3.021 ± 0.020 | 24 |
| 30.44 ± 0.20 | 2.934 ± 0.019 | 22 |
| 31.42 ± 0.20 | 2.845 ± 0.018 | 21 |

TABLE 9B

Prominent peaks of XRPD pattern as shown in FIG. 11 of Form B

| degrees 2θ (±0.2 degrees 2θ) | d space (Å) | Intensity (%) |
|---|---|---|
| 5.13 ± 0.20 | 17.212 ± 0.671 | 96 |
| 14.76 ± 0.20 | 5.997 ± 0.081 | 34 |
| 15.06 ± 0.20 | 5.878 ± 0.078 | 73 |
| 16.50 ± 0.20 | 5.368 ± 0.065 | 35 |
| 17.29 ± 0.20 | 5.125 ± 0.059 | 100 |
| 17.84 ± 0.20 | 4.968 ± 0.055 | 58 |
| 20.81 ± 0.20 | 4.265 ± 0.041 | 54 |
| 23.84 ± 0.20 | 3.729 ± 0.031 | 76 |

Example 6: Crystalline Form C

An XRPD pattern of Form C was successfully indexed, indicating the pattern is representative of a single crystalline phase. The indexing result provided a crystal volume estimate that can accommodate up to 1 mol/mol of chloroform. Form C was characterized by methods as shown Table 9.

TABLE 9

Characterization of Crystalline Form C

| Method | Result | FIG. |
|---|---|---|
| XRPD | Form C<br>indexed; crystal volume accommodates up to 1 mol/mol $CHCl_3$ | FIG. 14 |
| $^1H$ NMR | consistent with chemical structure; and contains 0.4 mol/mol $CHCl_3$ | FIG. 15A,<br>FIG. 15B |

The solution 1H NMR spectrum of FIG. 15A and FIG. 15B contains peaks attributed to chloroform that integrates to approximately 0.4 mole of chloroform per mole of the compound of formula (I).

The XRPD pattern was analyzed for Form C, and preferred orientation and particle statistic effects were not assessed. Observed peaks are shown in FIG. 14 and Table 10A, and prominent peaks are listed in Table 10B.

TABLE 10A

Observed peaks of XRPD pattern as shown in FIG. 14 of Form C

| degrees 2θ (±0.2 degrees 2θ) | d space (Å) | Intensity (%) |
|---|---|---|
| 6.86 ± 0.20 | 12.881 ± 0.375 | 24 |
| 7.39 ± 0.20 | 11.945 ± 0.323 | 8 |
| 11.71 ± 0.20 | 7.549 ± 0.128 | 22 |
| 12.66 ± 0.20 | 6.987 ± 0.110 | 12 |
| 13.99 ± 0.20 | 6.326 ± 0.090 | 11 |
| 14.44 ± 0.20 | 6.128 ± 0.084 | 42 |
| 14.83 ± 0.20 | 5.968 ± 0.080 | 20 |
| 15.40 ± 0.20 | 5.748 ± 0.074 | 11 |
| 16.70 ± 0.20 | 5.305 ± 0.063 | 16 |
| 17.44 ± 0.20 | 5.080 ± 0.058 | 34 |
| 18.06 ± 0.20 | 4.907 ± 0.054 | 14 |
| 19.11 ± 0.20 | 4.639 ± 0.048 | 30 |
| 19.41 ± 0.20 | 4.569 ± 0.047 | 88 |
| 20.42 ± 0.20 | 4.346 ± 0.042 | 11 |
| 20.71 ± 0.20 | 4.285 ± 0.041 | 9 |
| 21.03 ± 0.20 | 4.221 ± 0.040 | 17 |
| 22.29 ± 0.20 | 3.985 ± 0.035 | 100 |
| 23.74 ± 0.20 | 3.744 ± 0.031 | 29 |
| 24.88 ± 0.20 | 3.575 ± 0.028 | 28 |
| 25.11 ± 0.20 | 3.544 ± 0.028 | 30 |
| 25.50 ± 0.20 | 3.491 ± 0.027 | 16 |
| 26.31 ± 0.20 | 3.385 ± 0.025 | 22 |
| 26.88 ± 0.20 | 3.314 ± 0.024 | 17 |
| 28.30 ± 0.20 | 3.151 ± 0.022 | 13 |
| 29.21 ± 0.20 | 3.055 ± 0.020 | 12 |
| 29.86 ± 0.20 | 2.989 ± 0.020 | 12 |
| 30.81 ± 0.20 | 2.900 ± 0.018 | 16 |
| 31.11 ± 0.20 | 2.872 ± 0.018 | 16 |
| 31.56 ± 0.20 | 2.832 ± 0.017 | 24 |
| — | — | — |

TABLE 9B

Prominent peaks of XRPD pattern as shown in FIG. 14 of Form C

| degrees 2θ (±0.2 degrees 2θ) | d space (Å) | Intensity (%) |
|---|---|---|
| 6.86 ± 0.20 | 12.881 ± 0.375 | 24 |
| 11.71 ± 0.20 | 7.549 ± 0.128 | 22 |
| 14.44 ± 0.20 | 6.128 ± 0.084 | 42 |
| 14.83 ± 0.20 | 5.968 ± 0.080 | 20 |
| 17.44 ± 0.20 | 5.080 ± 0.058 | 34 |
| 19.11 ± 0.20 | 4.639 ± 0.048 | 30 |
| 19.41 ± 0.20 | 4.569 ± 0.047 | 88 |
| 22.29 ± 0.20 | 3.985 ± 0.035 | 100 |
| 23.74 ± 0.20 | 3.744 ± 0.031 | 29 |
| 24.88 ± 0.20 | 3.575 ± 0.028 | 28 |
| 25.11 ± 0.20 | 3.544 ± 0.028 | 30 |

Example 7: Crystalline Form H

An XRPD pattern of Form H, as a damp solid, was successfully indexed, indicating the pattern is representative of a single crystalline phase. The indexing result provided a crystal volume estimate that can accommodate up to 1 mol/mol of methanol. Form H was characterized by methods as shown Table 11.

TABLE 11

Characterization of Crystalline Form H

| Method | Result | FIG. |
|---|---|---|
| XRPD | Form C<br>indexed; crystal volume accommodates up to 1 mol/mol MeOH | FIG. 16 |

The XRPD pattern was analyzed for Form H, and preferred orientation and particle statistic effects were not assessed. Observed peaks are shown in FIG. 16 and Table 12A, and prominent peaks are listed in Table 12B.

TABLE 12A

Observed peaks of XRPD pattern as shown in FIG. 16 of Form H

| degrees 2θ (±0.2 degrees 2θ) | d space (Å) | Intensity (%) |
|---|---|---|
| 5.06 ± 0.20 | 17.450 ± 0.689 | 100 |
| 9.86 ± 0.20 | 8.963 ± 0.181 | 9 |
| 10.16 ± 0.20 | 8.699 ± 0.171 | 7 |
| 11.00 ± 0.20 | 8.037 ± 0.146 | 8 |
| 11.19 ± 0.20 | 7.901 ± 0.141 | 7 |
| 14.02 ± 0.20 | 6.312 ± 0.090 | 10 |
| 14.31 ± 0.20 | 6.184 ± 0.086 | 34 |
| 15.26 ± 0.20 | 5.802 ± 0.076 | 16 |
| 15.80 ± 0.20 | 5.604 ± 0.070 | 20 |
| 15.99 ± 0.20 | 5.538 ± 0.069 | 12 |
| 16.28 ± 0.20 | 5.440 ± 0.066 | 22 |
| 16.48 ± 0.20 | 5.375 ± 0.065 | 26 |
| 17.27 ± 0.20 | 5.131 ± 0.059 | 36 |
| 18.05 ± 0.20 | 4.911 ± 0.054 | 31 |
| 18.40 ± 0.20 | 4.818 ± 0.052 | 21 |
| 18.74 ± 0.20 | 4.731 ± 0.050 | 46 |
| 18.87 ± 0.20 | 4.699 ± 0.049 | 23 |
| 19.59 ± 0.20 | 4.528 ± 0.046 | 26 |
| 19.83 ± 0.20 | 4.474 ± 0.045 | 12 |
| 20.35 ± 0.20 | 4.360 ± 0.042 | 16 |
| 20.58 ± 0.20 | 4.312 ± 0.041 | 11 |
| 21.02 ± 0.20 | 4.223 ± 0.040 | 28 |
| 22.31 ± 0.20 | 3.982 ± 0.035 | 20 |
| 22.52 ± 0.20 | 3.945 ± 0.035 | 33 |
| 22.92 ± 0.20 | 3.877 ± 0.033 | 11 |
| 23.42 ± 0.20 | 3.795 ± 0.032 | 38 |
| 24.13 ± 0.20 | 3.685 ± 0.030 | 11 |
| 24.70 ± 0.20 | 3.601 ± 0.029 | 23 |

TABLE 12A-continued

Observed peaks of XRPD pattern as shown in FIG. 16 of Form H

| degrees 2θ (±0.2 degrees 2θ) | d space (Å) | Intensity (%) |
|---|---|---|
| 25.32 ± 0.20 | 3.514 ± 0.027 | 16 |
| 25.57 ± 0.20 | 3.481 ± 0.027 | 35 |
| 26.49 ± 0.20 | 3.362 ± 0.025 | 23 |
| 27.28 ± 0.20 | 3.266 ± 0.023 | 22 |
| 27.55 ± 0.20 | 3.235 ± 0.023 | 17 |
| 27.72 ± 0.20 | 3.216 ± 0.023 | 12 |
| 28.08 ± 0.20 | 3.175 ± 0.022 | 13 |
| 28.66 ± 0.20 | 3.112 ± 0.021 | 26 |
| 28.86 ± 0.20 | 3.091 ± 0.021 | 15 |
| 29.39 ± 0.20 | 3.037 ± 0.020 | 15 |
| 29.98 ± 0.20 | 2.978 ± 0.019 | 15 |
| — | — | — |

TABLE 13B

Prominent peaks of XRPD pattern as shown in FIG. 16 of Form H

| degrees 2θ (±0.2 degrees 2θ) | d space (Å) | Intensity (%) |
|---|---|---|
| 5.06 ± 0.20 | 17.450 ± 0.689 | 100 |
| 14.31 ± 0.20 | 6.184 ± 0.086 | 34 |
| 15.80 ± 0.20 | 5.604 ± 0.070 | 20 |
| 16.28 ± 0.20 | 5.440 ± 0.066 | 22 |
| 16.48 ± 0.20 | 5.375 ± 0.065 | 26 |
| 17.27 ± 0.20 | 5.131 ± 0.059 | 36 |
| 18.05 ± 0.20 | 4.911 ± 0.054 | 31 |
| 18.74 ± 0.20 | 4.731 ± 0.050 | 46 |
| 18.87 ± 0.20 | 4.699 ± 0.049 | 23 |
| 19.59 ± 0.20 | 4.528 ± 0.046 | 26 |
| 21.02 ± 0.20 | 4.223 ± 0.040 | 28 |
| 22.52 ± 0.20 | 3.945 ± 0.035 | 33 |
| 23.42 ± 0.20 | 3.795 ± 0.032 | 38 |
| 25.57 ± 0.20 | 3.481 ± 0.027 | 35 |

Example 8: Material D

Material D is in a purported hemihydrate and the XRPD pattern of Material D could not be indexed to confirm phase purity. A dehydration endotherm with an onset near 30° C. was observed in the DSC curve concurrent with a 1.3% weight loss by TGA (occurs between 40° C. and 75° C.). The loss corresponds to the volatilization of ~0.4 mol/mol of water. The remaining events that follow are similar to those observed for Form F. Material D was predominately observed as mixtures with other forms from a few of the experiments conducted in Example 12. Results from water activity experiments of Example 11 suggest that Material D is favored from aqueous solvent systems with a water activity of ~0.4. Material D was characterized by methods as shown Table 13.

TABLE 13

Characterization of Material D

| Method | Result |
|---|---|
| XRPD | Material D<br>indexed, crystal volume accommodates 1 mol/mol $H_2O$ |
| DSC | endo near 53° C. (onset 30° C.); and<br>endo onset 164° C. followed by endo onset at 180° C. and decomposition |
| TGA | 1.3% wt loss from 40 to 75° C., corresponding to ~0.4 $H_2O$ mol/mol |
| $^1H$ NMR | consistent with chemical structure; and<br>a negligible amount of residual EtOAc |

Example 9: Stability of Crystalline Forms

Physical stability of Form A was investigated. Form A was determined to be stable for one (1) day at ambient temperature under vacuum. Form A was also stable upon exposure to 90% RH at ambient temperature over 7 days.

Physical stability of Form F was investigated. Form F was stable under vacuum at room temperature for 5 days. In addition, Form F was stable upon exposure to 90% RH at ambient temperature over 7 days.

Physical stability of Form B was investigated. Form B was stable under vacuum at ambient temperature over 2 days. However, exposure to 45° C. under vacuum provided a slightly disordered XRPD pattern with additional unidentified peaks. An in situ variable temperature X-ray powder diffraction (vtXRPD) experiment suggested that Form B eventually converts/crystallizes to anhydrous Form E at a higher temperature (e.g., 178° C.).

Physical stability of Form C was investigated. Form C became slightly disordered upon exposure to an elevated temperature (about 42° C. to 45° C.) under vacuum, for example at about 42° C. for one day or at about 45° C. for three days.

Because the solids of Form H were originally isolated damp with excess MeOH (see Example 7), an attempt to remove the excess solvent under vacuum (i.e., room temperature for 2 days) was performed. The resulting solids were a disordered mixture of Form H and Form A determined by an XRPD pattern, suggesting that the solvate Form H is not physically stable under this condition.

Example 10: Binary Competitive Interconversion Experiments-Thermodynamic Relationship of Forms A, E, and F Phase transitions of solids can be thermodynamically reversible or irreversible. Crystalline forms which transform reversibly at a specific transition temperature are called enantiotropic polymorphs. If the crystalline forms are not interconvertible under these conditions, the system is monotropic (one thermodynamically stable form). Several rules, utilizing calorimetry data, help predict the relative thermodynamic stability of polymorphs and whether the relationship between the polymorphs is enantiotropic or monotropic. Unfortunately, due to concomitant decomposition at the melt, calorimetry data obtained within this study were not suitable for this purpose.

Alternatively, interconversion experiments were performed to determine the thermodynamic relationship between polymorphs. Interconversion or competitive slurry experiments are a solution-mediated process that provides a pathway for the less soluble (more stable) crystal to grow at the expense of the more soluble crystal form [Bernstein, J. *Polymorphism in Molecular Crystals*. Clarendon Press, Oxford, 2006; and *Polymorphism in Pharmaceutical Solids*. Brittain, Harry G. ed. Marcek Dekker, Inc. New York. 1999]. Outside the formation of a solvate or degradation, the resulting more stable polymorph from an interconversion experiment is independent of the solvent used because the more thermodynamically stable polymorph has a lower energy and therefore lower solubility. The choice of solvent affects the kinetics of polymorph conversion and not the thermodynamic relationship between polymorphic forms [Gu, C H., Young, V. Jr., Grant, D J. *J. Pharm. Sci.* 2001, 90 (11): 1878-1890].

Slurries were prepared at ambient and 50° C. using binary mixtures of Forms A/F, A/E, and E/F. Saturated solutions of the compound of formula (I) were generated in EtOAc or ACN at RT or 50° C. The solutions were filtered and approximately equivalent quantities of two of the polymorphs were added to the solutions. The samples were slurried for several days at the given temperature and the solids were collected by positive pressure filtration, or centrifugation/decantation. The solids were harvested and analyzed by an XRPD.

The results of the interconversion studies are provided in Table 14.

TABLE 14

Binary Competitive Interconversion Slurry Experiments

| Binary mixtures | Solvent | Days | T (° C.) | Form harvested |
|---|---|---|---|---|
| Forms A/F | ACN | 7 | 50 | Form A |
| | | 7 | RT | Form A |
| | EtOAc | 7 | 50 | Form A |
| | | 7 | RT | Form A |
| Forms A/E | ACN | 5 | 50 | Form A |
| | | 5 | RT | Form A |
| | EtOAc | 5 | 50 | Form A |
| | | 5 | RT | Form A |
| Forms E/F | ACN | 5 | 50 | Form A |
| | | 5 | RT | Form E + minor Form F |
| | EtOAc | 5 | 50 | Form E |
| | | 5 | RT | Form E + minor Form F |

The solution-mediated interconversion process provides a pathway for the less soluble (more stable relative to the other) crystal to grow at the expense of the more soluble crystal form. However, when neither of the forms involved in the binary competitive slurry is the most thermodynamically stable form, the possibility of the most stable crystal to grow at the expense of the other two more soluble crystal forms can also result. See Form A obtained in the binary mixture of Forms E and F. This solvent-mediated polymorphic transformation is controlled by its nucleation rate, which is generally higher in a solvent giving higher solubility. In addition to the solubility, the strength of the solvent-solute interactions is also important. Degree of agitation and temperature also change the polymorphic transformation rate by influencing the crystallization kinetics of the more stable polymorph. In solvents giving a low solubility, because of a high interfacial energy, the metastable zone may be wider than the solubility difference between two polymorphs, such that the critical free energy barrier for nucleation cannot be overcome (see Gu et. al., *J. Pharm. Sci.* 2001).

Form A resulted when utilized in the binary mixtures, confirming that Form A is more stable relative to Form E or F. If Form A did not spontaneously nucleate, Form E resulted or was the predominant form from binary mixtures of Forms E/F. This indicates that Form E is more stable relative to Form F. Monotropy is inferred within the temperature range studied. In summary, the thermodynamic stability between RT and 50° C. is ranked as Form A>Form E>Form F (between RT and 50° C.).

Example 11: Binary Competitive Experiments-Hydration State vs. Water Activity

The effect of water activity ($a_w$) on the hydration state of the compound of formula (I) was investigated through competitive water activity trituration experiments (slurries) in aqueous ACN, MeOH, or EtOH. Slurry experiments of a binary mixture of Forms A/B or Form A/Material D were used to establish the predominant form of the compound at various $a_w$. The resulting solid phase was characterized by XRPD.

Water activity is related to relative humidity in that RH $\%=a_w \times 100$. Therefore, it is possible to directly relate the stability of an anhydrous/hydrate system in slurry experiments to solid-state stability. Literature suggests that the slurry technique at controlled water activities provides an accurate method of rapidly predicting the physically stable form in anhydrous/hydrate systems [Ticehurst M D, Storey R A, Claire W. Application of slurry bridging experiments at controlled water activities to predict the solid-state conversion between anhydrous and hydrated forms using theophylline as a model drug. *Int J Pharm.* 2002; 247:1-10; Sacchetti M. Determining the relative physical stability of anhydrous and hydrous crystal forms of GW2016. *Int J Pharm.* 2004; 273:195-202; Zhu H, Yuen C, Grant D J W. Influence of water activity in organic solvent+water mixtures on the nature of the crystallizing drug phase. 1. Theophylline. *Int J Pharm.* 1996; 135:151-160; and Zhu H, Grant D J W. Influence of water activity in organic solvent+water mixtures on the nature of the crystallizing drug phase. 2. Ampicillin. *Int J Pharm.* 1996; 139:33-43]. The method is particularly valuable when relatively slow kinetics of conversion in the solid state prevents reaching true equilibrium in a reasonable timeframe, since solvent-mediated transformation accelerates the conversion process.

The results are provided in Table 15.

TABLE 15

Binary Competitive Slurry Experiments

| Binary Mixture | ($a_w$) Water Activity[a] | Solvent (v/v) | Days | T (° C.) | Form harvested |
|---|---|---|---|---|---|
| Forms A/B | 0.50 | 97:3 ACN/$H_2O$ | 5 | RT | Form B* |
| Forms A/B | 0.40 | 84:16 MeOH/$H_2O$ | 5 | RT | Form A, Form B, and minor Material D* |
| Forms A/B | 0.30 | 95:5 EtOH/$H_2O$ | 5 | RT | Form A* |
| Forms A/B | 0.20 | 97:3 EtOH/$H_2O$ | 5 | RT | Form A* |
| Form A/ Material D | 0.20 | 97:3 EtOH/$H_2O$ | 5 | RT | Form A* |
| Form A/ Material D | 0.10 | 97:3 MeOH/$H_2O$ | 5 | RT | Form A* |

[a]Water activities calculated using UNIFAC calculator; and

*XRPD pattern was acquired on damp/wet solids

Anhydrous Form A is the predominant form at and below 0.30 $a_w$ and monohydrate Form B is favored at and above 0.50 $a_w$. Material D, the hemihydrate, even though not in the original binary mixture used, became evident at 0.40 $a_w$—an intermediate value between the stable regions for either the monohydrate and anhydrous forms. Given enough time, Material D would have likely become the predominant form at that condition. In summary, the favored anhydrous/hydrate form at room temperature for specific water activity values is ranked as $$\text{Form } A \leq 0.30\ a_w < \text{Material } D \text{ at about } 0.40\ a_w < 0.50\ a_w \leq \text{Form } B (\text{at } RT)$$

Example 12: Polymorph Screen Experiments

A lot of the compound of formula (I) containing a mixture of Forms A and B was used for this study. Measured aliquots of a variety of solvents were added to weighed amounts of the material with sonication until the solution appeared clear or the maximum volume of the vial was reached. Solubility was calculated based on the total solvent used to give a solution. Actual solubility may be greater because of the volume of the solvent portions used or a slow rate of dissolution. The approximate solubility of this material was visually estimated with a variety of solvents and solvent mixtures at ambient temperature as shown in Table 16. Values are rounded to the nearest whole number. If dissolution did not occur as determined by visual assessment, the value is reported as "<". If dissolution occurred as determined by the visual assessment after the addition of the first aliquot, the value is reported as ">".

TABLE 16

Approximate Solubility of the Compound of Formula (I)

| Solvent | Solubility (mg/mL) |
|---|---|
| acetone | 8 |
| ACN | 2 |
| DCM | 6 |
| EtOAc | 3 |
| EtOH | 3 |
| heptane | <1 |
| $H_2O$ | <1 |
| MeOH | 11 |
| THF | 29 |
| toluene | <1 |
| 3:1 acetone/$H_2O$ (v/v) ($a_w$ = 0.85[a]) | 5 |
| 1:1 THF/$H_2O$ (v/v) ($a_w$ = 1.04[a]) | 11 |

[a]Water activities calculated using UNIFAC calculator.

Limited solubility was observed in acetone, ACN, DCM, EtOAc, EtOH, MeOH, 3:1 v/v acetone/$H_2O$, and 1:1 v/v THF/$H_2O$. THF showed a slightly improved solubility of 29 mg/mL while heptane, $H_2O$, and toluene showed low solubility of less than 1 mg/mL. The solubility values were considered in the design of form screen experiments.

The above noted material was then used for a solvent-based screen designed to crystallize and potentially identify different crystalline forms. Over 40 experiments were conducted in a variety of solvents using numerous crystallization techniques at different temperatures (below RT, RT, and elevated temperatures). Crystallization techniques include crash cooling, slow cooling, fast evaporation, slow evaporation, slurrying experiments, vapor diffusion, and vapor stressing, as described below.

Crash Cooling (CC): Clear solutions of the compound of formula (I) were prepared in EtOAc and IPA at 50-60° C. Vials were transferred to a freezer at about −20° C. Solids were collected by stated technique.

Slow Cooling (SC): Clear solutions of the compound of formula (I) were prepared in ACN and toluene at 60° C. Heat was turned off to the reactor block and samples slowly cooled to room temperature in the hot block. Solids were collected by stated technique.

Fast Evaporation (FE): Clear solutions of the compound of formula (I) were prepared in a variety of solvents. Vials were left uncapped and solvent evaporated at ambient conditions.

Slow Evaporation (SE): A clear solution of the compound of formula (I) was prepared in a variety of solvents. The vial was capped with aluminum foil perforated with a hole and the solvent evaporated at ambient conditions.

Slurrying Experiments: Saturated solutions of the compound of formula (I) were prepared in various solvents and solvent mixtures. Mixtures were stirred at different temperatures (e.g., below RT, RT, and elevated temperatures) for the noted duration of time. Solids were collected by centrifugation and subsequent decantation. Damp solids were analyzed by XRPD.

Vapor Diffusion (VD): Saturated solutions of the compound of formula (I) were prepared in a variety of solvents in 1-dram vials. The 1-dram vials were left uncapped and placed in a 20-mL vial containing a given antisolvent. The larger vial was capped and left at ambient temperature for a given amount of time. Any solids were collected and analyzed by XRPD.

Vapor Stressing (VS): Solids of the compound of formula (I) was placed inside 1-dram vials. The 1-dram vials were placed, uncapped, in 20-ml vials containing different solvents. Resulting solids were analyzed by XRPD.

Isolating of solids can be any one of techniques as described below.

Positive Pressure Filtration: Solids were collected on 0.2-μm nylon or PTFE filters by pressing a slurry at specified temperature, through a syringe and Swinnex filter holder assembly. In general, solids were dried briefly by blowing a 20-mL syringe of air over the filter.

Decantation: Clear solutions were removed via disposable pipette and discarded, leaving damp solids behind.

Generated solids were observed by polarized light microscopy (PLM) and/or analyzed by an X-ray powder diffraction (XRPD). Many samples were analyzed by XRPD while still damp with the crystallization solvents. Most of these samples were subsequently dried under vacuum at various temperatures in attempts to desolvate them.

The results of polymorph screen experiments are listed in Table 17.

TABLE 17

Polymorph Screen Experiments

| Exp. No. | Solvent | Conditions | Observation | Form(s) by XRPD |
|---|---|---|---|---|
| a | acetone | FE | white; needles | A |
| b | | 1) VD w/$H_2O$, RT, 4 d<br>2) decanted & dried w/$N_2$ | 1) solids in clear solution<br>2) white; needles | A |
| c | | 1) VD w/MTBE, RT, 20 d<br>2) decanted & dried w/$N_2$ | 1) solids in clear solution<br>2) spherulites | A + minor E |
| d | | 1) VD w/toluene, RT, 4 d<br>2) decanted & dried w/$N_2$ | 1) solids in clear solution<br>2) white; needles | A |
| e | ACN | VS, RT, 7 d | fines | A + B + minor F |
| f | | FE | off-white; fines | A + B |
| g | | 1) SC, 60° C. to RT<br>2) ref., 2-8° C., 2 d<br>3) decanted & dried w/$N_2$ | 1) solids above solvent<br>2) solids in clear solution<br>3) damp, rosettes | F* |
| h | | 1) SC, 60° C. to RT<br>2) seed w/Form F<br>3) fridge, 2-8° C., 6 d<br>4) decanted & dried w/$N_2$ | 1) clear solution<br>2) clear solution w/solids<br>3) solids in clear solution<br>4) damp; rosettes | F* |
| i | | 1) SC, 60° C. to RT<br>2) seed w/Form F<br>3) fridge, 2-8° C., 3 d<br>4) vacuum filtration | 1) clear solution<br>2) solids present<br>3) clear solution w/solids<br>4) 67% yield; needles | B + minor F |
| j | | 1) SC, 60° C. to RT<br>2) RT, 1 d<br>3) ref., 2 to 8° C., 1 d<br>4) decanted<br>5) vac. oven, RT, 1 d | 1) clear solution<br>2) solution w/particles<br>3) solids in clear solution<br>4) damp solids<br>5) white; needles | F + E |
| k | chloroform | FE | white; needles | C |
| l | DCM | SE | white; spherulite | A + D |
| m | EtOAc | VS, RT, 7 d | white; fines | A + B |
| n | | SE | needles | A + D |
| o | | 1) CC, 60 to −20° C.<br>2) frz, −20° C., 3 d<br>3) decanted & dried w/$N_2$ | 1) clear solution<br>2) solids in clear solution<br>3) fines | D |

TABLE 17-continued

| Polymorph Screen Experiments | | | | |
|---|---|---|---|---|
| Exp. No. | Solvent | Conditions | Observation | Form(s) by XRPD |
| p | | 1) CC, 60 to −20° C.<br>2) frz, −20° C., 6 d<br>3) decanted & dried w/$N_2$ | 1) clear solution<br>2) solids in clear solution<br>3) white | D + minor B |
| q | | 1) CC, 50 to −20° C.<br>2) frz, −20° C., 14 d | 1) clear solution<br>2) soln w/few particles | IS |
| r | EtOH | FE | off-white; needles | A + minor D |
| s | $H_2O$ | VS, RT, 7 d | white; fines | A + B + peaks |
| t | IPA | 1) CC, 60 to −20° C.<br>2) frz, −20° C., 6 d | 1) clear solution<br>2) clear solution | — |
| u | | 1) A and E in IPA<br>2) stirred, 55° C., 9 d<br>3) pos. pressure filtration<br>4) vac. oven, RT, 3 d | 1) white slurry<br>2) white slurry<br>3) white solids<br>4) free-flowing | A + E |
| v | MeOH | SE | white; needles | A + peaks |
| w | | 1) VD w/$Et_2O$, RT, 20 d | clear solution | — |
| x | | 1) VD w/$H_2O$, RT, 5 d<br>2) decanted & dried w/$N_2$ | 1) solids in clear solution<br>2) long needles | A |
| y | | VD w/toluene, RT, 20 d | clear solution | — |
| z | THF | SE | white; spherulites | A + D |
| aa | | 1) VD w/heptane, RT, 4 d<br>2) decanted & dried w/$N_2$ | 1) solids in clear solution<br>2) white; needles | A + minor D |
| bb | | 1) VD w/MTBE, RT, 20 d | clear solution | — |
| cc | | 1) VD w/toluene, RT, 5 d<br>2) decanted & dried w/$N_2$ | 1) solids in brown solution<br>2) rosettes | A + D |
| dd | toluene | 1) SC, 60 to RT<br>2) ref., 2-8° C., 2 d<br>3) decanted & dried w/$N_2$ | 1) clear solution<br>2) solids in clear solution<br>3) damp, rosettes | F* |

*XRPD pattern was acquired on damp/wet solids

Example 13: Form Conversion Experiments

In search of robust form conversion conditions, a few form conversion experiments were attempted in various solvents at room temperature by charging 0.5 wt % of Form A of the compound of formula (I). The experiments were performed by charging the compound, Form A 5 seeds, and 20 vol. of a respective solvent, as shown in Table 18.

TABLE 18

| Form Conversion Experiments | | | | | |
|---|---|---|---|---|---|
| Entry | Scale (g) | Conditions | Yield | Water % by KF | Final Form (Form A) |
| 1 | 5.0 | 1.0 eq. Compound, 0.5 wt % Form A, 20 vol. $CH_3CN$, rt, 24 h | 4.20 g (84%) | 0.12% | No |
| 2 | 5.0 | 1.0 eq. Compound, 0.5 wt % Form A, 20 vol. Acetone, rt, 24 h | 3.25 g (65%) | 0.25% | No |
| 3 | 5.0 | 1.0 eq, Compound, 0.5 wt % Form A, 20 vol. $H_2O$, rt, 24 h. | 4.7 g (94%) | — | No |
| 4 | 10.0 | 1.0 eq. Compound, 17 vol. EtOH, 76.3° C., 13 vol. $H_2O$ at ≥75° C., 0.5 wt % Form A, isolation at 10° C. | 9.3 g (93%) | 0.12% | No |
| 5 | 5.0 | 1.0 eq. Compound, 0.5 wt % Form A, 20 vol. $CH_3CN$, 60° C., 4 h | 4.56 g (91.2%) | 0.11% | No |
| 6 | 5.0 | 1.0 eq. Compound, 0.5 wt % Form A, 20 vol. Acetone, 55° C., 4 h | 3.80 g (76%) | 0.18% | No |

Entries 1-3: The resultant slurry was stirred at RT for 24 h before filtration. The isolated compound of formula (I) from each experiment was submitted for XRPD analysis of wet cake and oven-dried material. The XRPD pattern of the wet cake and dried material was similar and consistent with the starting material of the compound.

Entry 4: The experiment was performed in EtOH/$H_2O$, where $H_2O$ was charged slowly at 75° C. over an hour and 20 min. After completion of $H_2O$ charge, batch remains as a solution and thin slurry formation started after 15 min of stirring under the same condition. After this time, the batch was cooled to 10° C. over 14 hours and held at 10° C. for 5 h before filtration. The wet cake isolated from this experiment was analyzed by XRPD and the pattern was not consistent with Form A.

Entries 5-6: Two re-slurry experiments with 0.5 wt % seed (Form A) were performed in $CH_3CN$ and acetone at 55° C. and 60° C., respectively. Both experiments produced an anhydrous crystalline form, a similar form with each other. The material was isolated from room temperature experiments. However, the crystalline form of the isolated material was not consistent with the desired Form A.

Example 14: Crystallization of Compound of Formula (I) From THF/MTBE Using Form A Seeds To develop a robust crystallization process of the compound of formula (I), several experiments were conducted from THF/MTBE using Form A seeds, as shown in Table 19. From A (batch 2) of Example 2 was used as Form A seeds.

TABLE 19

Crystallization of the Compound in THF/MTBE with Form A seeds

| Entry | 1 | 2 | 3 |
|---|---|---|---|
| Conditions | Compound (1 equiv.), THF (10 vol), MTBE (20 vol.), 55° C. to 40° C., 1 h, to 20° C. over 2 h, 20° C., 1 h | Compound (1 equiv.), THF (10 vol), MTBE (20 vol.), 55° C. to 40° C., 1 h, to 20° C. over 2 h, 20° C., 1 h | Compound (1 equiv.), THF (10 vol), MTBE (20 vol.), 55° C. to 40° C., 1 h, to 20° C. over 30 min, 20° C., 14 h |
| Input scale & Form | 4 g & Form A | 10 g & crystalline | 1 g & crystalline |
| Input lot and (% AUC) | 96.95 (by HPLC) | 99.60 (by UPLC) | |
| Purity of the isolated compound | 99.79[1] | — | — |
| Yield (%) & Form | 91.5% & Form A | 88.8% & Form A | 86% & Form A |

Entry 1: About 4 g of the compound (96.95% AUC) was dissolved in 10 vol. THF at 55° C. and cooled the solution at 40° C. Charged MTBE (20 vol.) over 1 h while maintaining the batch temperature to 40° C. and 1 wt % of Form A was charged after 8 vol. charge of MTBE. For this case, the reaction mixture was turned into thin slurry before charging the seeds. Still, the HPLC purity of the compound isolated was 99.79% AUC as Form A. Recovery yield was 91.5% and impurity at 20.7 min purged from 2.6% AUC to 0.11% AUC.

Entry 2: Another experiment was performed almost similarly on the 10 g scale of the compound (99.6% AUC). The only difference was 1 wt % seeds of Form A were charged after charging 4 vol. of MTBE into the reaction. Seeds survived and the mixture turned into slurry. It was continued charging MTBE in the reaction and the final product isolated after aging at 20° C. for 2 h as Form A. The recovery from this experiment was 88.8%.

Entry 3: To determine the stable nucleation point, 1 g of the compound (99.6% AUC) was dissolved in THF (10 vol.) and charged Form A seeds at 40° C. Seeds survived and became more thick slurry over standing 30 min. After this time, MTBE charged while maintaining the batch temperature at 40° C. The final product was isolated from this experiment as Form A with a recovery yield of 86%. This new recrystallization process was demonstrated in Example 16.

Example 15: Slurry to Slurry Form Conversion Using Form A Seeds

Slurry-to-slurry form conversions of the compound of formula (I) were performed in premixed THF/MTBE and $EtOH/H_2O$ with Form A seeds in various amounts, as described in Table 20. From A (batch 2) of Example 2 was used as Form A seeds.

TABLE 20

Slurry Form Conversion of the Compound in THF/MTBE and $EtOH/H_2O$ with Form A seeds

| Entry | 1 | 2 | 3 | 4 | 5 | 6 |
|---|---|---|---|---|---|---|
| Conditions | Compound (1 equiv.), Form A, THF/MTBE (30 vol., 1:2), 45° C., 36 h | | | | Compound (1 equiv.), Form A, $EtOH/H_2O$ (22.5 vol., 12.5:10), 60° C., 36 h | |
| Form A Seeds (wt %) | 10 mg (2) | 25 mg (5) | 50 mg (10) | 100 mg (20) | 30 mg (6) | 75 mg (15) |
| Scale (g) | Lot-1: 0.5 g | | | | Lot-2: 0.5 g | |
| Isolated Form | Crystalline | Form A | Form A | Form A | Crystalline | Crystalline |

The above experiments showed that 5-20 wt % seeds were able to convert the compound of formula (I) in any other forms to the desired Form A in THF/MTBE system while fail to convert to the desired form experiments performed in EtOH/$H_2O$. The process by slurry form conversion in THF/MTBE remains to be an alternative method in manufacturing Form A of the compound of formula (I).

Example 16: Process for Preparing Form A of the Compound of Formula (I)

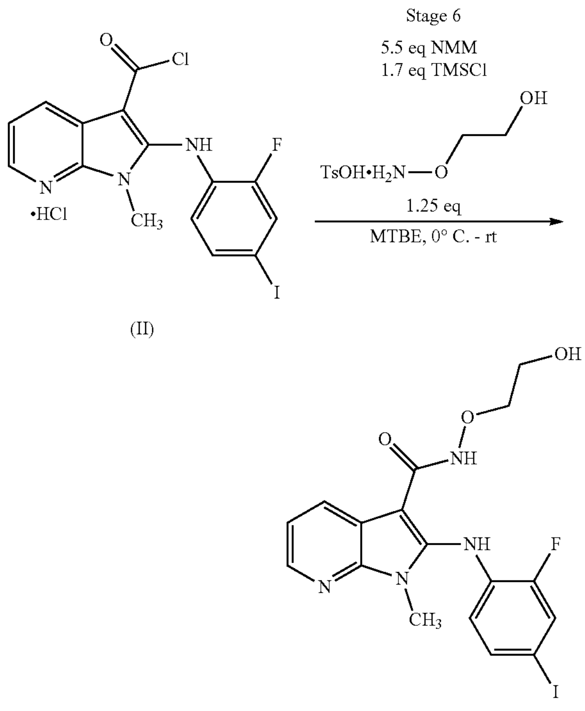

(II)

(I)

To a 10-L reactor were charged $HOCH_2CH_2NH_2$·TsOH (227 g, 0.91 mol, 1.25 equiv.) and MTBE (1.36 L, 4.0 vol.) and start agitation at 20±5° C. Charged NMM (441 mL, 3.54 mol, 5.5 equiv.) and continued stirring the batch under same condition for 30 min. The batch was filtered after this time and the cake washed with MTBE (2×0.51 L, 2×1.5 vol.). The combined filtrate and washes was transferred back into the reactor and cooled to 0° C. Slowly charged TMSCl (0.157 L, 1.24 mol, 1.7 equiv.) while maintaining the batch temperature below 5° C. The batch aged for 45 minutes before charging the compound of formula (II) slurry. In a 5 L 3-necked RBF equipped with mechanical stir were charged the compound (II) (340 g, 0.73 mol, 1.0 equiv.) followed by MTBE (3.4 L, 10 vol.) and stirred for 35 min for uniform slurry before charge this slurry for amide coupling. The compound (II) slurry was transferred using a transfer pump over 1 h 20 min while maintaining the reaction temperature below 8° C. The RBF was rinsed with MTBE (0.34 L, 1 vol.) and added to the batch. The batch was continued stirring at 5° C. before warmed to 20±5° C. and stirred at that temperature for 30 min. After this time, in process control sample was pulled and HPLC analysis indicated 99.85% conversion of compound (II) to compound (I). The batch was filtered to remove all solids and the reactor was rinsed with THF (2×0.68 L, 2×2 vol.) and applied for cake wash. The filtrate was returned to a clean reactor and the batch was distilled under vacuum to a final volume of ~1.7 L (5 vol.). Charged ethanol (3.4 L, 10 vol.) to the reactor and the batch was distilled a second time to ~1.7 L (THF at 0.81 mol % to EtOH in 1H NMR). The mixture was cooled to 20° C. and charged ethanol (2.89 L, 8.5 vol.) and water (0.68 L, 2 vol.). The mixture was warmed to 80° C. (all solids were not dissolved completely) and water (2.72 L, 8 vol.) was added over 2 h. The batch turned into a solution after charging ~1.8 L of DI $H_2O$ and remains a clear solution after completion of $H_2O$ charge. The mixture was cooled over 13 h to 10° C. The batch was aged at 10° C. for 4 h before filtration. The reactor was rinsed with water (4×1.7 L) and transferred from reactor onto the cake. The wet cake (783 g) was dried at 60° C. for 3 days (Note: There was no weight loss after 26 h of drying) to give 240 g of crude compound (I) (70%). The HPLC purity of the crude compound (I) was 98.81% AUC and water content by KF was 0.28 wt %.

The crude compound (I) (238 g) and THF (3.4 L) were charged to a 10-L reactor. The batch was warmed to 51.2° C. (target was 60° C.) to dissolve the product. After complete dissolution, batch was cooled to 40° C. before charging Darco G60 (170 g, 50 wt %) and the slurry was aged for 30 min and then was filtered to remove the carbon (over 340 g celite). The reactor and filter cake was rinsed with THF (2×1.9 L, 2×3.5 vol.). The combined filtrate and washes was passed through a 0.2 μm in-line filter and returned to the cleaned reactor. The batch was vacuum distilled to ~1.7 L (5 vol.), and then heated to 60-65° C. for dissolution. Complete dissolution of the batch observed after charging additional THF (0.68 L, 1+1=2 vol.) then adjusted batch temperature to 40° C. and charged Form A Seeds (3.4 g, Form A, batch 2 of Example 2). Continued stirring under same condition for 30 min before start dosing of MTBE (4.76 L, 14 vol.) to the mixture over 1 h 30 min while maintaining the batch temperature at 40° C. The batch was cooled to 20° C. over 2 h and was aged at 20° C. for one hour before filtration. The reactor and filter cake were rinsed with MTBE (2×0.68 L, 2×2 vol.). The wet cake weighed 455 g and was dried at 45° C. for 36 h to afford 189 g of compound (I) (55% yield). The 1H NMR analysis of the product was consistent with the assigned structure, the HPLC purity was 99.88% AUC, and XRPD pattern is consistent with Form A of compound (I) (e.g., FIG. 1).

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. Crystalline Form A of a compound having formula (I):

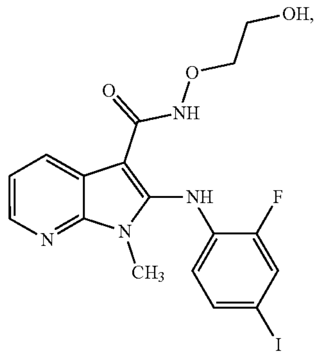

(I)

characterized by an X-ray powder diffraction (XRPD) pattern comprising peaks at 5.3, 8.0, 18.3, 18.5, and 24.3 degrees 2θ (±0.2 degrees 2θ).

2. The crystalline Form A of claim 1, wherein the X-ray powder diffraction pattern further comprises peaks at 13.1, 20.5, 20.7, 21.7, and 24.0 degrees 2θ (±0.2 degrees 2θ).

3. The crystalline Form A of claim 1, wherein the X-ray powder diffraction pattern further comprises peaks at 9.6, 16.0, 16.6, 19.3, and 21.4 degrees 2θ (±0.2 degrees 2θ).

4. The crystalline Form A of claim 1, wherein the X-ray powder diffraction pattern is substantially in accordance with FIG. 1.

5. The crystalline Form A of claim 1, which is substantially free of other crystalline or amorphous forms of the compound having formula (I).

6. The crystalline Form A of claim 1, further characterized by a differential scanning calorimetry (DSC) thermogram comprising an endothermic peak at about 189.9° C.

7. The crystalline Form A of claim 6, wherein the endothermic peak has an onset temperature of about 187.1° C.

8. The crystalline Form A of claim 6, wherein the DSC thermogram is substantially in accordance with FIG. 2.

9. The crystalline Form A of claim 1, further characterized by a weight loss of about 0.1% to 1% upon heating to about 100° C., as measured by a thermal gravimetric analysis (TGA).

10. The crystalline Form A of claim 9, wherein the weight loss is about 0.3% upon heating from about 40° C. to about 100° C., as measured by the thermal gravimetric analysis.

11. The crystalline Form A of claim 1, further characterized by a thermal gravimetric analysis (TGA) thermogram substantially in accordance with FIG. 3.

12. The crystalline Form A of claim 1, further characterized by a weight gain of about 1.1% after undergoing a dynamic vapor sorption cycle from about 5% relative humidity (RH) to about 95% RH at 25° C.

13. The crystalline Form A of claim 1, further characterized by a weight loss of about 1.2% after undergoing a dynamic vapor desorption cycle from about 95% relative humidity (RH) to about 5% RH at 25° C.

14. The crystalline Form A of claim 1, having a dynamic vapor sorption profile substantially as shown in FIG. 4.

15. The crystalline Form A of claim 1, in an anhydrous form.

16. A pharmaceutical composition prepared by a method comprising combining the crystalline Form A of claim 1, with one or more pharmaceutically acceptable excipients.

17. The pharmaceutical composition of claim 16, is a topical formulation.

18. The pharmaceutical composition of claim 17, wherein the topical formulation in a paint, a lotion, a spray, an ointment, a cream, a gel, or a patch.

19. A method for preparing crystalline Form A according to claim 1, comprising:

a) forming a first mixture comprising a compound having formula (I):

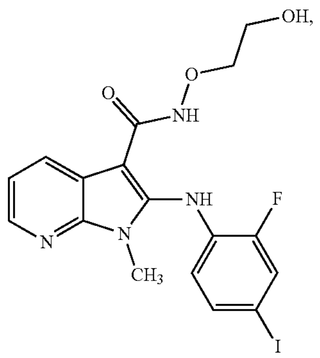

(I)

and tetrahydrofuran (THF) at a first temperature of from about 50° C. to about 65° C.;

b) cooling the first mixture to a second temperature of from about 35° C. to about 45° C.;

c) adding one or more seeds of the crystalline Form A prior to step d) to form a second mixture, or during step d);

d) adding methyl-tertiary-butyl ether (MTBE) to form a third mixture;

e) cooling the third mixture to a third temperature of no more than about 25° C. to form a fourth mixture comprising a precipitate; and f) isolating the precipitate from the fourth mixture to provide the crystalline Form A, wherein steps c) and d) are each maintained at the second temperature.

20. A method for preparing crystalline Form A according to claim 1, comprising:

a) forming a third slurry comprising a compound having formula (I):

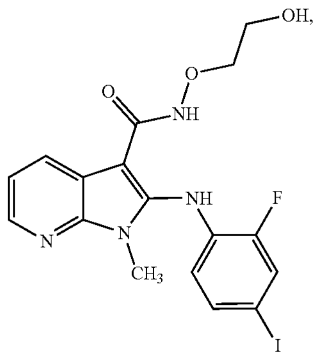

(I)

tetrahydrofuran (THF) and methyl-tertiary-butyl ether (MTBE);

b) adding one or more seeds of the crystalline Form A to form a fourth slurry;

c) stirring the fourth slurry to form a fifth slurry; and d) isolating a precipitate from the fifth slurry to provide the crystalline Form A, wherein the one or more seeds of the crystalline Form A are in an amount of at least about 5% by weight of the compound of formula (I); and steps a) to c) are each maintained at a temperature of from about 40° C. to about 50° C.

* * * * *